(12) United States Patent
Hirashima et al.

(10) Patent No.: US 12,038,424 B2
(45) Date of Patent: Jul. 16, 2024

(54) GAS SENSOR, COMPONENT DETECTION APPARATUS INCLUDING GAS SENSOR, INSPECTION SYSTEM INCLUDING GAS SENSOR, GAS SENSOR INSPECTION METHOD, AND GAS SENSOR MANUFACTURING METHOD

(71) Applicant: ASAHI KASEI KABUSHIKI KAISHA, Tokyo (JP)

(72) Inventors: Daiki Hirashima, Tokyo (JP); Hidenori Mochizuki, Tokyo (JP); Takanori Murakami, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 403 days.

(21) Appl. No.: 17/438,070

(22) PCT Filed: Mar. 13, 2020

(86) PCT No.: PCT/JP2020/011265
§ 371 (c)(1),
(2) Date: Sep. 10, 2021

(87) PCT Pub. No.: WO2020/184721
PCT Pub. Date: Sep. 17, 2020

(65) Prior Publication Data
US 2022/0205963 A1     Jun. 30, 2022

(30) Foreign Application Priority Data
Mar. 13, 2019   (JP) .................................. 2019-046295

(51) Int. Cl.
*G01N 33/00* (2006.01)
*G01N 27/12* (2006.01)

(52) U.S. Cl.
CPC ........... *G01N 33/007* (2013.01); *G01N 27/12* (2013.01); *G01N 33/0027* (2013.01)

(58) Field of Classification Search
None
See application file for complete search history.

(56) References Cited

U.S. PATENT DOCUMENTS 7,556,775 B2   7/2009   McGill et al.
9,506,822 B2   11/2016  Yoshikawa et al.
(Continued)

FOREIGN PATENT DOCUMENTS

JP   H07-193256 A    7/1995
JP   2003-332587 A   11/2003
(Continued)

OTHER PUBLICATIONS

International Preliminary Report on Patentability dated Aug. 25, 2021, issued in corresponding International Patent Application No. PCT/JP2020/011265.
(Continued)

*Primary Examiner* — Daniel S Larkin
(74) *Attorney, Agent, or Firm* — Morgan, Lewis & Bockius LLP

(57) ABSTRACT

A gas sensor includes an electrically conductive membrane that bends with an applied surface stress, a fixing member disposed outside the membrane, a coupling portion that couples together the membrane and the fixing member, a flexible resistor whose resistance value changes in accordance with a deflection that occurs in the coupling portion, a conductive support substrate connected to the fixing member and disposed with a gap between the membrane and the coupling portion, a receptor which is formed on an area including the center of a surface on one side of the membrane which is opposite to the other side facing the support (Continued)

substrate, and deforms in accordance with a substance adsorbed, a first terminal capable of applying a first potential to the membrane, a second terminal capable of applying a second potential to the support substrate, and an insulating portion electrically insulating the fixing member from the support substrate.

18 Claims, 60 Drawing Sheets

(56) References Cited

U.S. PATENT DOCUMENTS

| | | |
|---|---|---|
| 2003/0215974 A1 | 11/2003 | Kawasaki et al. |
| 2006/0161364 A1 | 7/2006 | Wang et al. |
| 2013/0133433 A1 | 5/2013 | Yoshikawa et al. |
| 2014/0352447 A1 | 12/2014 | Yoshikawa et al. |

FOREIGN PATENT DOCUMENTS

| | | | |
|---|---|---|---|
| JP | 2007-147374 | A | 6/2007 |
| JP | 2008-0527329 | A | 7/2008 |
| JP | 2015-045657 | A | 3/2015 |
| JP | 5743026 | B2 | 7/2015 |
| JP | 2018-132325 | A | 8/2018 |
| JP | 2019-035613 | A | 3/2019 |
| WO | 2015/198185 | A1 | 12/2015 |

OTHER PUBLICATIONS

International Search Report (with partial translation) and Written Opinion issued in corresponding International Patent Application No. PCT/2020/011265, dated Apr. 7, 2020.

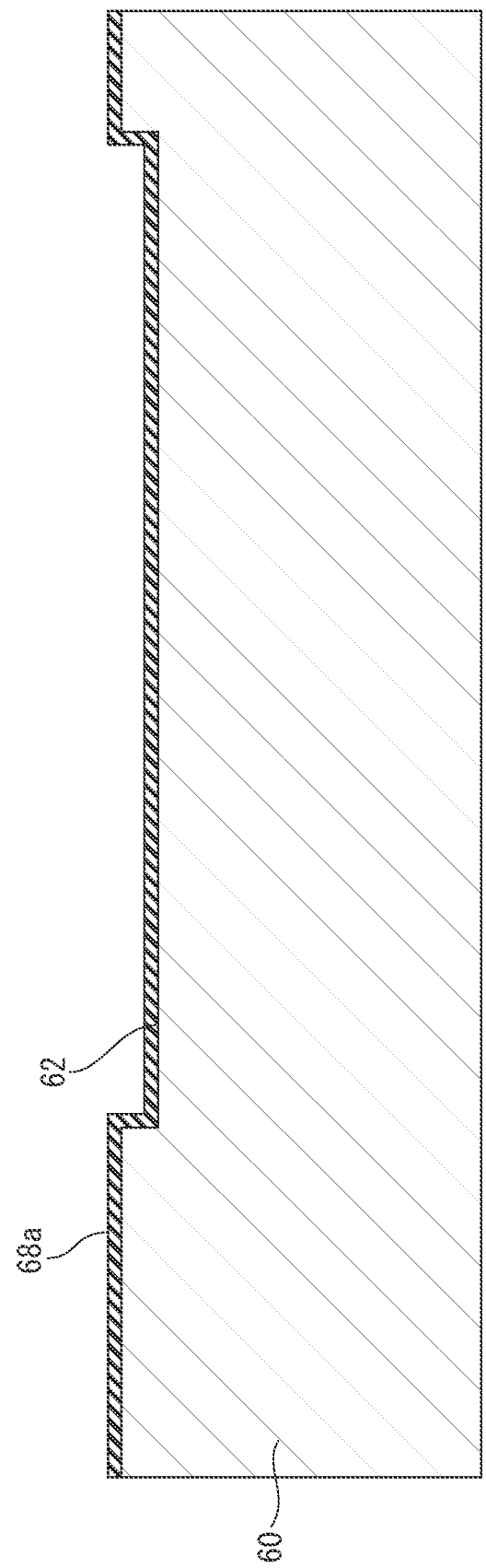

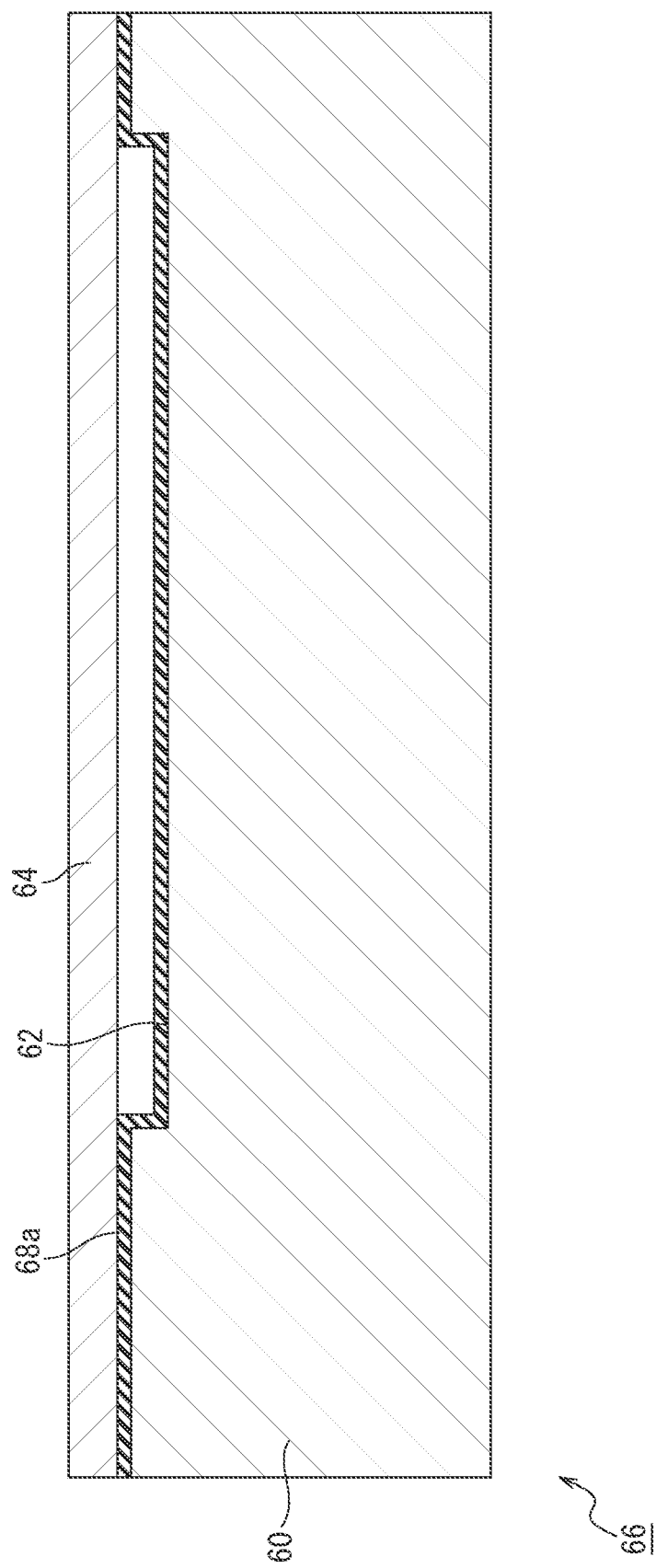

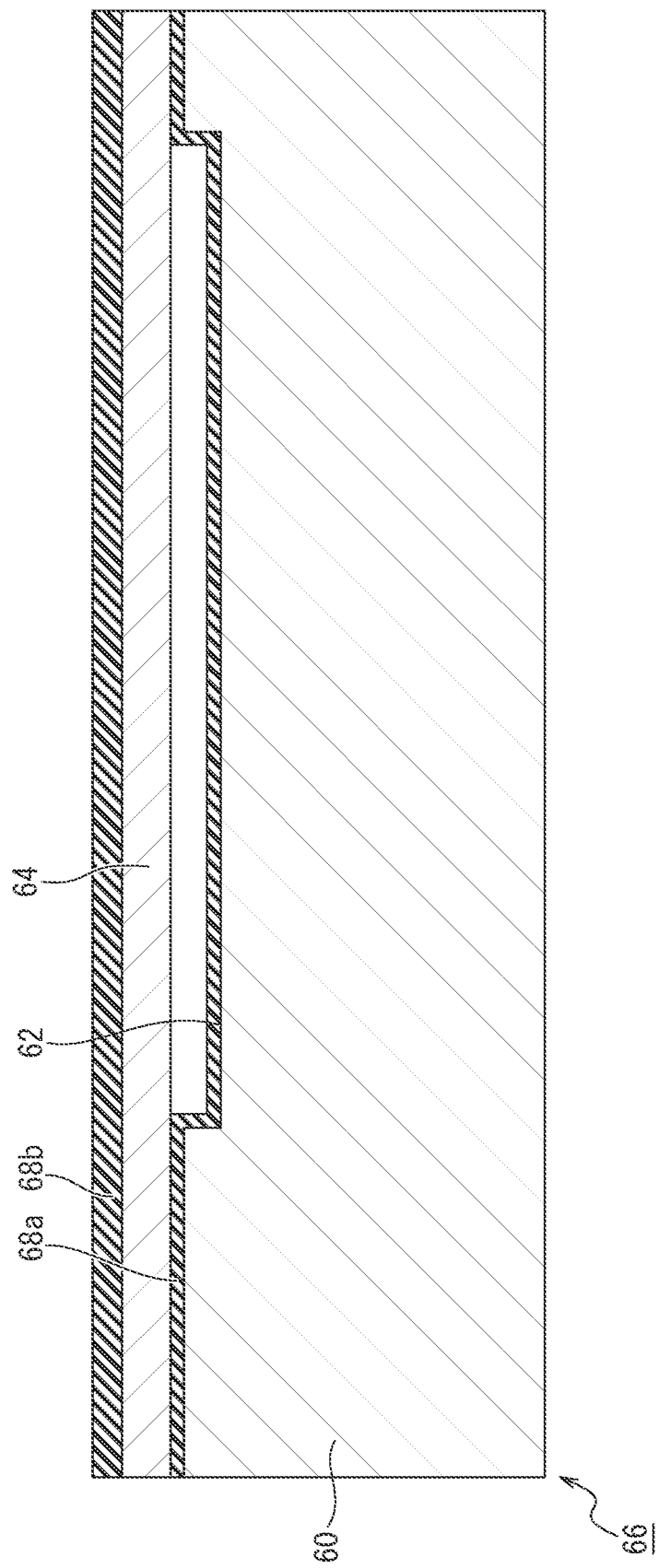

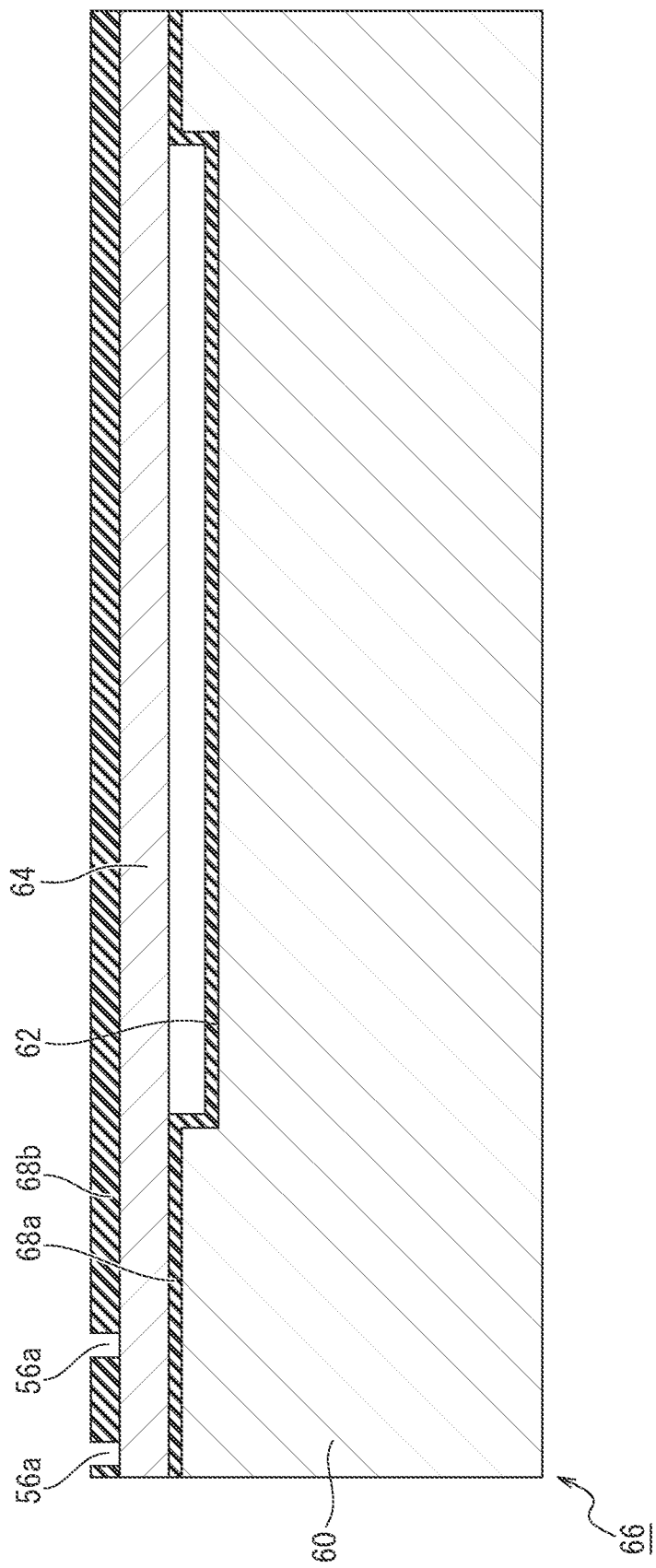

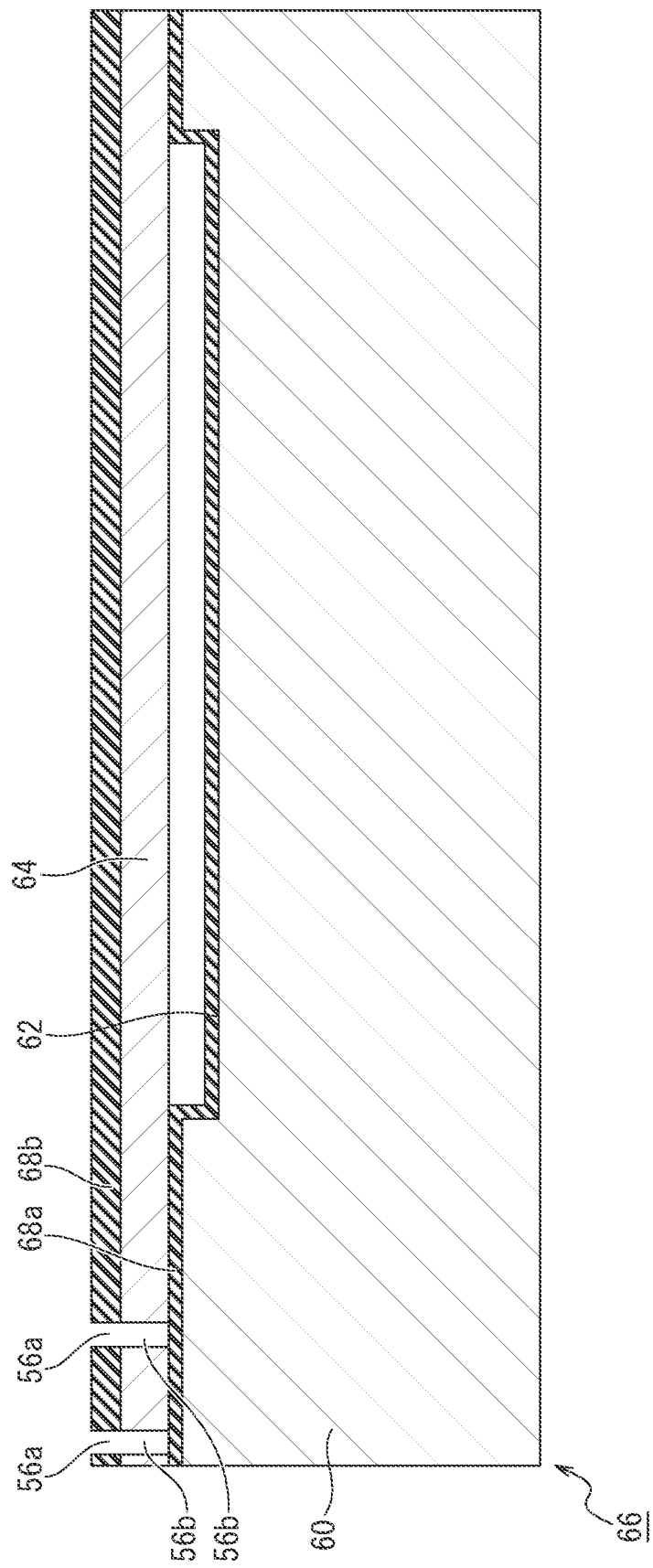

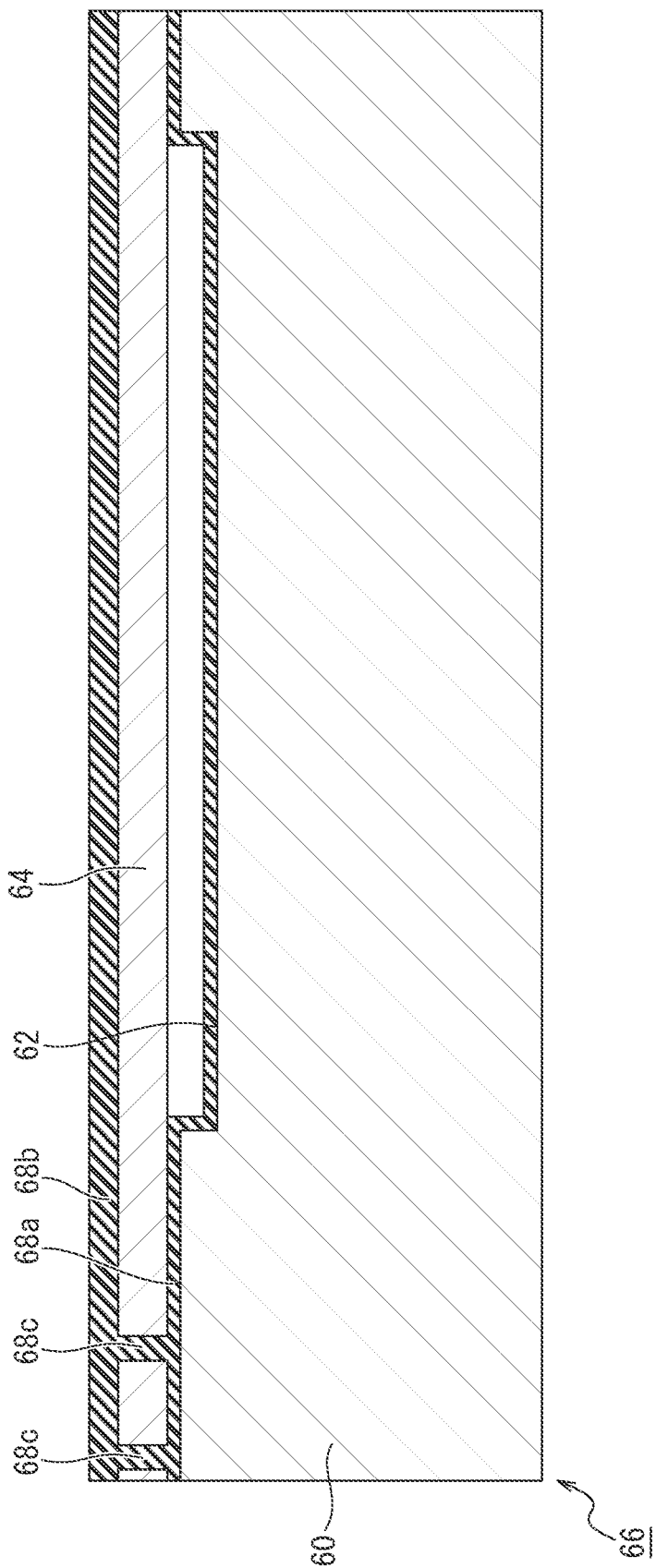

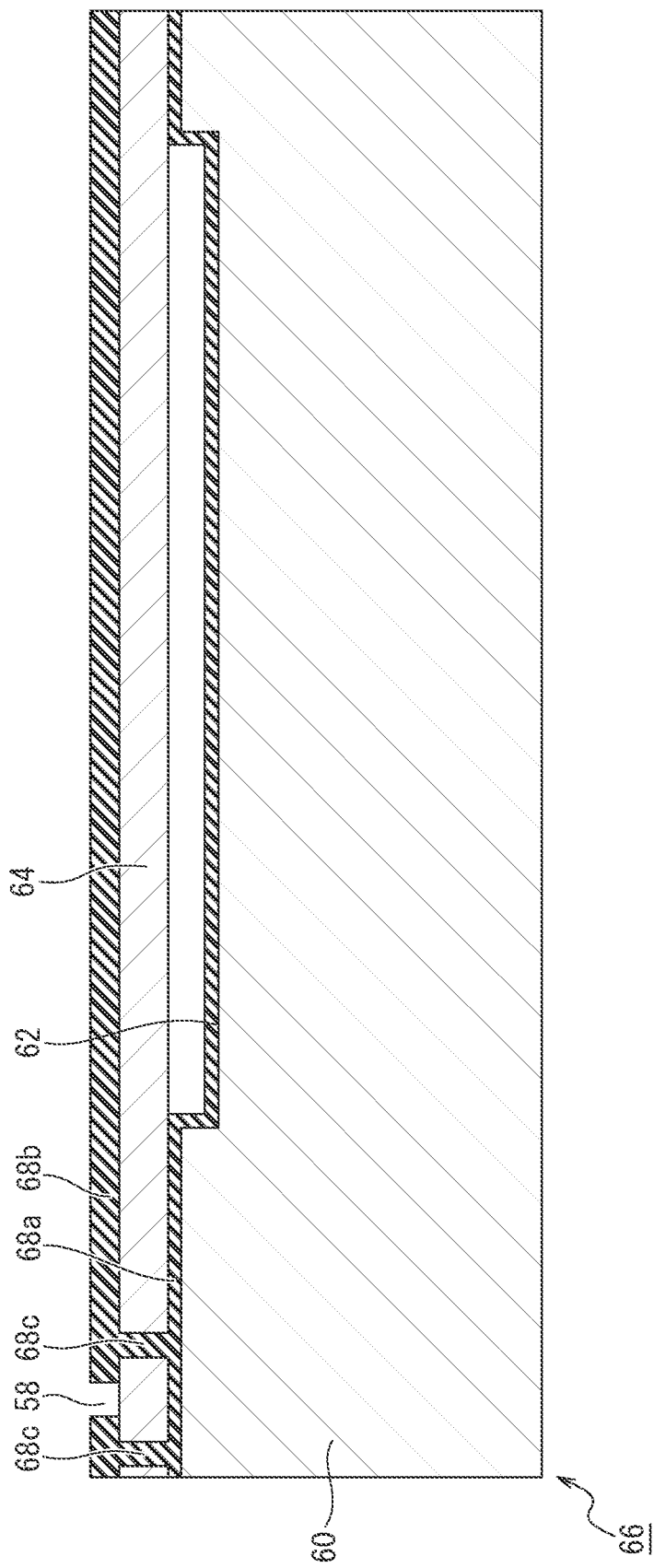

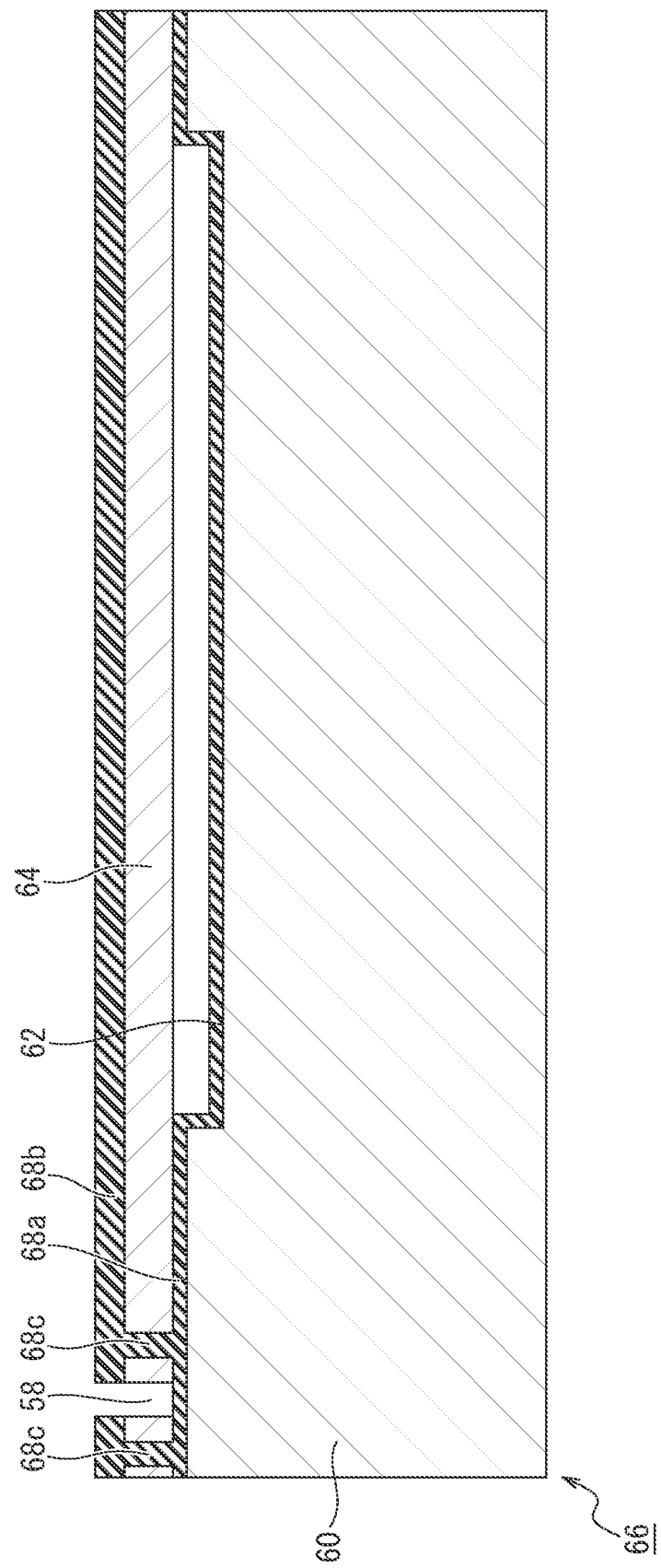

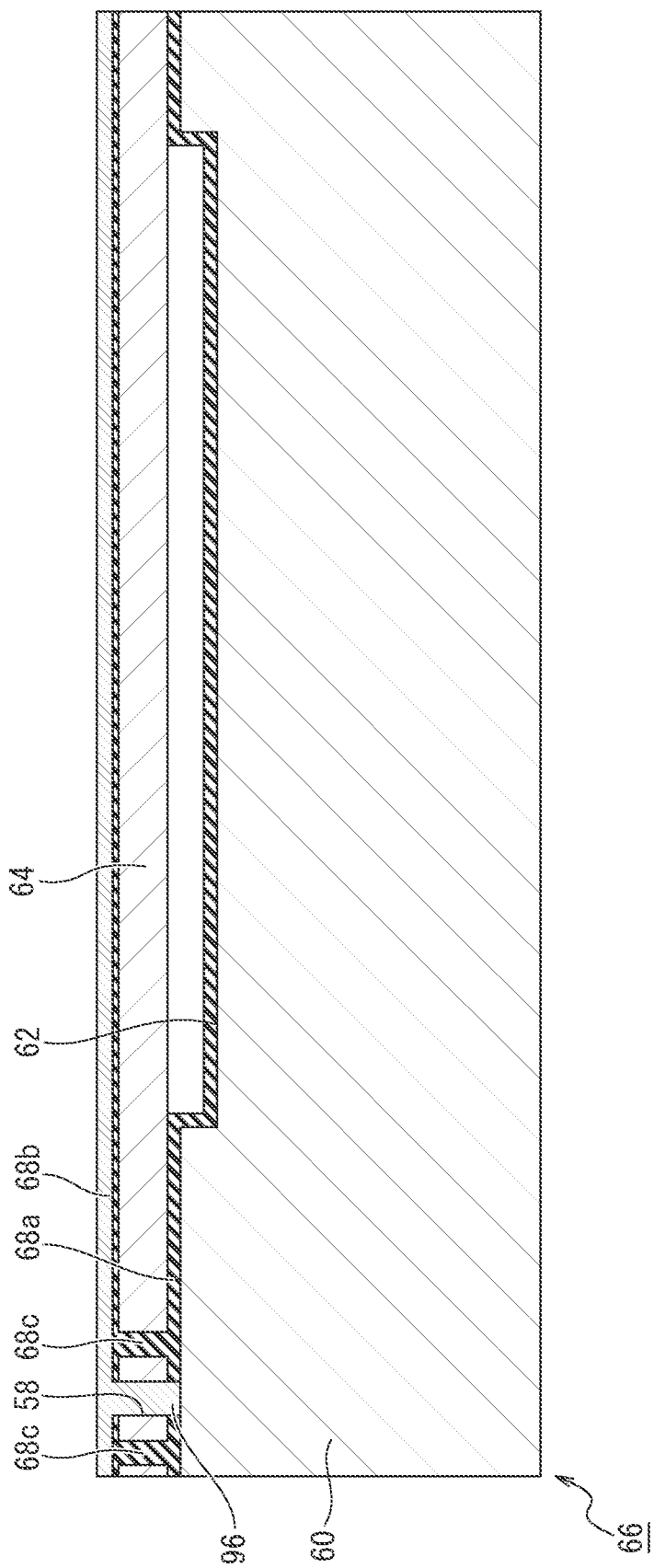

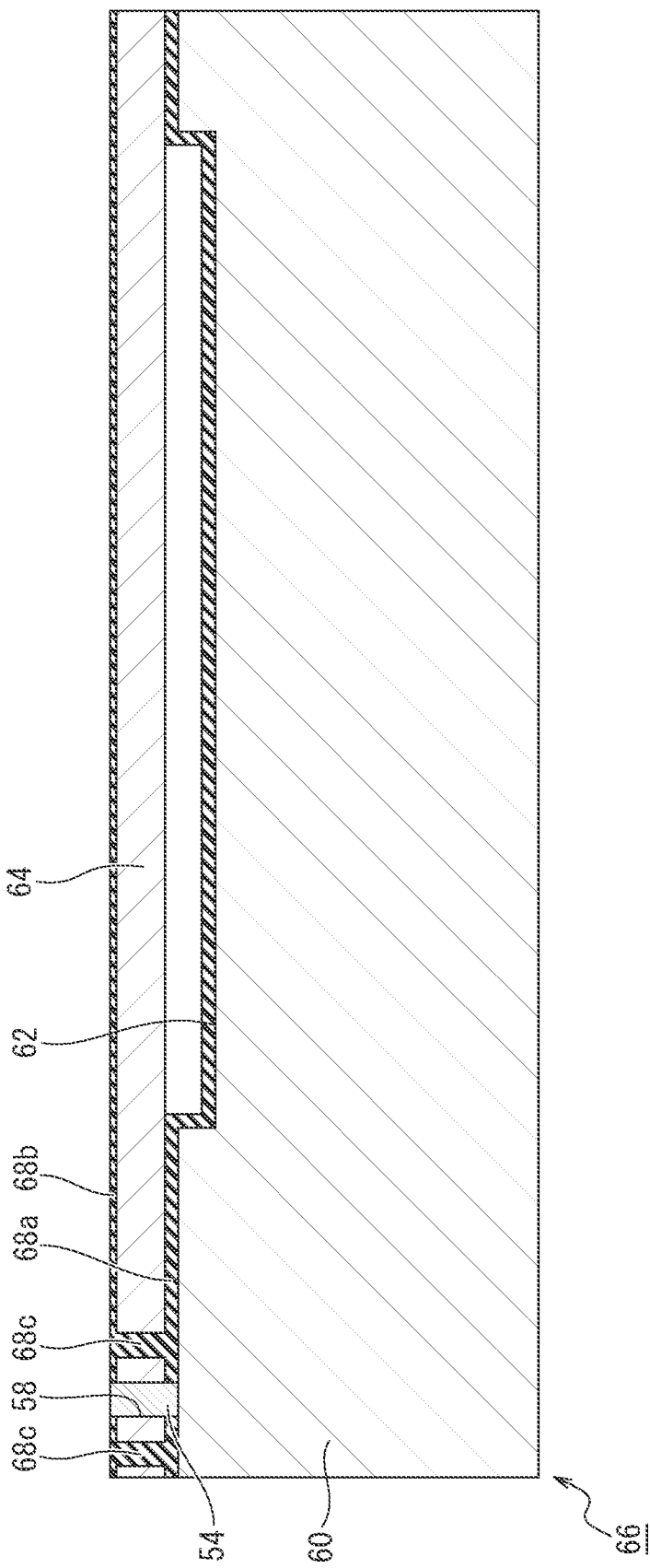

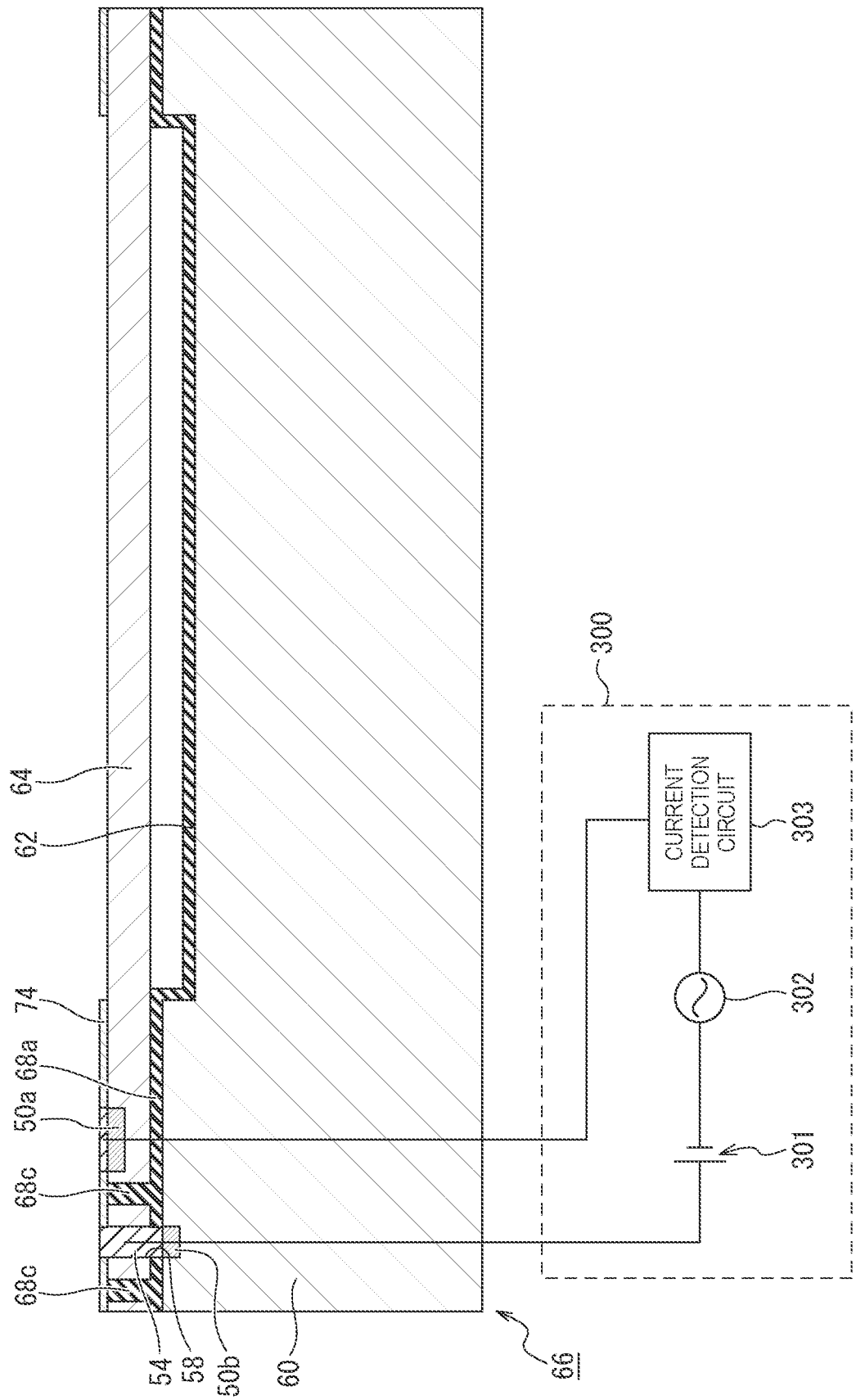

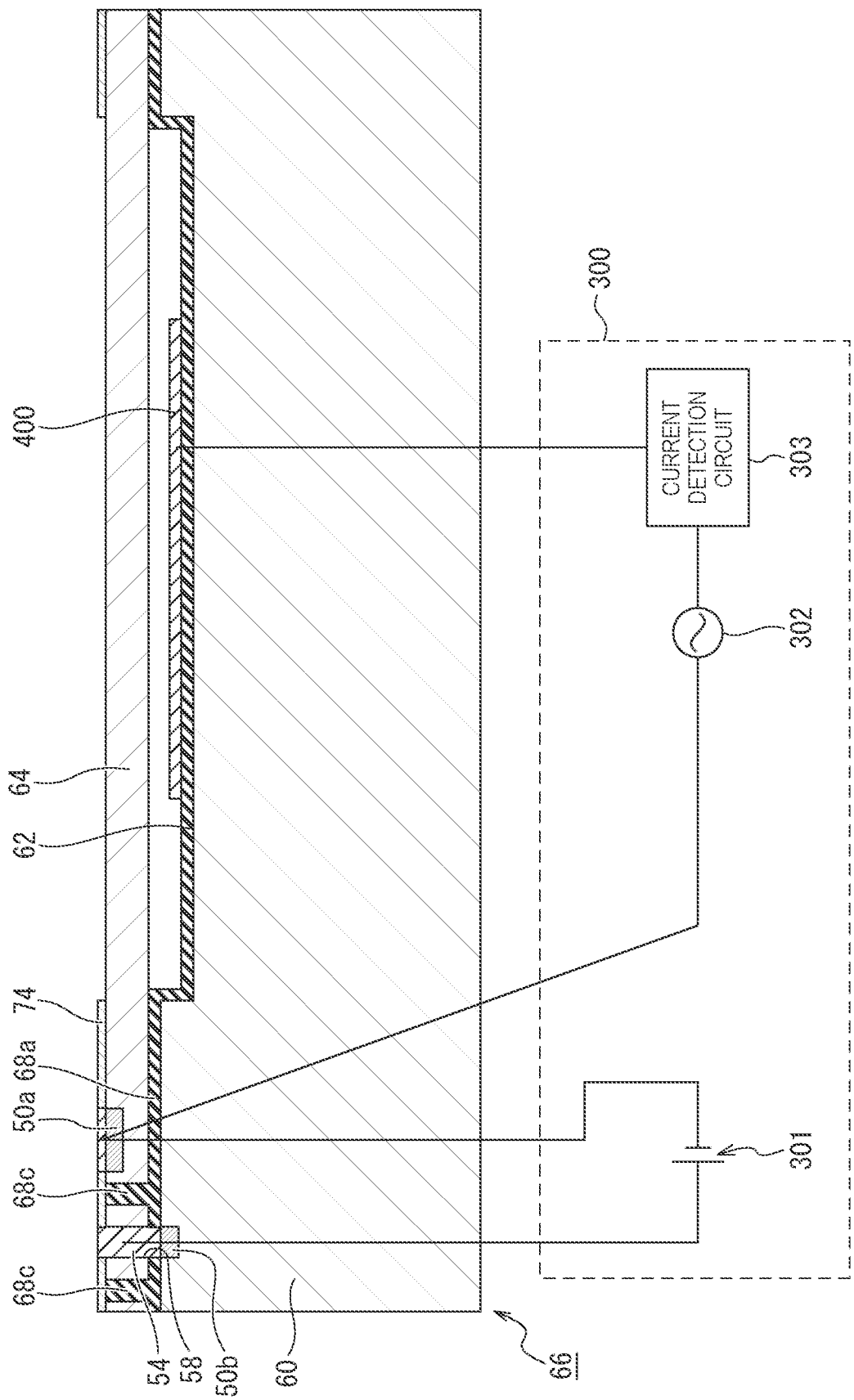

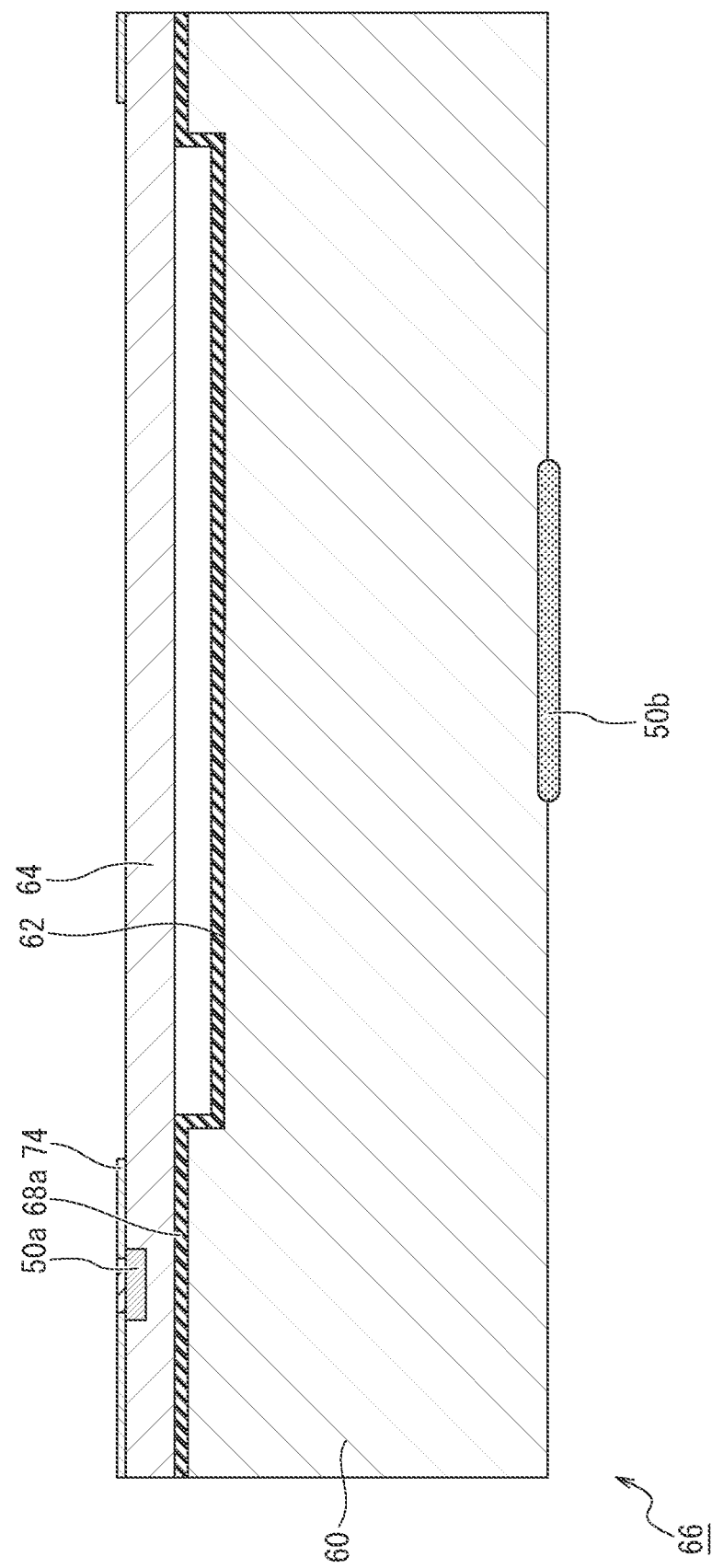

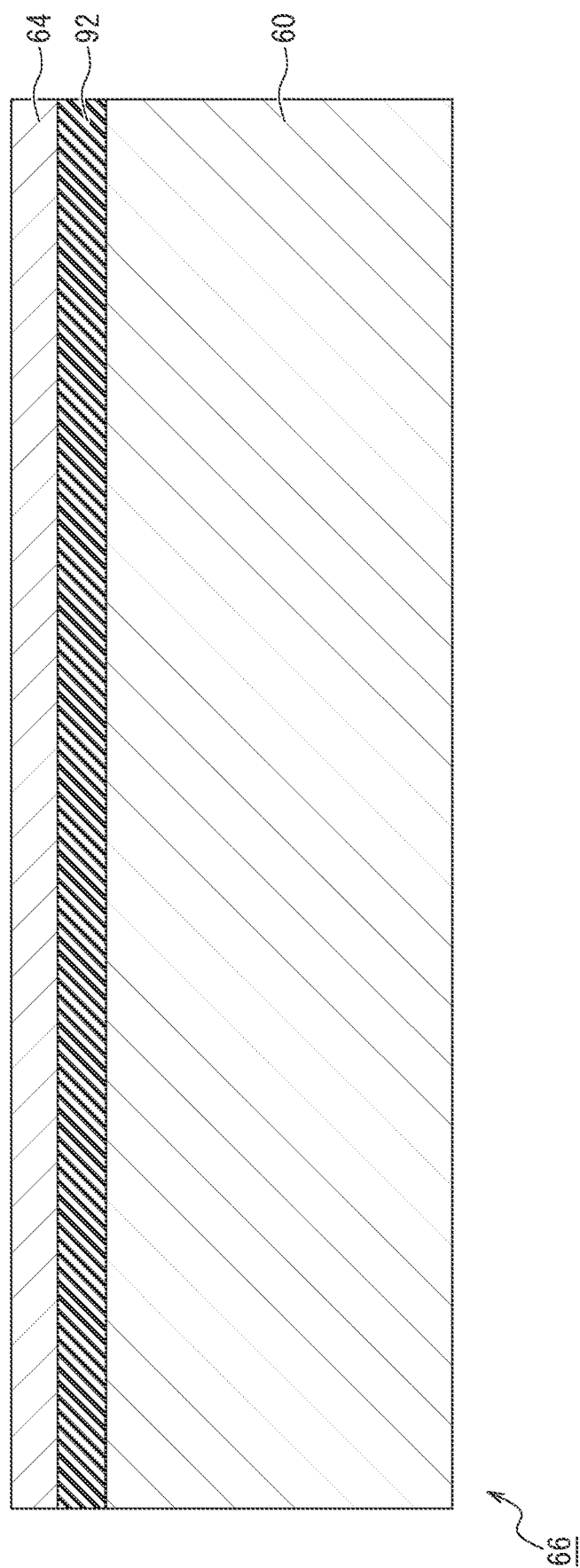

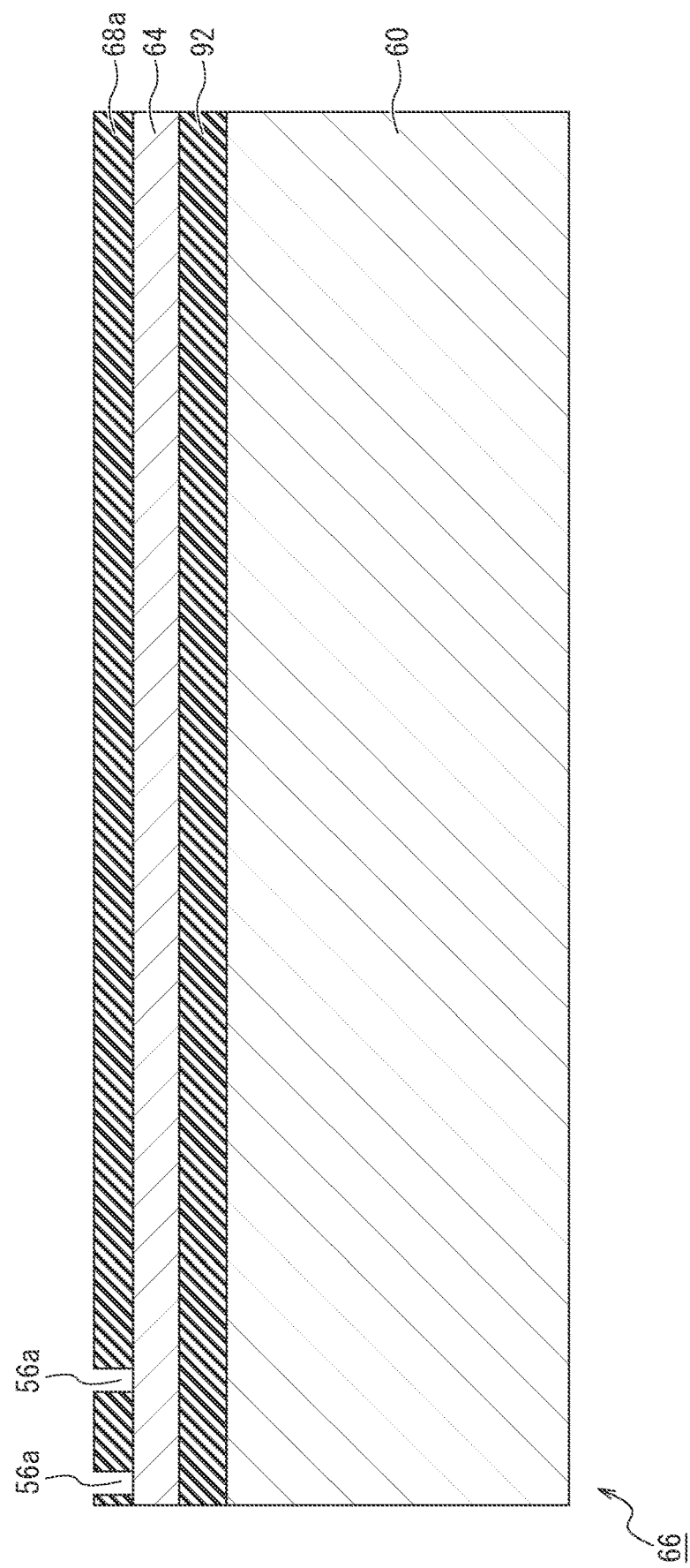

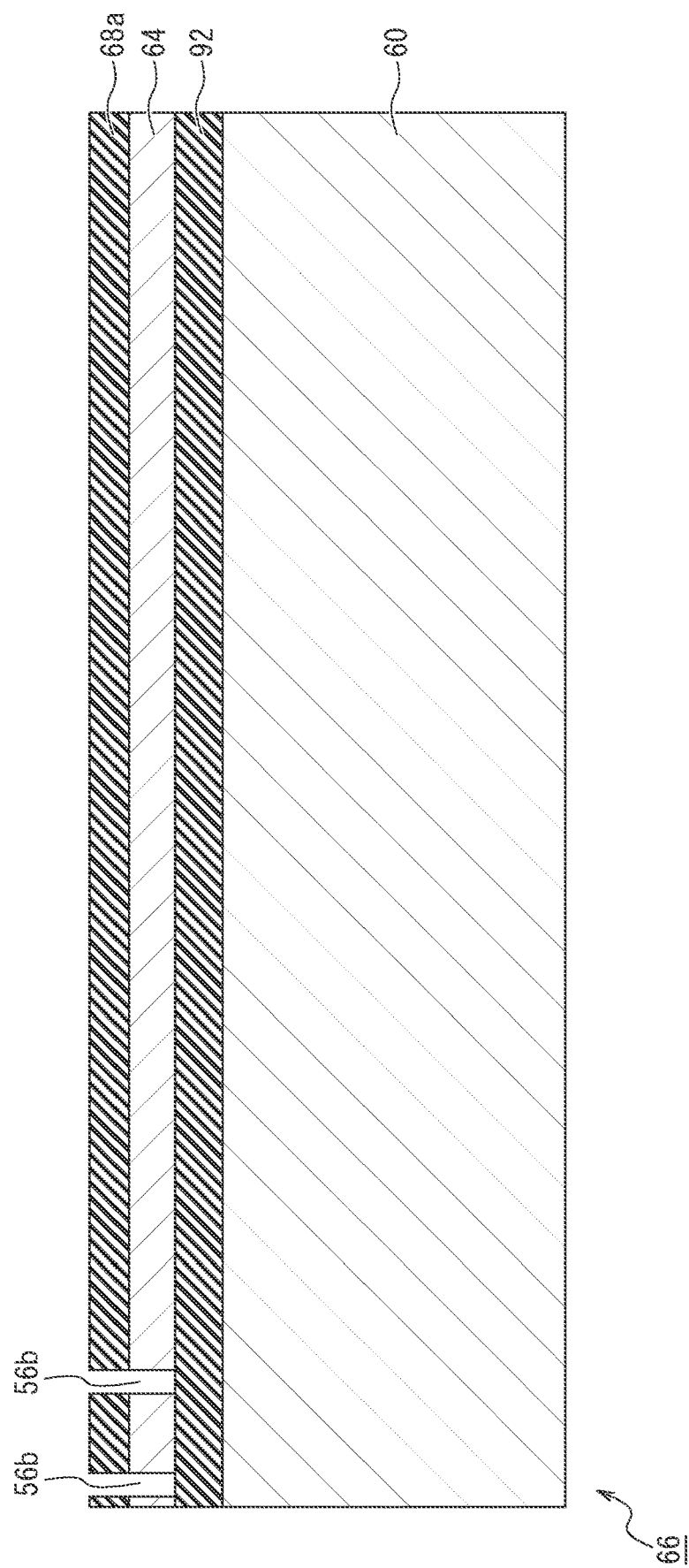

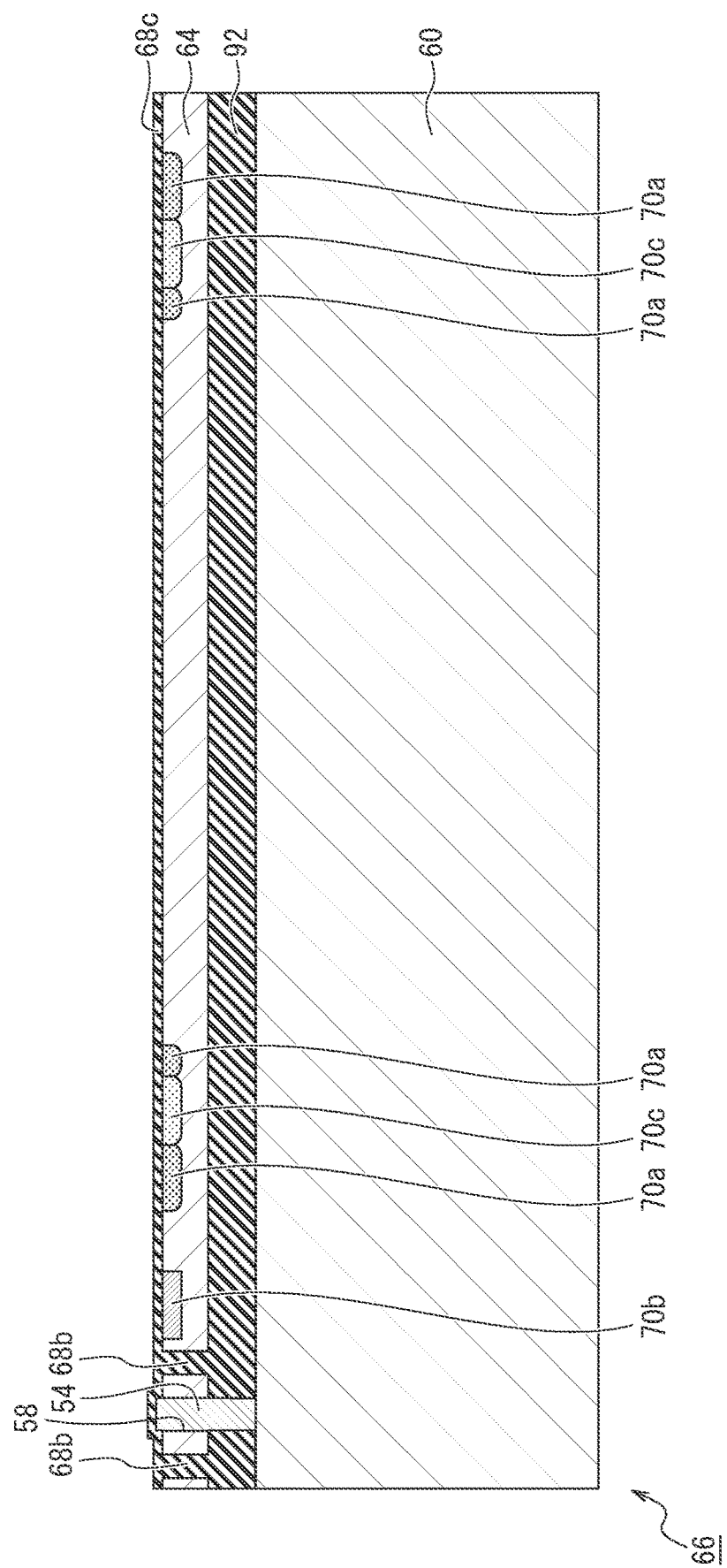

FIG. 53

| COATING POSITION | FLEXIBLE RESISTOR 28a | FLEXIBLE RESISTOR 28b | FLEXIBLE RESISTOR 28c | FLEXIBLE RESISTOR 28d | VOLTAGE VARIATION |
|---|---|---|---|---|---|
| CENTER | $-\Delta R$ | $-\Delta R$ | $+\Delta R$ | $+\Delta R$ | EQUAL |
| OFF TO THE RIGHT | $-\Delta R$ | $-\Delta R$ | $+\Delta R^-$ | $+\Delta R^+$ | DIFFERENT |
| OFF TO THE LEFT | $-\Delta R$ | $-\Delta R$ | $+\Delta R^+$ | $+\Delta R^-$ | DIFFERENT |
| OFF TO THE BOTTOM | $-\Delta R^-$ | $-\Delta R^+$ | $+\Delta R$ | $+\Delta R$ | DIFFERENT |
| OFF TO THE TOP | $-\Delta R^+$ | $-\Delta R^-$ | $+\Delta R$ | $+\Delta R$ | DIFFERENT |

GAS SENSOR, COMPONENT DETECTION APPARATUS INCLUDING GAS SENSOR, INSPECTION SYSTEM INCLUDING GAS SENSOR, GAS SENSOR INSPECTION METHOD, AND GAS SENSOR MANUFACTURING METHOD

TECHNICAL FIELD

The present invention relates to a membrane-type gas sensor with improved inspectability compared to conventional piezoresistive cantilever-type gas sensors, a component detection apparatus with a gas sensor, an inspection system with a gas sensor, a gas sensor inspection method, and a gas sensor manufacturing method.

BACKGROUND ART

As a technology used for sensors that collect information corresponding to the five human senses, especially for sensors for taste and smell, which humans sense by accepting chemical substances, there is, for example, a piezoresistive membrane-type gas sensor as disclosed in PTL 1. The piezoresistive membrane-type gas sensor disclosed in PTL 1 is a gas sensor that detects a stress generated from a receptor, which distorts when adsorbing a fluid (gas) containing a measurement target, based on resistance value variation of the piezoresistance. In the piezoresistive membrane-type gas sensor disclosed in PTL 1, the resistance value variation of a piezoresistance is detected using a change in voltage detected by a full bridge circuit (full Wheatstone bridge) formed from four resistances.

CITATION LIST

Patent Literature

Patent Literature 1: JP 2015-45657 A

SUMMARY OF INVENTION

Technical Problem

However, the gas sensor disclosed in PTL 1 involves a problem that it is difficult to detect a fault that may occur during manufacturing, assembly, or use, without applying a fluid containing a measurement target or a mechanical stress. The present invention was made by focusing on the conventional unsolved problem, and aims to provide a gas sensor capable of detecting a fault without requiring adhesion of a fluid containing a measurement target to a receptor or application of a mechanical stress, a component detection apparatus and an inspection system including such a gas sensor, a gas sensor inspection method, and a gas sensor manufacturing method.

Solution to Problem

To achieve the above aim, a gas sensor according to an aspect of the present invention includes a membrane, a fixing member, at least one pair of coupling portions, a flexible resistor, a support substrate, a receptor, a first terminal, a second terminal, and an insulating portion. The membrane is electrically conductive and bends with an applied surface stress. The fixing member is placed outside the membrane. The coupling portions are located at least at two positions sandwiching the membrane when viewed from the thickness direction of the membrane to couple the membrane to the fixing member. The flexible resistor varies its resistance value in accordance with a deflection that occurs in the coupling portions. The support substrate is electrically conductive, connected to the fixing member, and placed with a gap between the membrane and the coupling portions. The receptor is formed on an area that includes the center of a surface on one side of the membrane, which is opposite to the other side facing the support substrate, and deforms in accordance with on a substances adsorbed thereon. The first terminal is capable of applying a first potential to the membrane. The second terminal is capable of applying a second potential to the support substrate. The insulating portion electrically insulates the fixing member from the support substrate.

A component detection apparatus including a gas sensor according to another aspect of the invention includes a resistance detection unit, a pattern storage unit, and a component detector. The resistance detection unit detects an inspection-time resistance value, which is a resistance value of the flexible resistor in the state where a voltage is applied between the first and second terminals. The pattern storage unit stores a response pattern with which the receptor responds for a component contained in a fluid when the fluid adheres to the receptor. The component detector detects the component contained in the fluid adhered to the receptor in accordance with the inspection-time resistance value detected by the resistance detection unit and the response pattern stored in the pattern storage unit.

An inspection system including a gas sensor according to another aspect of the invention includes a voltage application unit and a resistance detection unit. The voltage application unit is capable of applying a voltage between the first and second terminals. The resistance detection unit detects an inspection-time resistance value, which is the resistance value of the flexible resistor in the state where a voltage is applied between the first and second terminals.

A gas sensor inspection method according to another aspect of the present invention, which is an inspection method of inspecting the operation of the membrane for a gas sensor, includes a second voltage application step, an inspection-time resistance detection step, and a determination step. The second voltage application step is a step for applying a second voltage between the first and second terminals. The inspection-time resistance detection step is a step for detecting an inspection-time resistance value, which is the resistance value of the flexible resistor in the state where the second voltage is applied between the first and second terminals. The determination step is a step for making a determination on the operation of the membrane, based on the inspection-time resistance value detected in the inspection-time resistance detection step and a reference resistance value which is a resistance value in the state where a first voltage different from the second voltage is applied between the first and second terminals.

A gas sensor inspection method according to another aspect of the present invention, which is an inspection method of inspecting the physical property of the receptor for a gas sensor, includes a second voltage application step, an inspection-time resistance detection step, a resonance frequency calculation step, and a receptor property discrimination step. The second voltage application step is a step for applying a second voltage between the first and second terminals. The inspection-time resistance detection step is a step for detecting an inspection-time resistance value, which is the resistance value of the flexible resistor in the state where the second voltage is applied between the first and second terminals. The resonance frequency calculation step is a step for calculating a resonance frequency of the gas sensor from the inspection-time resistance value detected in the inspection-time resistance detection step. The receptor property discrimination step is a step for discriminating the physical property of the receptor based on a comparison between a reference value of the resonance frequency and the resonance frequency calculated in the resonance frequency calculation step.

A gas sensor inspection method according to another aspect of the present invention, which is a method of inspecting a coating position of the receptor for a gas sensor, includes a bridge voltage application step, and a coating position discrimination step. The bridge voltage application step is a step for applying a bridge voltage to a bridge circuit constituted from flexible resistors. The coating position discrimination step is a step for discriminating a coating position of the receptor from an output value of the bridge circuit in the state where a first voltage is applied between the first and second terminals, and an output value of the bridge circuit in the state where a second voltage different from the first voltage is applied between the first and second terminals.

A gas sensor manufacturing method according to another aspect of the present invention includes a laminate formation step, a through-electrode formation step, a first ion implantation step, a second ion implantation step, a third ion implantation step, a low-resistance area formation step, a removal step, and a wiring layer formation step. The laminate formation step is a step for forming a recess on one side of the support substrate, forming an insulating portion on the one side, and then laminating a detection substrate so as to cover a part of the support substrate where the insulating portion has been formed, so that a laminate with a gap between the support substrate and the detection substrate is formed. The through-electrode formation step is a step for removing a part of the detection substrate and the insulating portion to thereby form a through-hole that penetrates from a surface on one side of the detection substrate, which is opposite to the other side facing the support substrate, to the support substrate, and then forming a through-electrode that reaches from the surface to the support substrate by burying the through-hole with an electrode material containing impurities. The first ion implantation step is a step for implanting first ions into a selected area of the surface of the detection substrate, which is outside a preset area including the center of the detection substrate. The second ion implantation step is a step for implanting second ions into a selected area which is outside the area of the detection substrate where the first ions have been implanted. The third ion implantation step is a step for implanting third ions into a preset area of the surface of the detection substrate. The low-resistance area formation step is a step for forming, by heat-treating the laminate, a first low-resistance area within the area where the first ions have been implanted, a second low-resistance area within the area where the second ions have been implanted, and a third low-resistance area within the area where the third ions have been implanted. In addition, the low-resistance area formation step is a step for forming a fourth low-resistance area within a preset area in the side of the support substrate, which is opposed to the detection substrate, by solid-phase diffusing impurities from the through-electrode into the support substrate. The removal step is a step for forming, by removing an area which is around the preset area including the center of the detection substrate and excluding the first low-resistance area, a membrane that bends with an applied surface stress, a fixing member that surrounds the membrane with a gap when viewed from the thickness direction of the membrane, and at least one pair of coupling portions that are placed at least at two positions sandwiching the membrane when viewed from the thickness direction and couple the membrane and the fixing member together. The wiring layer formation step is a step for forming a wiring layer that includes a first terminal electrically connected to the membrane and a second terminal electrically connected to the support substrate.

Here, the "preset area including the center of the detection substrate" is an area that later becomes the membrane, the "first low-resistance area" is an area that later becomes the coupling portions, and the "second low-resistance area" is an area that later becomes the first terminal. Also, the "third low-resistance area" is an area that later becomes the flexible resistor, and the "fourth low-resistance area" is an area that later becomes the second terminal.

Advantageous Effects of Invention

According to one aspect of the invention, the membrane can be deformed by the Coulomb force generated by applying electric potentials to the first and second terminals. Therefore, by measuring a resistance value variation that occurs when the membrane is deformed, it is possible to detect a fault without requiring adhesion of a fluid containing a target measurement to the receptor or application of mechanical stress.

This makes it possible to provide a gas sensor capable of detecting a fault without applying a fluid containing a target measurement or a mechanical stress, a component detection apparatus and inspection system including the gas sensor, an inspection method for the gas sensor, and a manufacturing method for the gas sensor.

BRIEF DESCRIPTION OF DRAWINGS

FIG. 16C is a diagram illustrating the laminate formation step;
FIG. 16D is a diagram illustrating the laminate formation step;
FIG. 17A is a diagram illustrating a through-electrode formation step;
FIG. 17B is a diagram illustrating the through-electrode formation step;
FIG. 17C is a diagram illustrating the through-electrode formation step;
FIG. 18A is a diagram illustrating the through-electrode formation step;
FIG. 18B is a diagram illustrating the through-electrode formation step;
FIG. 18C is a diagram illustrating the through-electrode formation step;
FIG. 19B is a diagram illustrating the through-electrode formation step;
FIG. 19C is a diagram illustrating the through-electrode formation step;
FIG. 28 is a diagram illustrating a variation of the first embodiment;
FIG. 29 is a diagram illustrating a variation of the first embodiment;
FIG. 30 is a diagram illustrating a variation of the first embodiment;
FIG. 31 is a diagram illustrating a laminate formation step;
FIG. 32B is a diagram illustrating the through-electrode formation step;
FIG. 32C is a diagram illustrating the through-electrode formation step;
FIG. 35 is a diagram illustrating a first ion implantation step, a second ion implantation step, and a third ion implantation step;
FIG. 53 is a diagram illustrating a relationship that holds in the coating position of the receptor, resistance value variations of four flexible resistors, and variations of voltages outputted from third and fourth terminals and variations of voltages outputted from fifth and sixth terminals.

DESCRIPTION OF EMBODIMENTS

Figure 1:
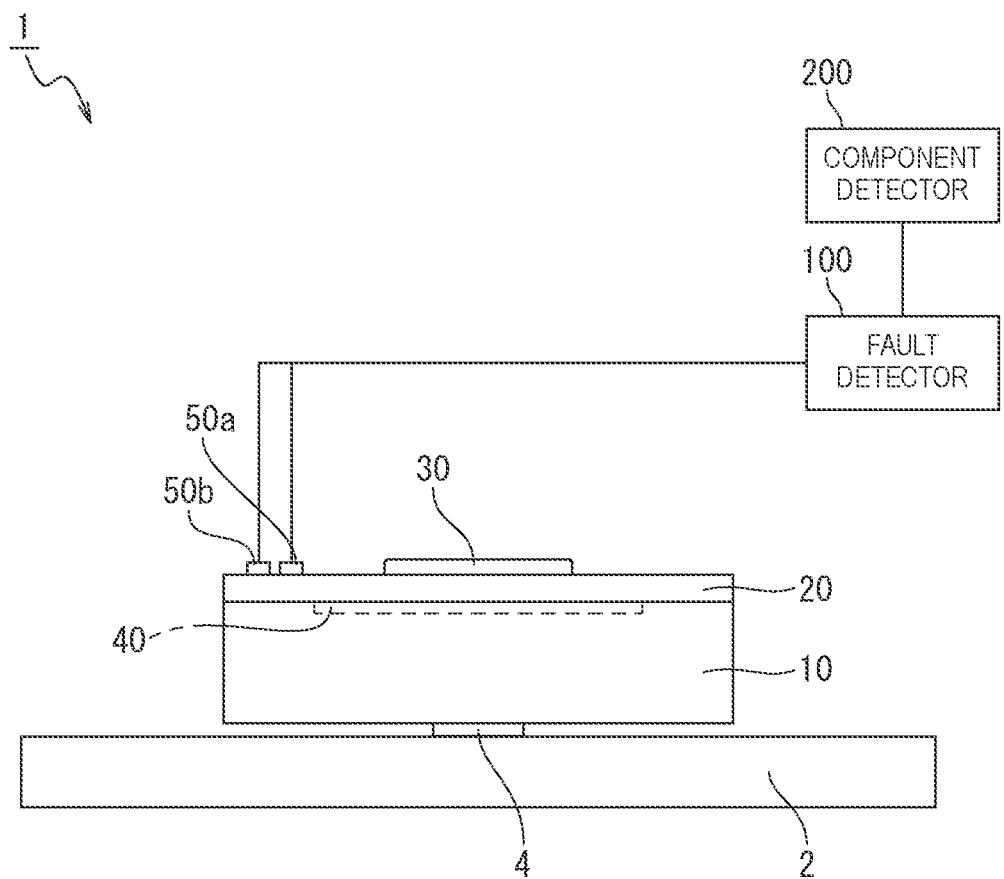
FIG. 1 is a side view illustrating a configuration of a gas sensor according to a first embodiment of the present invention.

Embodiments of the present invention are explained below with reference to the drawings. In the description of the drawings referred to in the following explanation, the same or similar parts are marked with the same or similar signs. However, it should be noted that the drawings are schematic, and the relationship between thicknesses and plane dimensions, thickness ratios, etc., may differ from reality. Therefore, specific thickness and dimensions should be determined by referring to the following explanation. In addition, it is of course possible that some parts of the drawings have different dimensional relationships and proportions to each other.

Furthermore, the following embodiments are examples of configurations for embodying the technical idea of the present invention, and the technical idea of the present invention does not specify materials of constituent components, their shapes, structures, and arrangements, etc., to the following ones. The technical idea of the present invention can be modified in various ways within the technical scope defined by the patent claims. The directions of "left and right" or "up and down" in the following description are merely definitions for convenience of explanation, and do not restrict the technical concept of the present invention. Accordingly, for example, if the paper is rotated 90 degrees, "left and right" and "up and down" are read interchangeably, and if the paper is rotated 180 degrees, "left" becomes "right" and "right" becomes "left," of course.

First Embodiment

A first embodiment of the present invention is explained below with reference to the drawings.
(Configuration)
FIGS. 1 to 7 illustrate a configuration of the first embodiment. A gas sensor 1 illustrated in FIGS. 1 to 5 is a sensor used, for example, for sensing olfactory. The gas sensor 1 includes a package substrate 2, a connecting portion 4, a support substrate 10, a detection substrate 20, an insulating portion 6, a first terminal 50a, a second terminal 50b, a third terminal 50c, a fourth terminal 50d, a fifth terminal 50e, a sixth terminal 50f, a through-electrode 54, a fault detector 100, and a component detector 200. In FIG. 2, the package substrate 2, the connecting portion 4, the fault detector 100, the component detector 200, and wiring are omitted for the sake of explanation.
(Package Substrate)
The package substrate 2 is formed using, for example, metal, polymer, ceramic material, or the like, with a thickness on the order of millimeters, for example.
(Connecting Portion)
The connecting portion 4 is located on one side of the package substrate 2 (the upper side in FIG. 1) and is formed using, for example, adhesives or solder. As an example, the first embodiment is explained for the case where the connecting portion 4 is formed into a circular shape.
(Support Substrate)
The support substrate 10 is electrically conductive and serves as a fixed electrode of the gas sensor 1. The support substrate 10 is placed on one side of the package substrate 2 and is attached to the package substrate 2 via the connecting portion 4. As an example, the first embodiment is explained for the case where the center of the support substrate 10 overlaps with the position at which the connecting portion 4 is placed. The area of the support substrate 10 (in FIG. 1, the area of the support substrate 10 viewed from the vertical direction) is larger than the area of the connecting portion 4. The thickness of the support substrate 10 (in FIG. 1, the length of the support substrate 10 in the vertical direction) is set to 80 [μm] or more. The thickness of the support substrate 10 may be set within the range from 80 [μm] to 750 [μm]. For example, a material containing any one of silicon (Si), sapphire, gallium arsenide, glass, or quartz may be used to form the support substrate 10.

As an example, the first embodiment is explained for the case where N type silicon is used as a material to form the support substrate 10. N type silicon is single crystal silicon to which pentavalent elements such as arsenic, phosphorus, and antimony are added as impurities. Accordingly, in the first embodiment, the coefficient of linear expansion of the support substrate 10 is $5.0 \times 10^{-6}/°$ C. or less. The coefficients of linear expansion of materials that can be used to form the support substrate 10 are described below.

The coefficient of linear expansion of silicon is $3.9 \times 10^{-6}/°$ C. or less in the environment of room temperatures to 1000° C. The coefficient of linear expansion of sapphire is $9.0 \times 10^{-6}/°$ C. or less in the environment of 0° C. to 1000° C. The coefficient of linear expansion of gallium arsenide (GaAs) is $6.0 \times 10^{-6}/°$ C. or less in the environment of OK to 300K. The coefficient of linear expansion of glass (float glass) is $8.5 \times 10^{-6}/°$ C. or less to $9.0 \times 10^{-6}/°$ C. or less in the environment of 0° C. to 300° C. The coefficient of linear expansion of quartz is $0.59 \times 10^{-6}/°$ C. or less in the environment of 0° C. to 300° C. Incidentally, the coefficient of linear expansion of quartz peaks at around 300° C.
(Detection Substrate)
The detection substrate 20 is electrically conductive and serves as a movable electrode of the gas sensor 1. The detection substrate 20 is laminated on one side (the upper side in FIG. 1) of the support substrate 10, and the membrane 22, the fixing member 24, and the coupling portions 26 are integrally formed. As an example, the first embodiment is explained for the case where N type silicon is used as a material to form the detection substrate 20. A material to form the detection substrate 20 is selected so that the difference between the coefficient of linear expansion of the support substrate 10 and the coefficient of linear expansion of the detection substrate 20 is $1.2 \times 10^{-5}/°$ C. or less. The first embodiment is explained for the case where the material to form the detection substrate 20 and the material to form the support substrate 10 are the same.
(Membrane)
The membrane 22 is electrically conductive and is formed in a plate shape. As an example, the first embodiment is described for the case where the membrane 22 is formed in a disk shape. The membrane 22 may be formed in a polygonal shape or a shape surrounded by curves, for example. The membrane 22 is an N type semiconductor layer. One side of the membrane 22 (the upper side in FIG. 1) is coated with a receptor 30. In the following description, the one side of the membrane 22 may be referred to as "the surface of the membrane 22".

The receptor 30 is formed on top of a receptor-forming area. The receptor-forming area is an area including the center of the surface of the membrane 22, and is set in advance. Since the area coated with the receptor 30 should be wide enough, the receptor-forming area should be wide enough. The receptor 30 is formed, for example, by coating and drying a solution in which a resin such as polyethyleneimine (PEI) is dissolved (may be referred to as "PEI solution" in the following description), and a strain is occurred when the molecules of a target measurement (gas) are adsorbed. As the solution to dissolve the receptor, there are no particular limitations as long as the receptor can be dissolved, and general organic solvents or water may be used. When the molecules of the measurement target are adsorbed on the receptor 30 and a strain is occurred in the receptor 30, a surface stress is applied to the membrane 22, causing the membrane 22 to bend. Therefore, the membrane 22 bends with the applied surface stress as the gas molecules are adsorbed on the receptor 30.

(Fixing Member)

The fixing member 24 is electrically conductive, and is located outside the center of the membrane 22. The fixing member 24 is formed in the shape of a quadrilateral (square) frame, and surrounds the membrane 22 with a gap when viewed from the thickness direction of the membrane 22. That is, the fixing member 24 is separated from the membrane 22 when viewed from the thickness direction of the membrane 22. The view in the thickness direction of the membrane 22 is a view of the gas sensor 1 from above (in FIG. 1, in the direction of arrow II). The center of the fixing member 24 overlaps with the center of the membrane 22 when viewed from the thickness direction of the membrane 22.

The fixing member 24 is placed on one side of the support substrate 10 opposite to the other side facing the package substrate 2 (the upper side in FIG. 1) with the insulating portion 6 in between. As an example, the first embodiment is explained for the case where the fixing member 24 and the support substrate 10 are formed into such shapes that the outer peripheral surface of the support substrate 10 and the outer peripheral surface of the fixing member 24 are flush with each other when viewed from the thickness direction of the membrane 22. That is, the fixing member 24 and the support substrate 10 are quadrilaterals of the same shape when viewed from the thickness direction of the membrane 22. This is achieved, for example, by performing a dicing process on the fixing member 24 and the support substrate 10 after connecting the fixing member 24 and the support substrate 10 together. That is, the center of the fixing member 24 overlaps the center of the support substrate 10 when viewed from the thickness direction of the membrane 22.

Accordingly, the support substrate 10 overlaps with the membrane 22 and the fixing member 24 when viewed from the thickness direction of the membrane 22. In addition, the connecting portion 4 is located at a position where it overlaps with at least a part of the membrane 22 when viewed from the thickness direction of the membrane 22. The area of the connecting portion 4 is smaller than the area of the membrane 22 when viewed from the thickness direction of the membrane 22. The package substrate 2 is connected to one side of the support substrate 10, which is opposite to the other side facing the membrane 22 (the lower side in FIG. 1).

(Coupling Portion)

The coupling portions 26 are electrically conductive, and are formed in a strip shape when viewed from the thickness direction of the membrane 22. The coupling portions 26 are located at positions where they overlap with virtual straight line VL1 or VL2 passing through the center of the membrane 22 when viewed from the thickness direction of the membrane 22, and couples the membrane 22 and the fixing member 24 together. As an example, the first embodiment is explained for the case where the membrane 22 and the fixing member 24 are coupled together by four coupling portions 26a to 26d as two pairs. The four coupling portions 26a to 26d include a pair of coupling portions 26a and 26b located at positions overlapping with the straight line VL1, and a pair of coupling portions 26c and 26d located at positions overlapping with the straight line VL2 orthogonal to the straight line VL1.

That is, the pair of the coupling portions 26a and 26b, and the pair of the coupling portions 26c and 26d are located at least at two positions sandwiching the membrane 22 when viewed from the thickness direction of the membrane 22, and couple the membrane 22 and the fixing member 24 together. As an example, the first embodiment is explained for the case where the widths of the coupling portions 26a and 26b are narrower than the widths of the coupling portions 26c and 26d. A gap 40 is provided between the membrane 22, four coupling portions 26a to 26d and the support substrate 10.

Accordingly, the support substrate 10 is connected to the fixing member 24, and placed with a gap (gap 40) between the membrane 22 and the coupling portions 26. In addition to this, the support substrate 10 overlaps with the membrane 22 and the coupling portion 26 when viewed from the thickness direction of the membrane 22. When the gas sensor 1 is used in a solution, the gap 40 may be filled with the solution. The gap 40 serves as a space that prevents the membrane 22 from sticking to the support substrate 10 when the membrane 22 bends toward the support substrate 10 while the detection substrate 20 is processed. Also, the gap 40 serves as a space for forming a capacitance between the membrane 22, coupling portions 26 and the support substrate 10. The four coupling portions 26a to 26d are respectively provided with flexible resistors 28a to 28d.

(Flexible Resistors)

Figure 5:
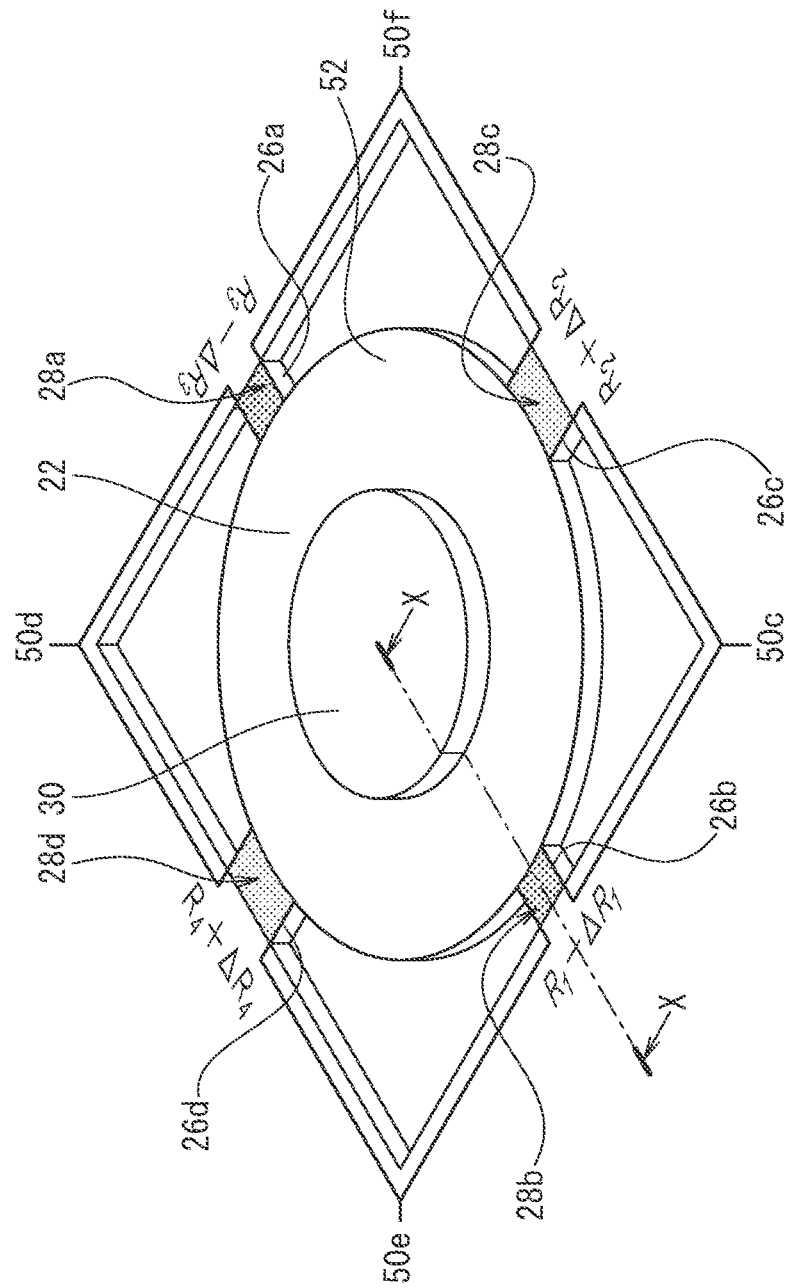
FIG. 5 is a perspective view of the gas sensor.

Each of the flexible resistors 28 varies its resistance value in accordance with a deflection occurred in the coupling portions 26. As an example, the first embodiment is explained for the case where the flexible resistors 28 are formed of piezoresistances. The piezoresistance are formed, for example, by implantation of ions into the coupling portions 26, and have resistance values that vary in accordance with a deflection occurred in the coupling portions 26 as the membrane 22 bends. The flexible resistors 28 are P type semiconductor layers. As illustrated in FIG. 5, the four flexible resistors 28a to 28d are arranged, for example, such that coadjacent flexible resistors 28 (the coupling portion 26a with regards to the coupling portions 26c, 26d, and the coupling portion 26b with regards to the coupling portions 26c, 26d) are connected to one another. Accordingly, the four flexible resistors 28a to 28d form a full Wheatstone bridge illustrated in FIG. 5.

(Insulating Portion)

The insulating portion 6 electrically insulates the support substrate 10 from the detection substrate 20. The insulating portion 6 is formed of a silicon oxide film provided between the support substrate 10 and the fixing member 24. A part of the insulating portion 6 surrounds the second terminal 50b when viewed from the thickness direction of the membrane 22. The insulating portion 6, except for the part surrounding the second terminal 50b when viewed from the thickness direction of the membrane 22, is located between the support substrate 10 and the fixing member 24.

(First Terminal)

The first terminal 50a is formed using a metal material such as Al, and is electrically connected to the membrane 22.

(Second Terminal)

The second terminal 50b is formed via the through-electrode 54 using a metal material such as Al, and is electrically connected to the support substrate 10.

(Third Terminal)

The third terminal 50c, which is formed using a metal material such as Al, is a terminal for detecting the resistance value of the flexible resistor. The first embodiment describes a configuration in which the third terminal 50c is electrically connected to the flexible resistor 28a and the flexible resistor 28d, as illustrated in FIG. 5.

(Fourth Terminal)

The fourth terminal 50d, which is formed using a metal material such as Al, is a terminal different from the third terminal, for detecting the resistance value of the flexible resistor. The first embodiment describes a configuration in which the fourth terminal 50*d* is electrically connected to the flexible resistor 28*b* and the flexible resistor 28*c*, as illustrated in FIG. 5.

(Fifth Terminal)

The fifth terminal 50*e*, which is formed using a metal material such as Al, is a terminal used for voltage application to detect the resistance value of the flexible resistor. The first embodiment describes a configuration in which the fifth terminal 50*e* is electrically connected to the flexible resistor 28*b* and the flexible resistor 28*d*, as illustrated in FIG. 5.

(Sixth Terminal)

The sixth terminal 50*f*, which is formed using a metal material such as Al, is a terminal different from the fifth terminal, for voltage application to detect the resistance value of the flexible resistor. The first embodiment describes a configuration in which the sixth terminal 50*f* is electrically connected to the flexible resistor 28*a* and the flexible resistor 28*c*, as illustrated in FIG. 5.

(Through-Electrode)

The through-electrode 54, which is formed using an electrode material containing impurities, is an electrode that reaches the support substrate 10 from the surface (the surface of the detection substrate 20) on the one side of the detection substrate 20, which is opposite to the other side facing the support substrate 10.

(Fault Detector)

Figure 6:
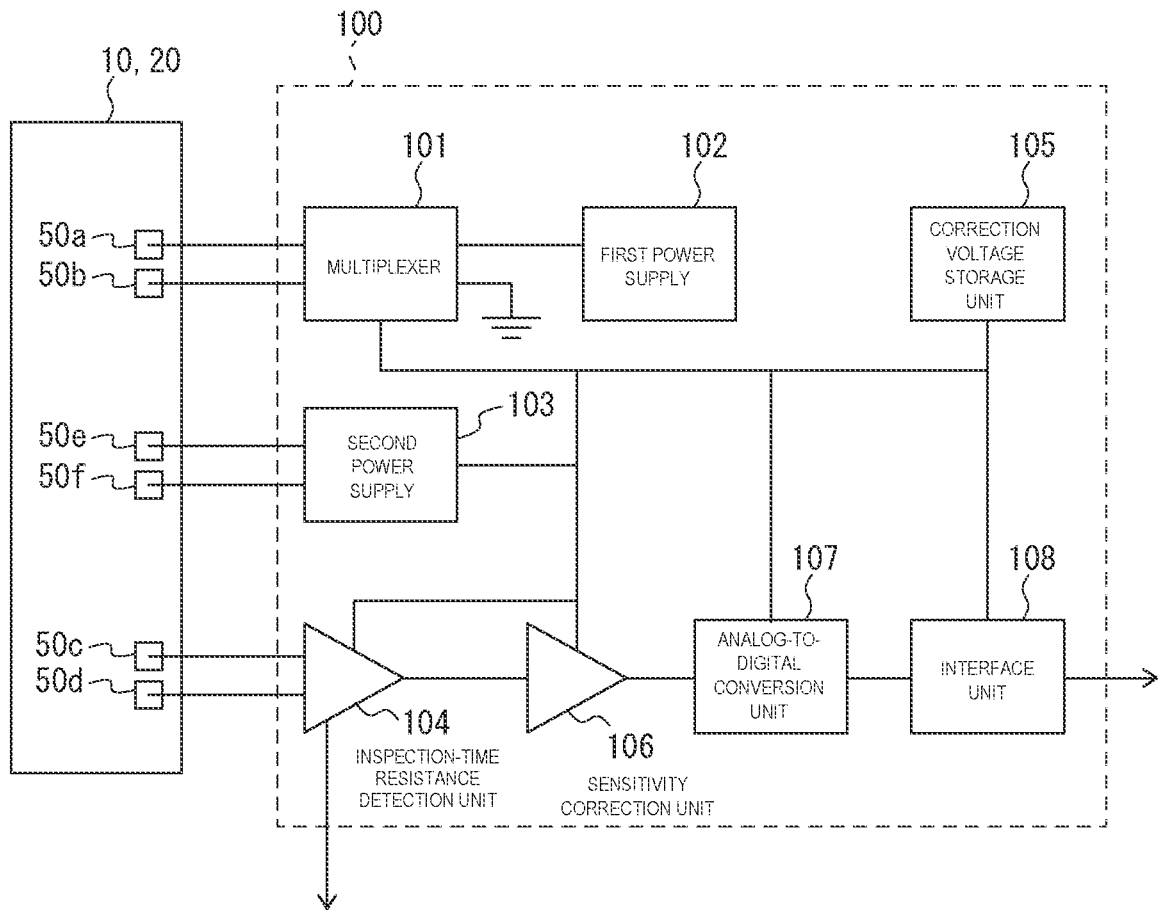
FIG. 6 is a diagram illustrating a configuration of a fault detector.

A detailed configuration of the fault detector 100 is explained below. The fault detector 100 detects a fault in the gas sensor 1 by applying a voltage between the support substrate 10 and a set of the membrane 22 and coupling portion 26 to thereby deform the membrane 22. The fault detector 100 includes a multiplexer 101, a first power supply 102, a second power supply 103, a resistance detection unit 104, a correction value storage unit 105, a sensitivity correction unit 106, an analog-to-digital conversion unit 107, and an interface unit 108, as illustrated in FIG. 6. The multiplexer 101, the first power supply 102, the second power supply 103, the resistance detection unit 104, the correction value storage unit 105, the sensitivity correction unit 106, the analog-to-digital conversion unit 107, and the interface unit 108 are mounted on an IC or a circuit board.

The multiplexer 101 connects at least one of the first terminal 50*a* and the second terminal 50*b* to the first power supply 102 in accordance with a received switching signal. The first power supply 102 is connected to the multiplexer 101. The first power supply 102, together with the multiplexer 101, forms a voltage application unit that can apply a voltage between the first and second terminals 50*a* and 50*b*. When a voltage is applied between the first and second terminals 50*a* and 50*b* by the voltage application unit (the first power supply 102, the multiplexer 101), the membrane 22 deforms in accordance with the voltage applied between the first and second terminals 50*a* and 50*b*.

When a voltage is applied between the first terminal 50*a* and the second terminal 50*b* by the voltage application unit, a first potential according to the applied voltage can be applied to the membrane 22. Similarly, when a voltage is applied between the first terminal 50*a* and the second terminal 50*b* by the voltage application unit, a second potential according to the applied voltage can be applied to the support substrate 10. The first potential and the second potential may be the same or different values. The second power supply 103 is connected to the fifth terminal 50*e* and the sixth terminal 50*f*, and can apply a voltage between the fifth terminal 50*e* and the sixth terminal 50*f*.

The resistance detection unit 104 is connected to the third and fourth terminals 50*c* and 50*d*, and detects the resistance value of the flexible resistor 28. The resistance value detected by the resistance detection unit 104 is outputted to the correction value storage unit 105 and the sensitivity correction unit 106. The correction value storage unit 105 is formed using a non-volatile memory such as EEPROM, and stores a sensitivity correction value, a reference-time resistance value, and an inspection-time resistance value. The reference-time resistance value is the resistance value of the flexible resistor 28 when a first voltage is applied between the first and second terminals 50*a* and 50*b*.

The inspection-time resistance value is the resistance value of the flexible resistor 28 when a second voltage different from the first voltage is applied between the first terminal 50*a* and the second terminal 50*b*. The sensitivity correction value is a correction value for the sensitivity calculated from the reference-time resistance value and the inspection-time resistance value. The sensitivity correction unit 106 corrects the resistance value detected by the resistance detection unit 104 in accordance with the sensitivity correction value stored in the correction value storage unit 105. The value corrected by the sensitivity correction unit 106 is outputted as an analog signal to the analog-to-digital conversion unit 107. The analog-to-digital conversion unit 107 digitally converts the result of the sensitivity correction received from the sensitivity correction unit 106, and outputs it to a personal computer or the like via the interface unit 108.

The interface unit 108 outputs a switching signal received from the personal computer or the like to the multiplexer 101. As described above, the gas sensor 1, the voltage application unit (first power supply 102, multiplexer 101), and the resistance detection unit 104 form an inspection system. The inspection system of the first embodiment further includes the correction value storage unit 105 and the sensitivity correction unit 106 in addition to the gas sensor 1, the voltage application unit and the resistance detection unit 104.

(Component Detector)

Figure 7:
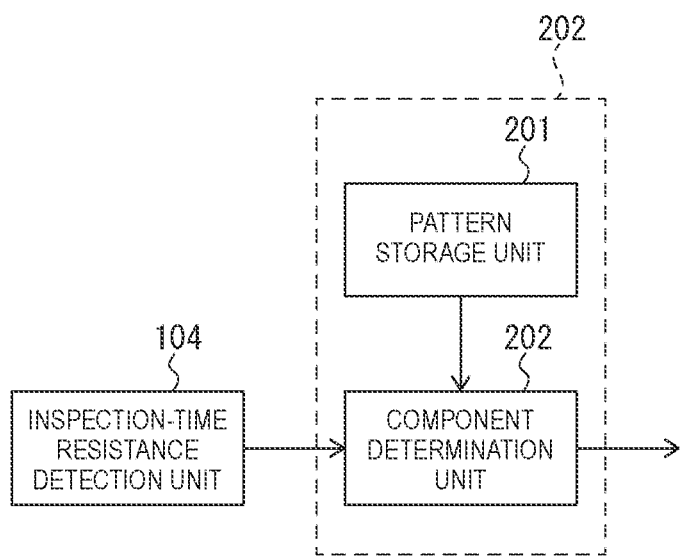
FIG. 7 is a diagram illustrating a configuration of a component detector.

The component detector 200 includes a pattern storage unit 201 and a component determination unit 202, as illustrated in FIG. 7. The pattern storage unit 201 stores in advance a response pattern with which the receptor 30 responds for a component contained in a fluid when the molecules of the fluid as a measurement target (gas) adheres to the receptor 30. The component determination unit 202 is connected to the resistance detection unit 104 and the pattern storage unit 201.

The component determination unit 202 determines a component of a measurement target by determining whether or not the pattern of the resistance value detected by the resistance detection unit 104 matches a response pattern stored in the pattern storage unit 201. The component of the measurement target determined by the component determination unit 202 is outputted to a computer or the like outside the drawings. In this way, the component detector 200 detects a component contained in a fluid adhered to the receptor 30 in accordance with the resistance value detected by the resistance detection unit 104 and the response pattern stored in the pattern storage unit 201. As described above, the gas sensor 1, the resistance detection unit 104 and the component detector 200 constitute the component detection apparatus that detects a component contained in a fluid adhered to the receptor 30.

(Gas Sensor Inspection Method)

A method of inspecting the gas sensor 1 is explained using FIGS. 8 to 15, while referring to FIGS. 1 to 7. Inspection of the gas sensor 1 is performed, for example, during factory inspection of the gas sensor 1 (at the time of manufacture, shipment, etc.) or during user use. First, an example of the inspection method for the gas sensor 1 is explained using FIGS. 8 to 12, while referring to FIGS. 1 to 7, the inspection method (may be referred to as a "first inspection method" in the following description) being performed, for example, at the time of manufacture as factory inspection. The first inspection method is performed, for example, to detect a fault occurred during the step of forming the membrane 22, cutting (dicing) a plurality of laminates of the support substrate 10 and the detection substrate 20 formed in sheet form, or coating the receptor 30.

Figure 8:
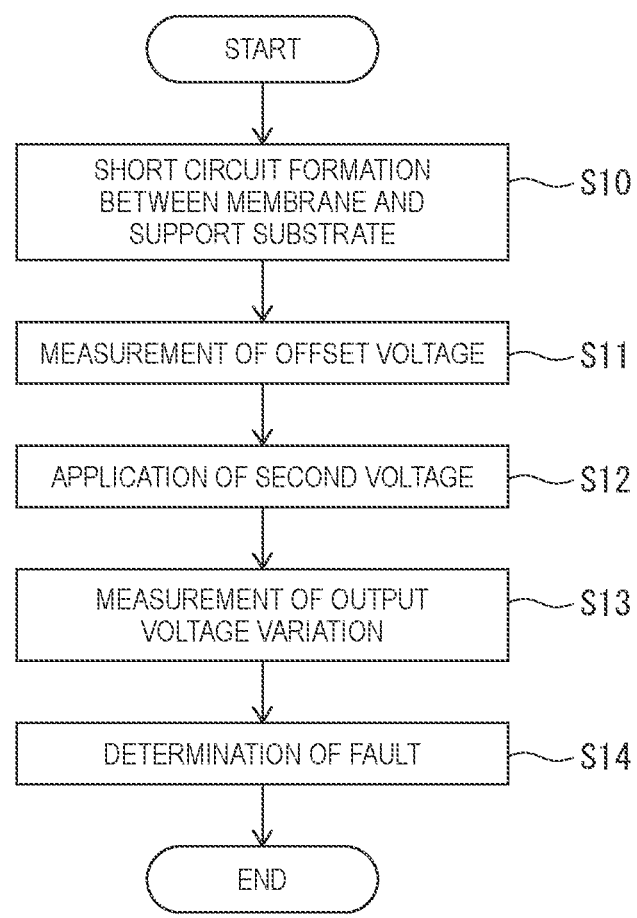
FIG. 8 is a flowchart illustrating a first inspection method.
Figure 9:
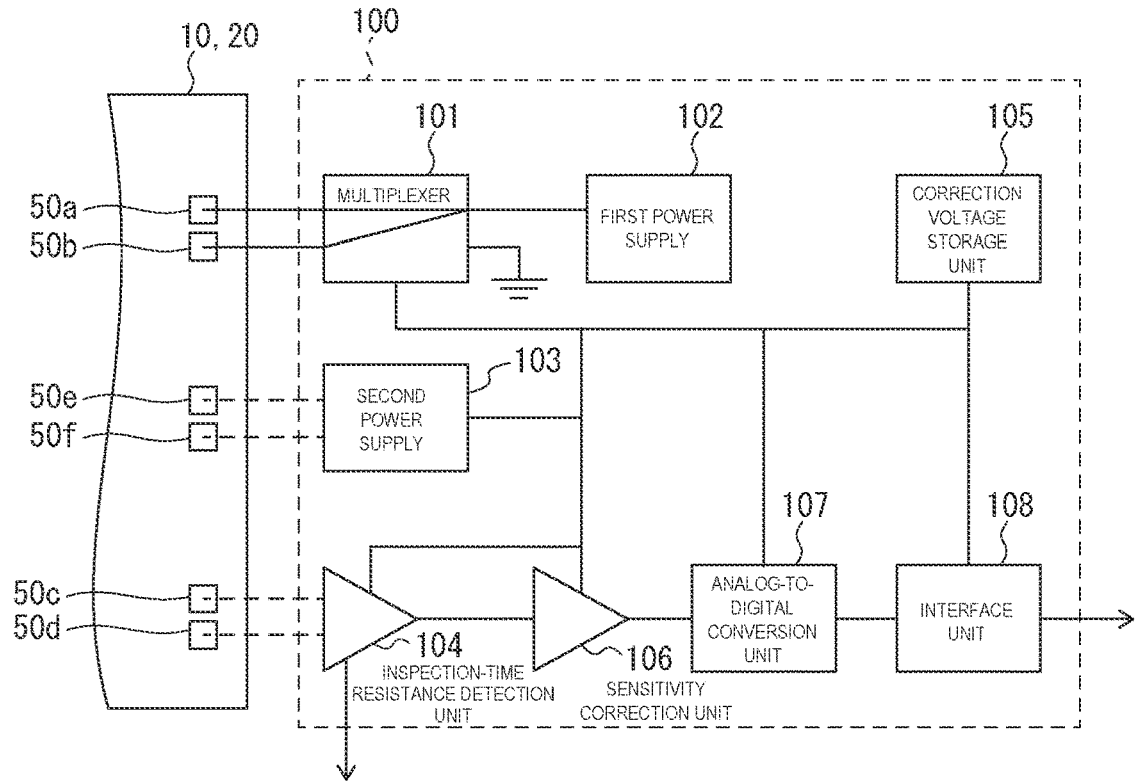
FIG. 9 is a diagram illustrating a state where a support substrate and a membrane are short-circuited.
Figure 10:
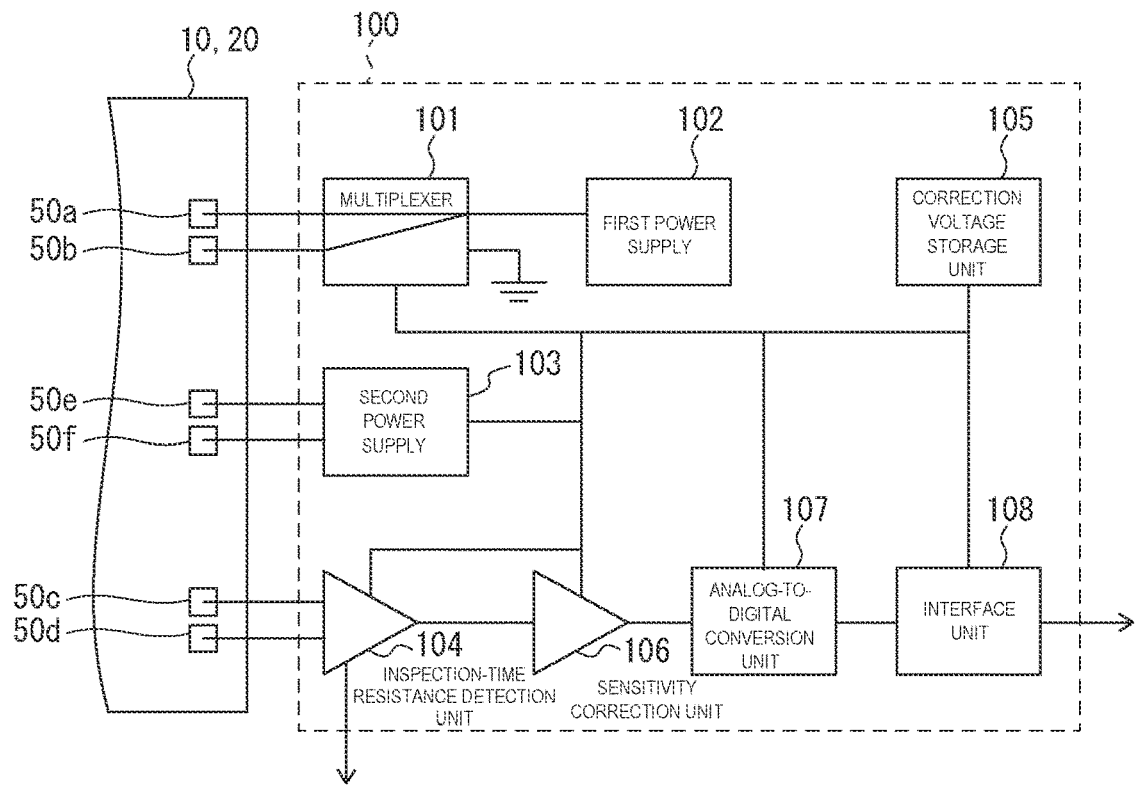
FIG. 10 is a diagram illustrating a first voltage application step.

As illustrated in FIGS. 8 and 9, in the first inspection method, the first and second terminals 50*a* and 50*b* are connected to the first power supply 102 by using the multiplexer 101 in step S10. This makes a short circuit between the support substrate 10 and the membrane 22. Next, as illustrated in FIG. 8 and FIG. 10, in step S11, an offset voltage is measured by the resistance detection unit 104 with the first voltage being applied between the first and second terminals 50*a* and 50*b* from the second power supply 103. In addition to this, the resistance detection unit 104 measures the reference resistance value, which is a resistance value according to the offset voltage.

Figure 11:
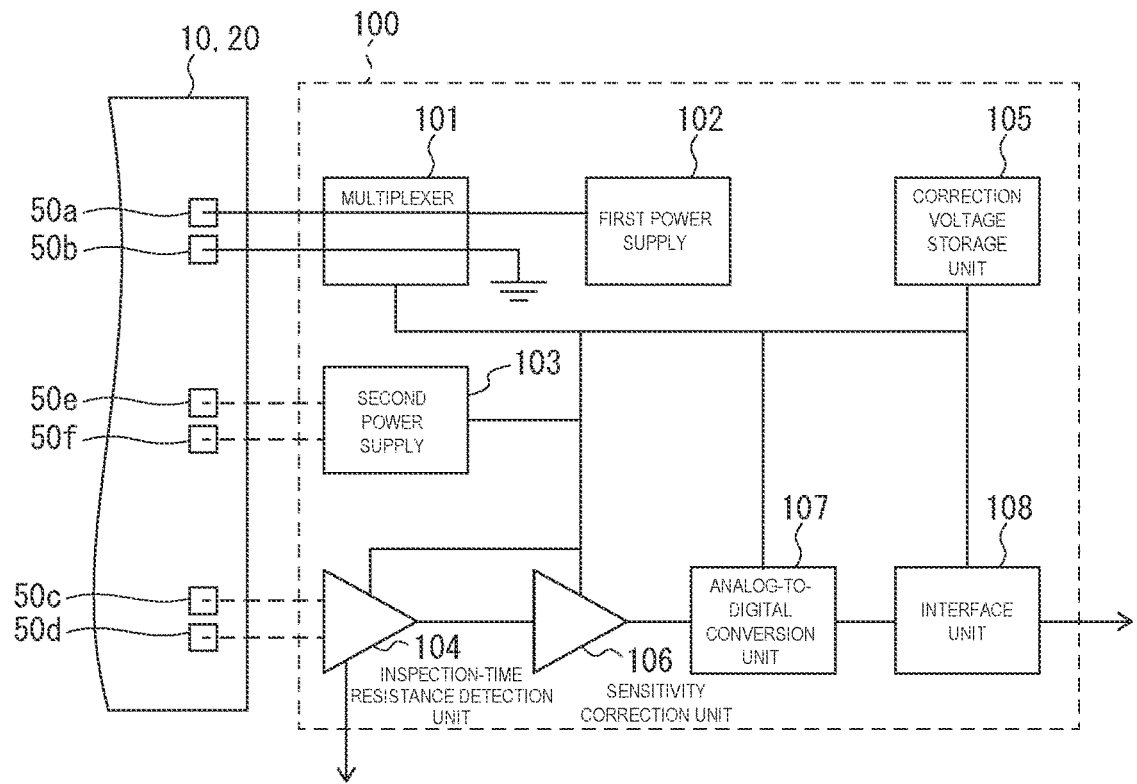
FIG. 11 is a diagram illustrating a second voltage application step.

The "offset voltage" is a voltage that occurs between the first terminal 50*a* and the second terminal 50*b* when the membrane 22 is not deformed (flat), and is usually 0 [V]. Next, as illustrated in FIG. 8 and FIG. 11, in step S12, the multiplexer 101 connects the first terminal 50*a* to the first power supply 102, and grounds the second terminal 50*b*. As a result, a second voltage, different from the first voltage is applied between the first and second terminals 50*a* and 50*b*.

Figure 12:
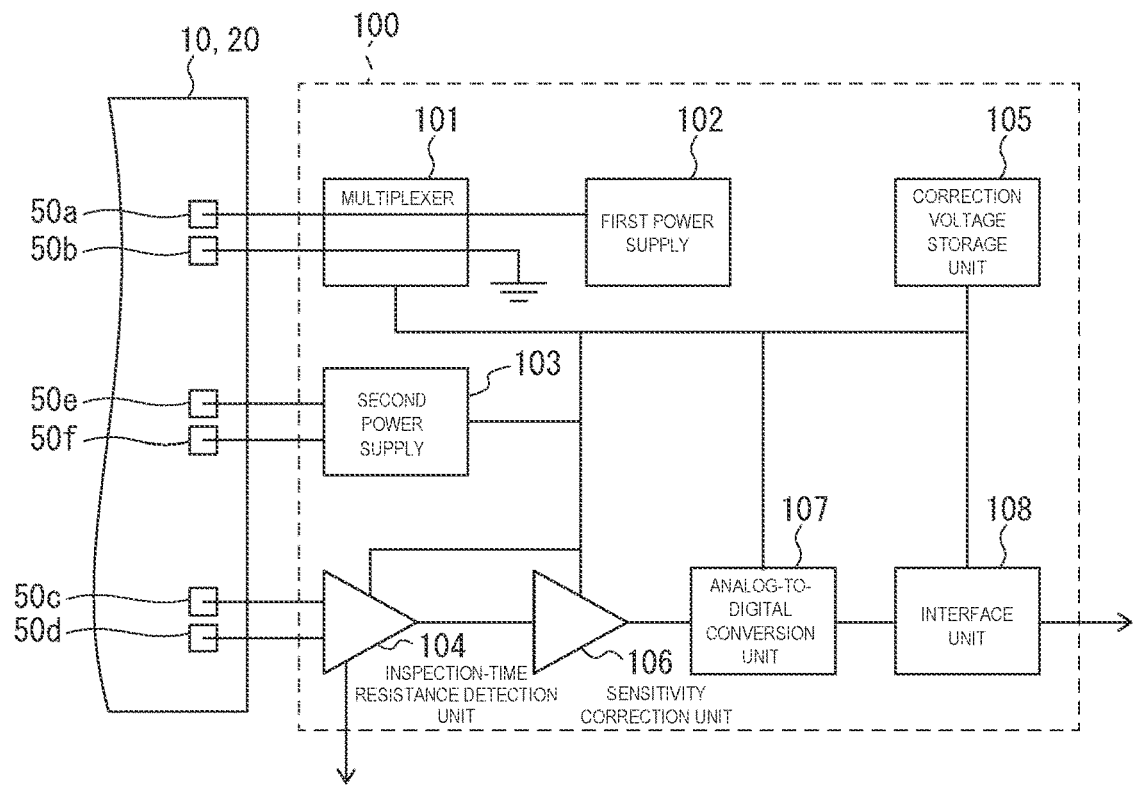
FIG. 12 is a diagram illustrating an inspection-time resistance detection step.

Thereafter, as illustrated in FIG. 8 and FIG. 12, in step S13, a voltage is measured by the resistance detection unit 104 with the second voltage being applied between the first terminal 50*a* and the second terminal 50*b*. In addition to this, the inspection-time resistance value, which is the resistance value of the flexible resistor 28 according to the second voltage, is measured by the resistance detection unit 104. Then, as illustrated in FIG. 8, in step S14, it is determined whether the operation of membrane 22 is faulty or not in accordance with a variation between the offset voltage measured in step S11 and the voltage measured in step S13. After that, the first inspection method is terminated.

For the gas sensor 1 for which a determination that the operation of the membrane 22 is faulty has been made, measures such as structure modification are taken. As described above, the inspection method of the gas sensor 1 (first inspection method) is an inspection method to inspect the operation of the membrane 22 for the gas sensor 1, and includes the second voltage application step, the inspection-time resistance detection step, and the determination step. The second voltage application step (step S12) is a step for applying the preset second voltage between the first terminal 50*a* and the second terminal 50*b*.

The inspection-time resistance detection step (step S13) is a step for detecting the inspection-time resistance value. The inspection-time resistance value is the resistance value of the flexible resistor 28 with the second voltage being applied between the first and second terminals 50*a* and 50*b*. The determination step (step S14) is a step for checking the operation of the membrane 22 based on the inspection-time resistance value detected in the inspection-time resistance detection step, and the reference resistance value which is the resistance value with the preset first voltage being applied between the first terminal 50*a* and the second terminal 50*b*. In the determination step, for example, if the difference between the inspection-time resistance value and the reference resistance value exceeds a preset difference threshold, the operation of the membrane 22 is determined to be abnormal. The difference threshold is set to $2.0 \times 10^{-2}$ [Ω], for example. The difference threshold is set, for example, by calculating a resistance variation when an output of 10 μV is obtained (Sim prediction) by a Coulomb force.

Furthermore, the inspection method for the gas sensor 1 (the first inspection method) includes the first voltage application step and the measurement step. The first voltage application step (step S11), which is a pre-step of the second voltage application step, is a step for applying the first voltage different from the second voltage between the first terminal 50*a* and the second terminal 50*b*. The measurement step (step S11) is a step for measuring the reference resistance value with the first voltage being applied between the first terminal 50*a* and the second terminal 50*b* in the first voltage application step.

Figure 13:
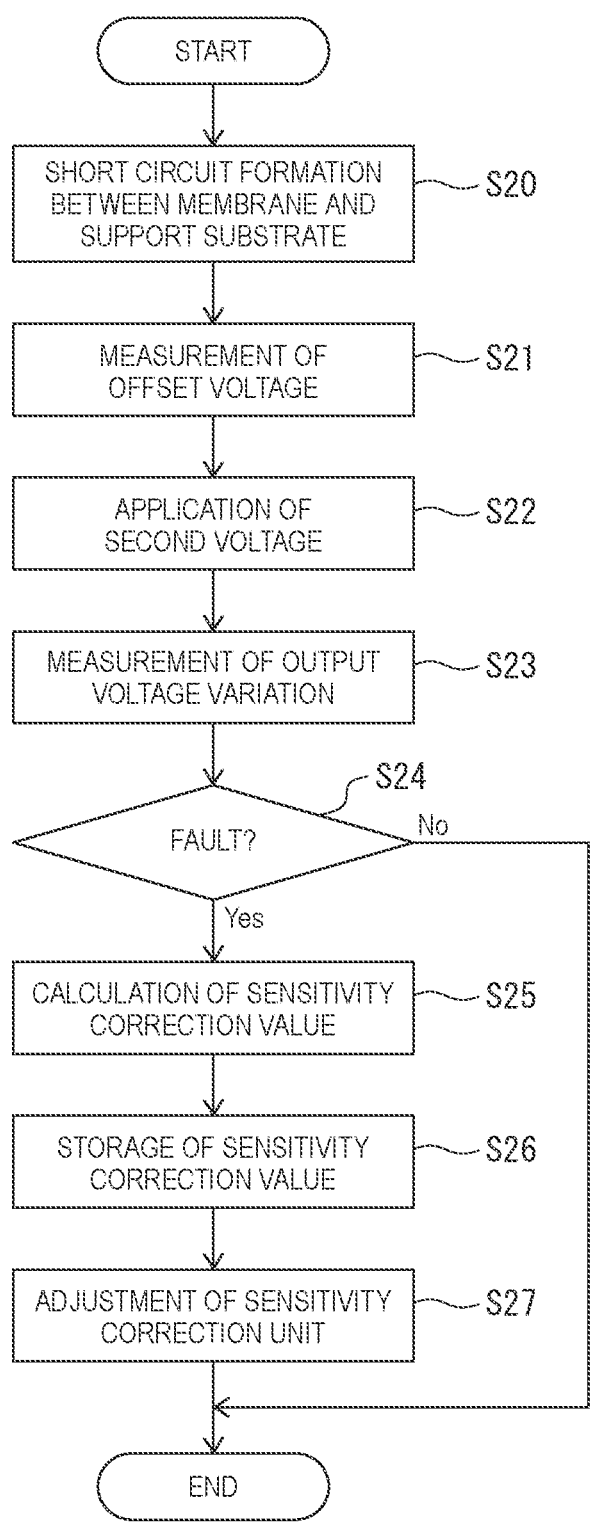
FIG. 13 is a flowchart illustrating a second inspection method.
Figure 14:
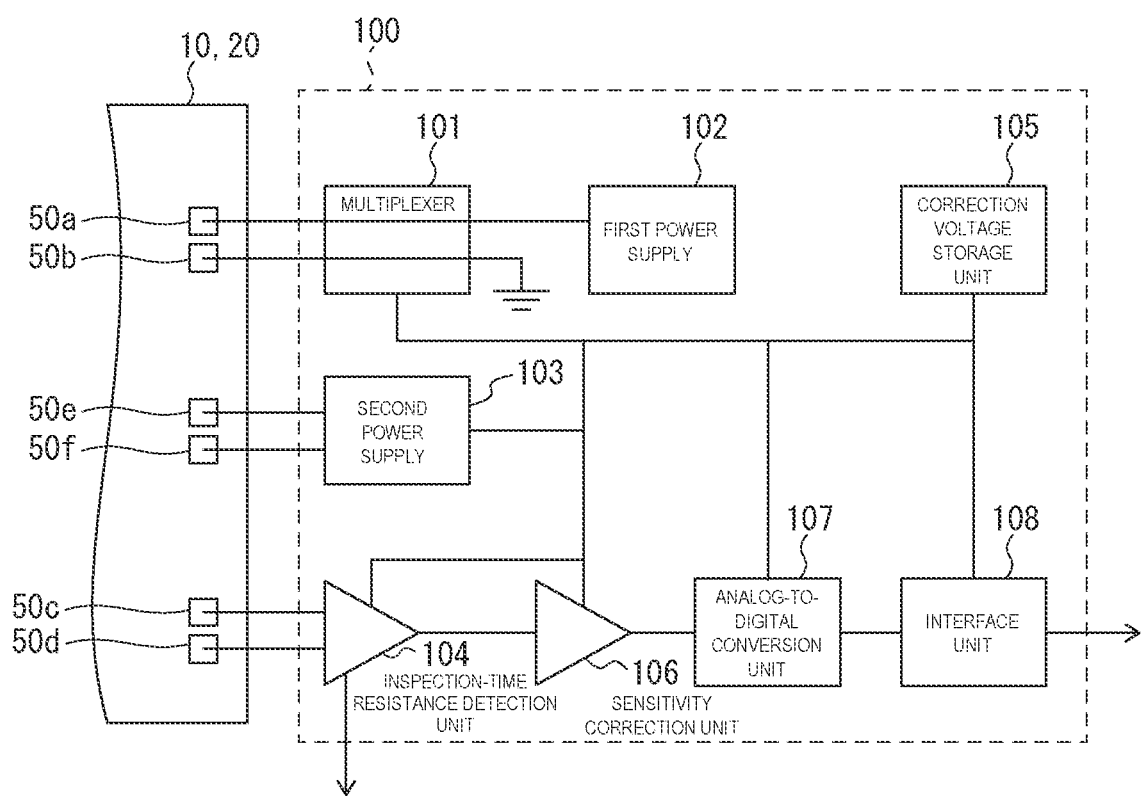
FIG. 14 is a diagram illustrating an inspection-time resistance value correction step.

Next, an example of the inspection method for the gas sensor 1 is explained using FIGS. 13 and 14, while referring to FIGS. 1 to 12, this inspection method (may be referred to as a "second inspection method" in the following description) being performed, for example, at the time of shipment or the like, as factory inspection. The second inspection method is performed to detect a fault occurring in the gas sensor 1 installed, for example, in the component detection apparatus or the inspection system. As illustrated in FIG. 13 and FIG. 9, in the second inspection method, the first and second terminals 50*a* and 50*b* are connected to the first power supply 102 by using the multiplexer 101 in step S20. This makes a short circuit between the support substrate 10 and the membrane 22.

Next, as illustrated in FIG. 13 and FIG. 10, in step S21, with the first voltage being applied between the first and second terminals 50*a* and 50*b* from the second power supply 103, the offset voltage is measured by the resistance detection unit 104. In addition to this, the resistance detection unit 104 measures the reference resistance value, which is a resistance value according to the offset voltage. Thereafter, as illustrated in FIG. 13 and FIG. 11, in step S22, the multiplexer 101 connects the first terminal 50*a* to the first power supply 102, and grounds the second terminal 50*b*. As a result, the second voltage, different from the first voltage is applied between the first and second terminals 50*a* and 50*b*.

Next, as illustrated in FIG. 13 and FIG. 12, in step S23, with the second voltage being applied between the first terminal 50*a* and the second terminal 50*b*, a voltage is measured by the resistance detection unit 104. In addition to this, the resistance detection unit 104 measures the inspection-time resistance value which is the resistance value of the flexible resistor 28 according to the second voltage. Then, as illustrated in FIG. 13, in step S24, it is determined whether the operation of the membrane 22 is faulty or not in accordance with the variation between the offset voltage measured in step S21 and the voltage measured in step S23.

If the operation of the membrane 22 is determined to be faulty in step S24, the second inspection method is terminated. For the gas sensor 1 for which a determination that the operation of the membrane 22 is faulty, measures such as structure modification are taken. On the other hand, if it is determined in step S24 that the operation of the membrane 22 is not faulty, as illustrated in FIG. 13, in step S25, the sensitivity correction value, which is a correction value for sensitivity according to the variation between the offset voltage measured in step S21 and the voltage measured in step S23, is calculated.

Next, as illustrated in FIG. 13, in step S26, the sensitivity correction value calculated in step S25 is stored in the correction value storage unit 105. Then, as illustrated in FIGS. 13 and 14, in step S27, the sensitivity correction values stored in the correction value storage unit 105 in step 26 is set as the sensitivity correction value to be used by the sensitivity correction unit 106. After that, the second inspection method is terminated. As described above, the inspection method for the gas sensor 1 (the second inspection method), further includes, in addition to the first inspection method, the correction value calculation step, the correction value storage step, and the sensitivity correction unit adjustment step.

The correction value calculation step (step S25) is a step for calculating, if the operation of the membrane is determined to be better than the reference value in the determination step (step S24), the sensitivity correction value, which is a correction value for sensitivity according to the reference resistance value detected in the reference resistance detection step (step S21) and the inspection-time resistance value detected in the inspection-time resistance detection step (step S23). The correction value storage step (step S26) is a step for storing the sensitivity correction value calculated in the correction value calculation step. The sensitivity correction unit adjustment step (step S27) is a step for adjusting the sensitivity correction unit 106 using the sensitivity correction value stored in the correction value storage step.

Figure 15:
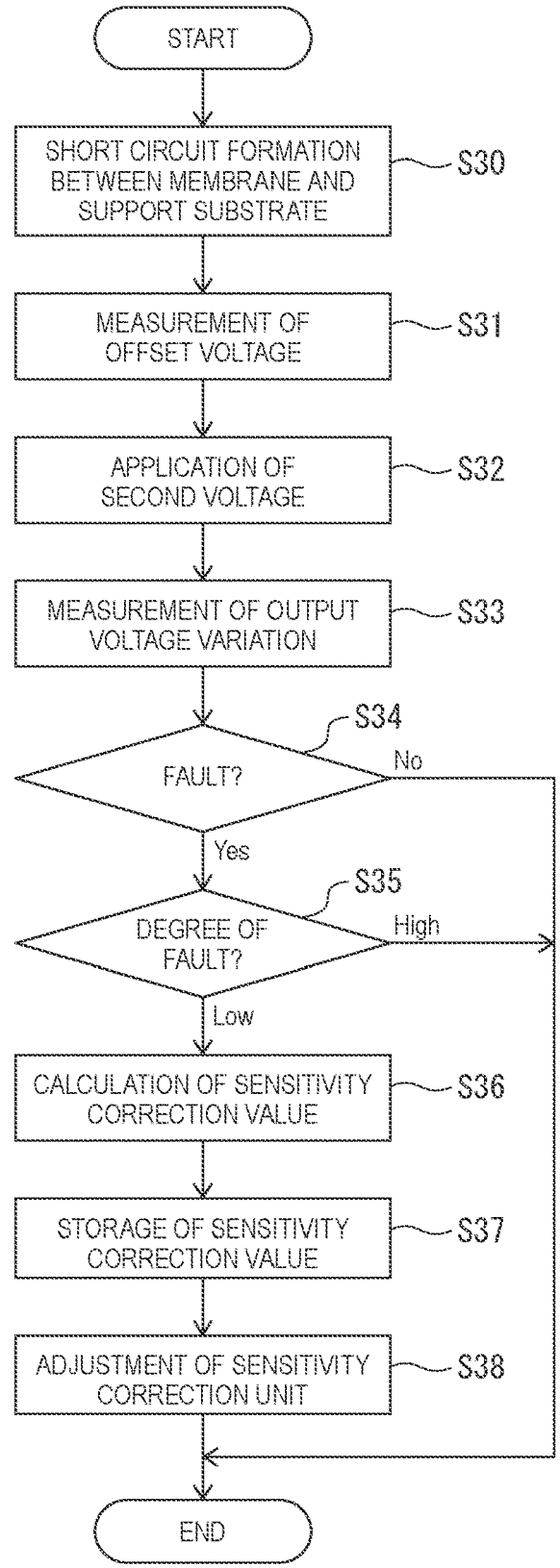
FIG. 15 is a flowchart illustrating a third inspection method.

Next, an example of the inspection method for the gas sensor 1 performed during user use (may be referred to as the "third inspection method" in the following description) is explained using FIG. 15, while referring to FIGS. 1 to 14. The third inspection method is performed, for example, to detect an operational fault caused by structural breakdown due to dropping or vibration when the gas sensor 1 is in use. As illustrated in FIG. 15 and FIG. 9, in the third inspection method, the multiplexer 101 is used to connect the first and second terminals 50a and 50b to the first power supply 102 in step S30. This makes a short circuit between the support substrate 10 and the membrane 22.

Next, as illustrated in FIG. 15 and FIG. 10, in step S31, with the first voltage being applied between the first and second terminals 50a and 50b from the second power supply 103, an offset voltage is measured by the resistance detection unit 104. In addition to this, the resistance detection unit 104 measures the reference resistance value, which is a resistance value according to the offset voltage.

Thereafter, as illustrated in FIG. 15 and FIG. 11, in step S32, the multiplexer 101 connects the first terminal 50a to the first power supply 102, and grounds the second terminal 50b. As a result, the second voltage different from the first voltage is applied between the first and second terminals 50a and 50b.

Next, as illustrated in FIG. 15 and FIG. 12, in step S33, with the second voltage being applied between the first terminal 50a and the second terminal 50b, a voltage is measured by the resistance detection unit 104. In addition to this, the resistance detection unit 104 measures the inspection-time resistance value which is the resistance value of the flexible resistor 28 according to the second voltage. Then, as illustrated in FIG. 15, in step S34, it is determined whether the operation of the membrane 22 is faulty or not in accordance with the variation between the offset voltage measured in step S31 and the voltage measured in step S33.

If it is determined in step S34 that the operation of the membrane 22 is not faulty, the third inspection method is terminated. On the other hand, if the operation of the membrane 22 is determined to be faulty in step S34, the degree of a fault of the operation of the membrane 22 is determined in step S35, as illustrated in FIG. 15. In step S35, for example, if the difference between the inspection-time resistance value and the reference resistance value exceeds a preset quality determination threshold, the degree of the fault is determined to be high. The quality determination threshold is set to, for example, $1.0 \times 10^{-3}[\Omega]$. This determination can be made also by comparing the difference between the reference resistance value and the inspection-time resistance value during user use with the difference between the reference resistance value and the inspection-time resistance value, which were acquired at the time of factory shipment and stored in the correction value storage unit 105.

In the first embodiment, though the quality threshold is set to half the value used at the time of factory inspection, as a resistance variation (output variation) that is an absolute threshold, it is not limited to this. That is, for example, the quality threshold may be a relative threshold. In this case, the relative threshold may be specified, for example, by an amount of sensitivity reduction from sensitivity at the time of factory shipment (e.g., 50% reduction). If the degree of the fault is determined to be high in step S35, the third inspection method is terminated. For the gas sensor 1 including the membrane 22 having been determined to have a high degree of faulty operation, the manufacturer may take measures such as structure modification, for example.

On the other hand, if the degree of the fault is determined to be low in step S35, the sensitivity correction value, which is a correction value for sensitivity according to the inspection-time resistance value detected in step S33, is calculated in step S36, as illustrated in FIG. 15. The membrane 22 having been determined to have a low degree of faulty operation is the membrane 22 that is in a state enabling the gas sensor 1 to achieve a minimum required performance, for example. Next, as illustrated in FIG. 15, in step S37, the sensitivity correction value calculated in step S36 is stored in the correction value storage unit 105.

Then, as illustrated in FIG. 15, in step S38, the sensitivity correction value stored in step S37 is set as the sensitivity correction value to be used in the sensitivity correction unit 106. After that, the third inspection method is terminated. As described above, the inspection method for the gas sensor 1 (the third inspection method) includes, in addition to the second inspection method, the fault degree determination step. The fault degree determination step (step S35) is a step for determining a degree of faulty operation of the membrane 22 based on the inspection-time resistance value and the reference resistance value.

During manufacture of the gas sensor 1, etc., a residual stress may exist in the membrane 22, or the membrane 22 may be convex (deformed) due to stretching of the membrane 22 that occurs when the receptor 30 is dried. As described above, by setting the offset voltage to 0 [V], the input range of a differential amplifier can be reduced. Therefore, by performing the second inspection method, the voltage between the membrane 22 and the support substrate 10 that cause the offset voltage to be 0 [V], is stored in the correction value storage unit 105 before shipping the gas sensor 1.

Accordingly, application of the stored voltage is made possible by performing the third inspection method, which is a post-shipment measurement mode.

(Gas Sensor Manufacturing Method)

A manufacturing method for the gas sensor 1 is explained using FIGS. 16A, 16B, 16C, 16D to 26, while referring to FIGS. 1 to 15. The cross-sectional views in FIGS. 16A, 16B, 16C, 16D to 26 correspond to the X-X line cross-sectional view of FIG. 2. The manufacturing method for the gas sensor 1 includes a laminate formation step, a through-electrode formation step, a first ion implantation step, a second ion implantation step, a third ion implantation step, a low-resistance area formation step, a removal step, a wiring layer formation step, and a receptor formation step.

(Laminate Formation Step)

Figure 16A:
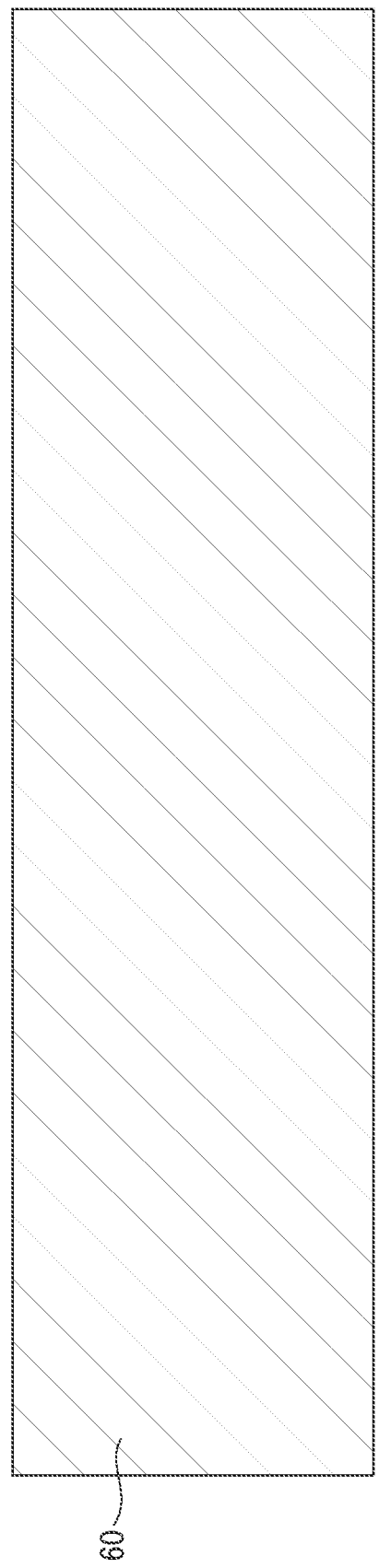
FIG. 16A is a diagram illustrating a laminate formation step.
Figure 16B:
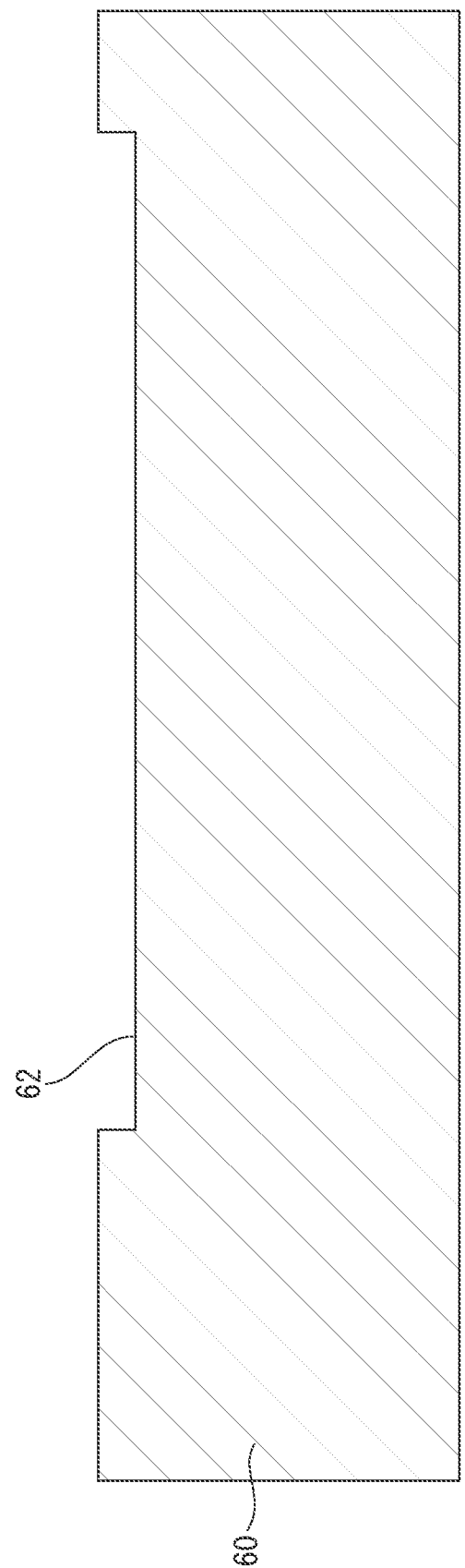
FIG. 16B is a diagram illustrating the laminate formation step.

In the laminate formation step, first, a recess 62 (trench) is formed on one side of a first silicon substrate 60 illustrated in FIG. 16A, which becomes a material of the support substrate 10, using lithography and etching technologies, as illustrated in FIG. 16B. The depth of the recess 62 is set to 4 [μm], for example. The first silicon substrate 60 is an electrically conductive N type silicon substrate. Next, as illustrated in FIG. 16C, the insulating portion 6 is formed by forming a first silicon oxide film 68a on one side of the first silicon substrate 60.

In addition, a second silicon substrate 64, which becomes a material of the detection substrate 20, is laminated using various bonding technologies such as adhesion, so as to cover a part of the first silicon substrate 60, on which the insulating portion 6 has been formed, to thereby form a laminate 66 (cavity wafer) as illustrated in FIG. 16D. The second silicon substrate 64 is an electrically conductive N type silicon substrate. Accordingly, the first silicon substrate 60 and the second silicon substrate 64 are semiconductor substrates having the same conductivity type. As described above, by performing the laminate formation step, the gap 40 surrounded by the insulating portion 6 and the second silicon substrate 64 vertically and horizontally is formed at a predetermined position of the laminate 66. As described above, in the laminate formation step, the recess 62 is formed on one side of the support substrate 10, the insulating portion 6 is formed on the one side of the support substrate 10, and the detection substrate 20 is laminated so as to cover a part of the support substrate 10, on which the insulating portion 6 has been formed. As a result, the laminate 66 with the gap 40 existing between the support substrate 10 and the detection substrate 20 is formed.

(Through-Electrode Formation Step)

In the through-hole electrode formation step, first, as illustrated in FIG. 17A, a second silicon oxide film 68b is formed on the surface on one side of the second silicon substrate 64, which is opposite to the other side facing the first silicon substrate 60. The thickness of the second silicon oxide film 68b is set to 400 [nm], for example. Next, as illustrated in FIG. 17B, two first trenches 56a are formed in the second silicon oxide film 68b using the lithography and etching technologies. The width of the first trench 56a (the length in the left-right direction in FIG. 17B) is set to, for example, 0.5 [mm].

Furthermore, as illustrated in FIG. 17C, using the second silicon oxide film 68b as a mask, two second trenches 56b overlapping with the two first trenches 56a respectively, are formed on the second silicon substrate 64 using etching technology. Next, as illustrated in FIG. 18A, the laminate 66 is thermally oxidized (e.g., 300 [nm]) to seal the two first trenches 56a and the two second trenches 56b with a third silicon oxide film 68c. This prevents a short circuit between the second silicon substrate 64 and the first silicon substrate 60 after the through-electrode 54 is formed. Next, as illustrated in FIG. 18B and FIG. 18C, the lithography and etching technologies are used to remove a part of the second silicon oxide film 68b and the second silicon substrate 64, which exists between the two first trenches 56a and the two second trenches 56b. As a result, a through-hole 58 for forming the through-electrode 54 is formed.

Figure 19A:
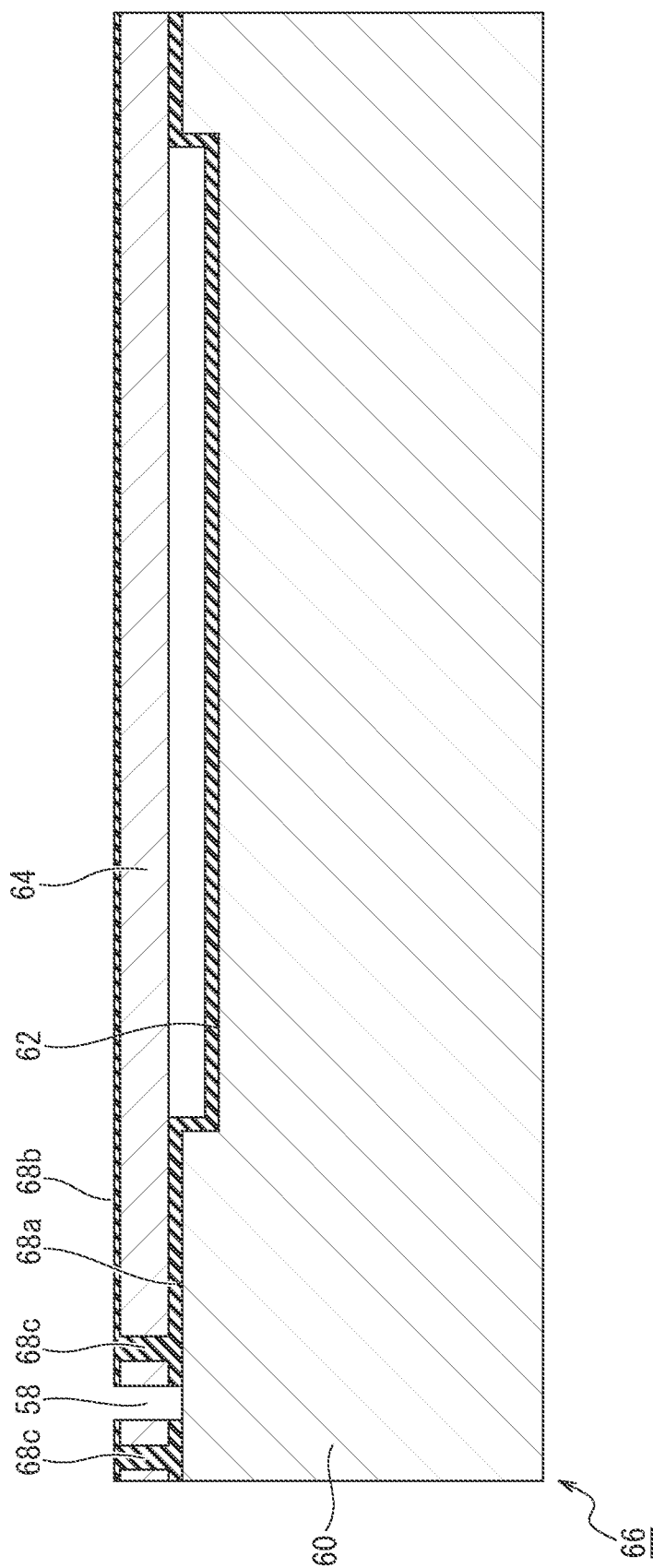
FIG. 19A is a diagram illustrating the through-electrode formation step.

Furthermore, as illustrated in FIG. 19A, the first silicon oxide film 68a having been formed on the first silicon substrate 60 is etched away. At this time, the thickness of the second silicon oxide film 68b is about 50 [nm]. Next, as illustrated in FIG. 19B, a film of N type polysilicon 96 is formed as an electrode material containing impurities. At this time, the inside of the through-hole 58 is filled with the N type polysilicon 96. In addition, as illustrated in FIG. 19C, unnecessary N type polysilicon 96 is removed by etching (or chemical mechanical polishing). As a result, the through-electrode 54 formed of N type polysilicon is provided inside the through-hole 58.

As described above, in the through-electrode formation step, apart of the detection substrate 20 and the insulating portion 6 is removed to form the through-hole 58 that penetrates from the surface on the one side of the detection substrate 20, which is opposite to the other side facing the support substrate 10, to the support substrate 10. In addition, in the through-electrode formation step, the through-hole 58 is buried with an electrode material containing impurities to form the through-electrode 54 that reaches the support substrate 10 from the surface of the detection substrate 20.

(First Ion Implantation Step)

Figure 20:
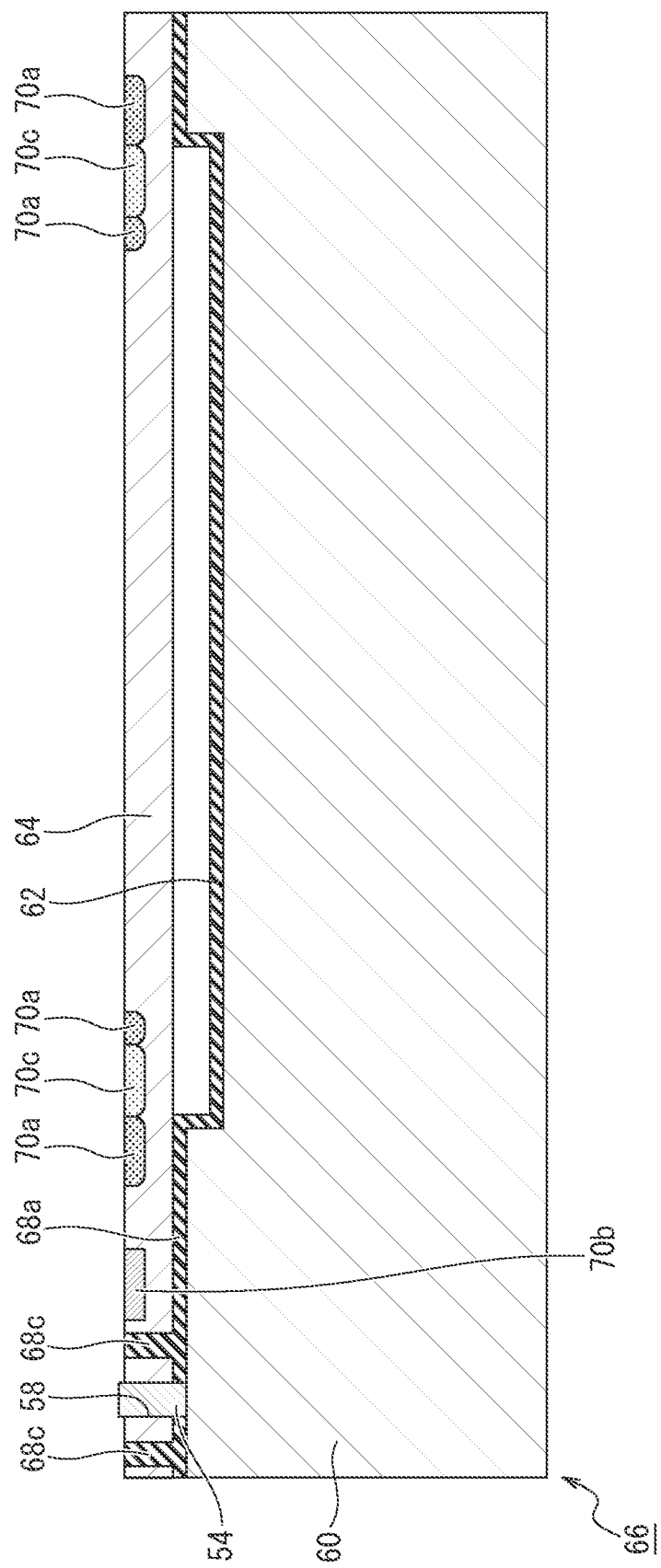
FIG. 20 is a diagram illustrating a first ion implantation step, a second ion implantation step, and a third ion implantation step.

In the first ion implantation step, the second silicon oxide film 68b is removed, as illustrated in FIG. 20. Then, using a photoresist pattern (not shown), first ions are implanted into selected partial areas (first ion implantation areas 70a) of the surface of the detection substrate 20, which are outside a preset area that includes the center of the detection substrate 20. As the first ions, ions that cause the first ion implantation areas 70a to become a P++ type semiconductor layers by heat treatment is used. Therefore, in the first ion implantation step, the first ions are implanted into the selected partial areas (the first ion implantation areas 70a) of the surface of the detection substrate 20, which are outside the preset area that includes the center of the detection substrate 20.

(Second Ion Implantation Step)

In the second ion implantation step, as illustrated in FIG. 20, second ions are implanted in a selected area (a second ion implantation area 70b) of the detection substrate 20, which is outside the area where the first ions have been implanted (the first ion implantation areas 70a). As the second ions, ions that cause the second ion implantation area 70b to become an N++ type semiconductor layer by heat treatment is used.

(Third Ion Implantation Step)

In the third ion implantation step, as illustrated in FIG. 20, third ions are implanted into areas (third ion implantation areas 70c) of the surface of the detection substrate 20, which are preset inside the first ion implantation areas 70a. As the third ions, ions that cause the third ion implantation areas 70c to become P+ type semiconductor layers by heat treatment are used.

(Low-Resistance Area Formation Step)

Figure 21:
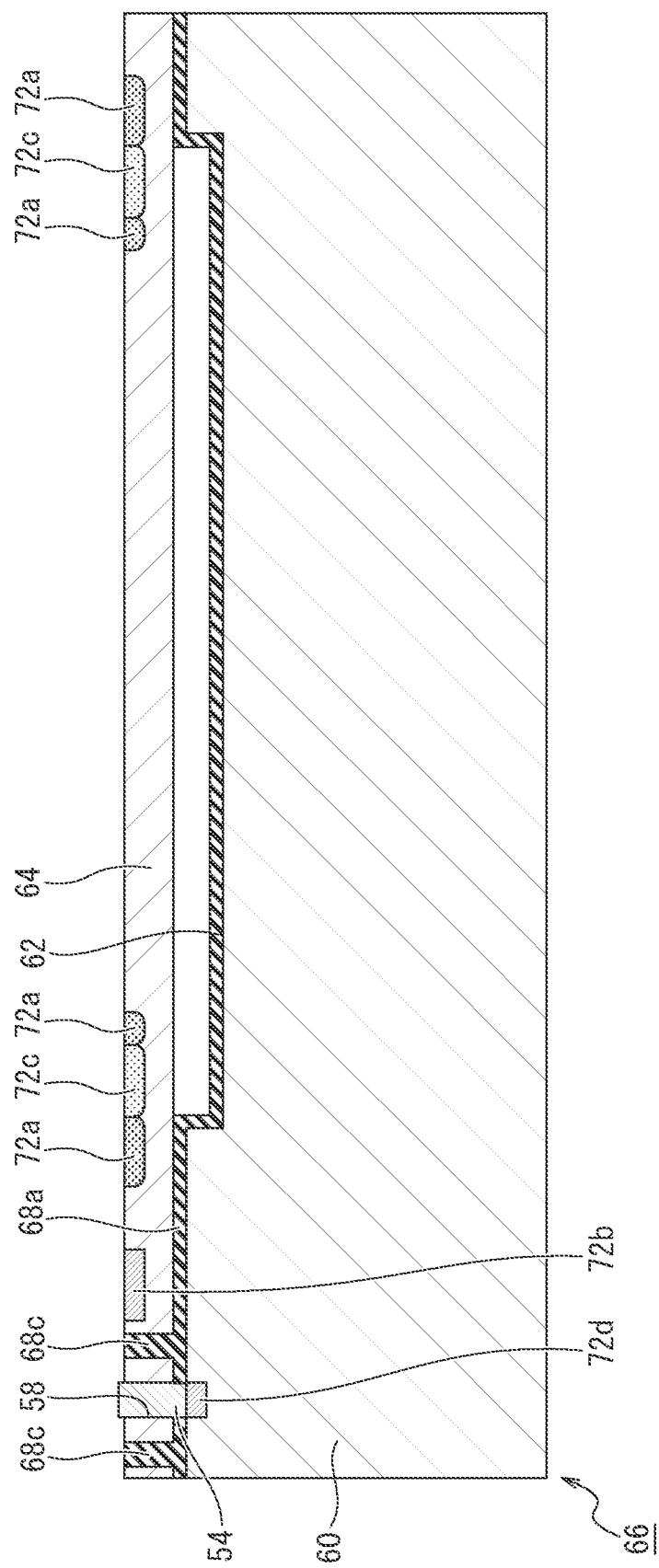
FIG. 21 is a diagram illustrating a low-resistance area formation step.

In the low-resistance area formation step, the laminate 66 is subjected to heat treatment (annealing process). This causes activation of the ions implanted into the first, second and third ion implantation steps, and solid phase diffusion of impurities (carriers) from the through-electrode 54 formed of N type polysilicon into the support substrate 10. Subjecting the laminate 66 to heat treatment forms first low-resistance areas 72a (P++ type semiconductor layers), a second low-resistance area 72b (an N++ type semiconductor layer), and a third low-resistance areas 72c (P+ type semiconductor layers) on the surface of the detection substrate 20, as illustrated in FIG. 21. In addition, a fourth low-resistance area 72d (an N++ type semiconductor layer) is formed in a part of the support substrate 10.

The first low-resistance areas 72a are preset areas of the surface of the second silicon substrate 64. Specifically, the first low-resistance areas 72a are areas where the coupling portions 26 are formed later. The second low-resistance area 72b is a preset area of the surface of the second silicon substrate 64. Specifically, the second low-resistance area 72b is an area where the first terminal 50a is formed later. The third low-resistance areas 72c are areas set inside the second low-resistance area 72b. Specifically, the third low-resistance areas 72c are areas where the flexible resistors 28 are formed later. The fourth low-resistance area 72d is a preset area of the surface on a side of the first silicon substrate 60, which faces the second silicon substrate 64. Specifically, the fourth low-resistance area 72d is an area where the second terminal 50b is formed later.

As described above, in the low-resistance area formation step, the first low-resistance areas 72a, the second low-resistance area 72b, and the third low-resistance areas 72c are formed on the detection substrate 20 by heat-treating the ion-implanted laminate 66. Furthermore, by heat-treating the laminate 66 formed with the through-electrode 54, impurities are solid-phase diffused from the through-electrode 54 into the support substrate 10 to thereby form the fourth low-resistance area 72d in the preset area of the side of the support substrate 10, which faces the detection substrate 20.

(Wiring Layer Formation Step)

Figure 22:
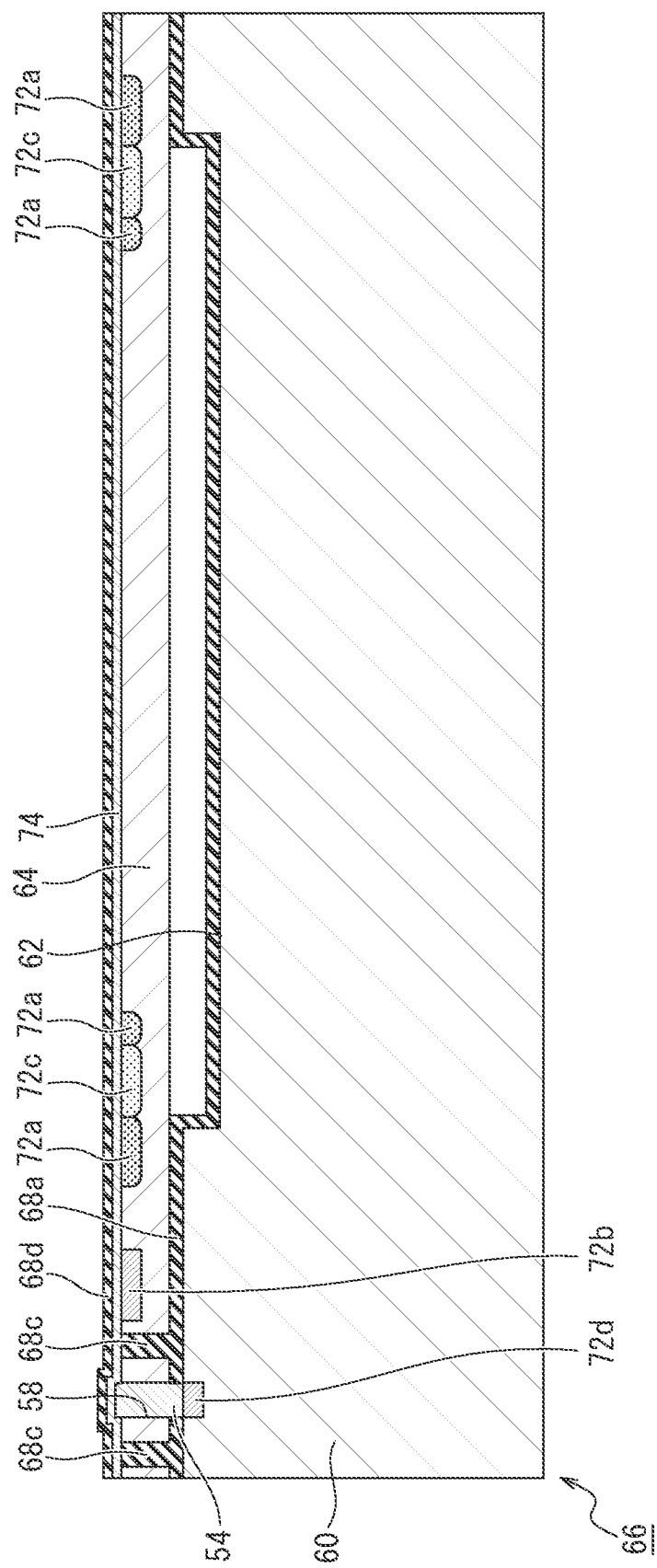
FIG. 22 is a diagram illustrating a wiring layer formation step.
Figure 23:
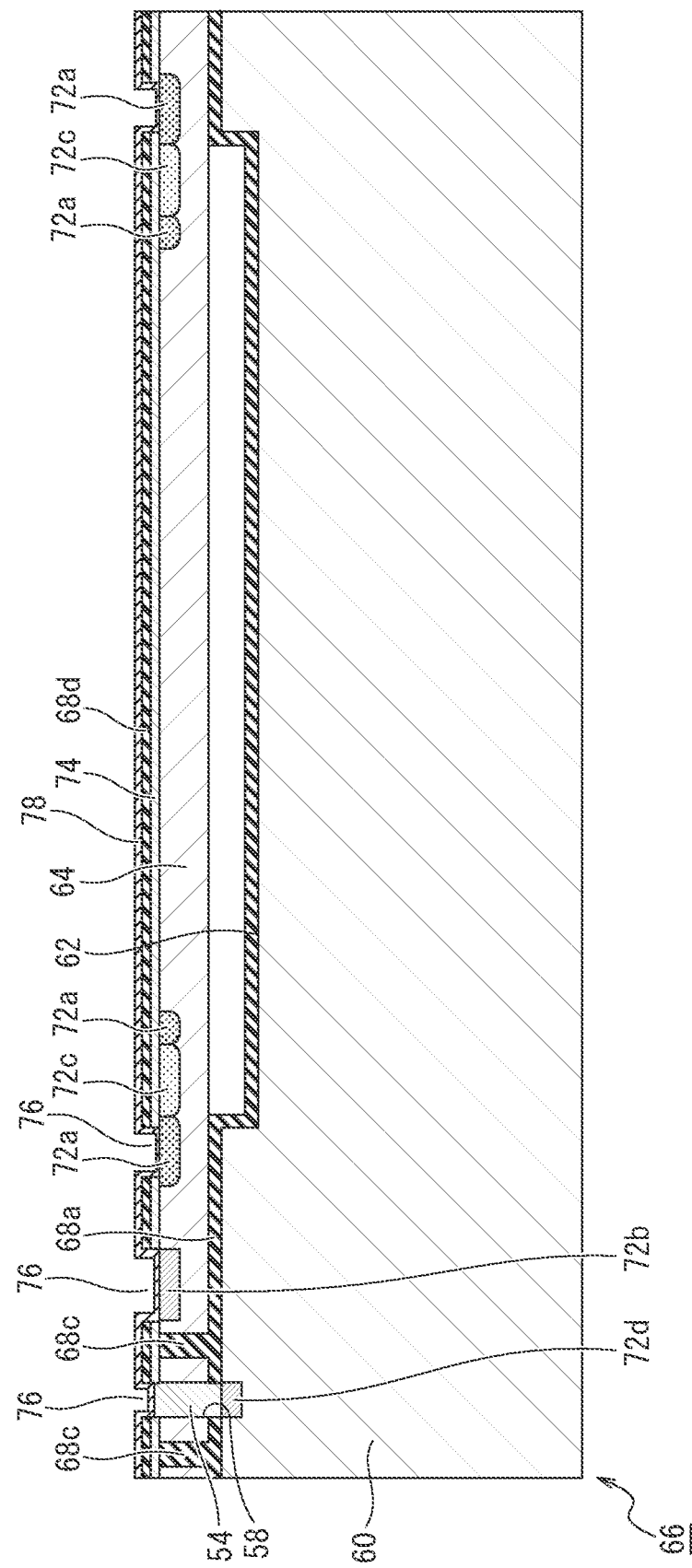
FIG. 23 is a diagram illustrating the wiring layer formation step.

In the wiring layer formation step, as illustrated in FIG. 22, a silicon nitride film 74 and a fourth silicon oxide film 68d are laminated in succession on the upper side of the second silicon substrate 64. Then, as illustrated in FIG. 23, holes 76 that reach the first low-resistance areas 72a, the second low-resistance area 72b, the third low-resistance areas 72c, and the fourth low-resistance area 72d are formed in the fourth silicon oxide film 68d and the silicon nitride film 74. The formation of the holes 76 are performed using ordinary lithography and oxide film etching.

Next, as illustrated in FIG. 23, a laminated film 78 of Ti and TiN is formed on the second silicon oxide film 68b by sputtering, and is heat-treated. The laminated film 78 is a so-called barrier metal that serves to prevent a metal film of Al or the like from abnormally diffusing into Si, and which, by applying heat treatment, an interface between Si and Ti existing at the bottom of the hole 76 is silicidized, makes it possible to form a low-resistance connection.

Figure 24:
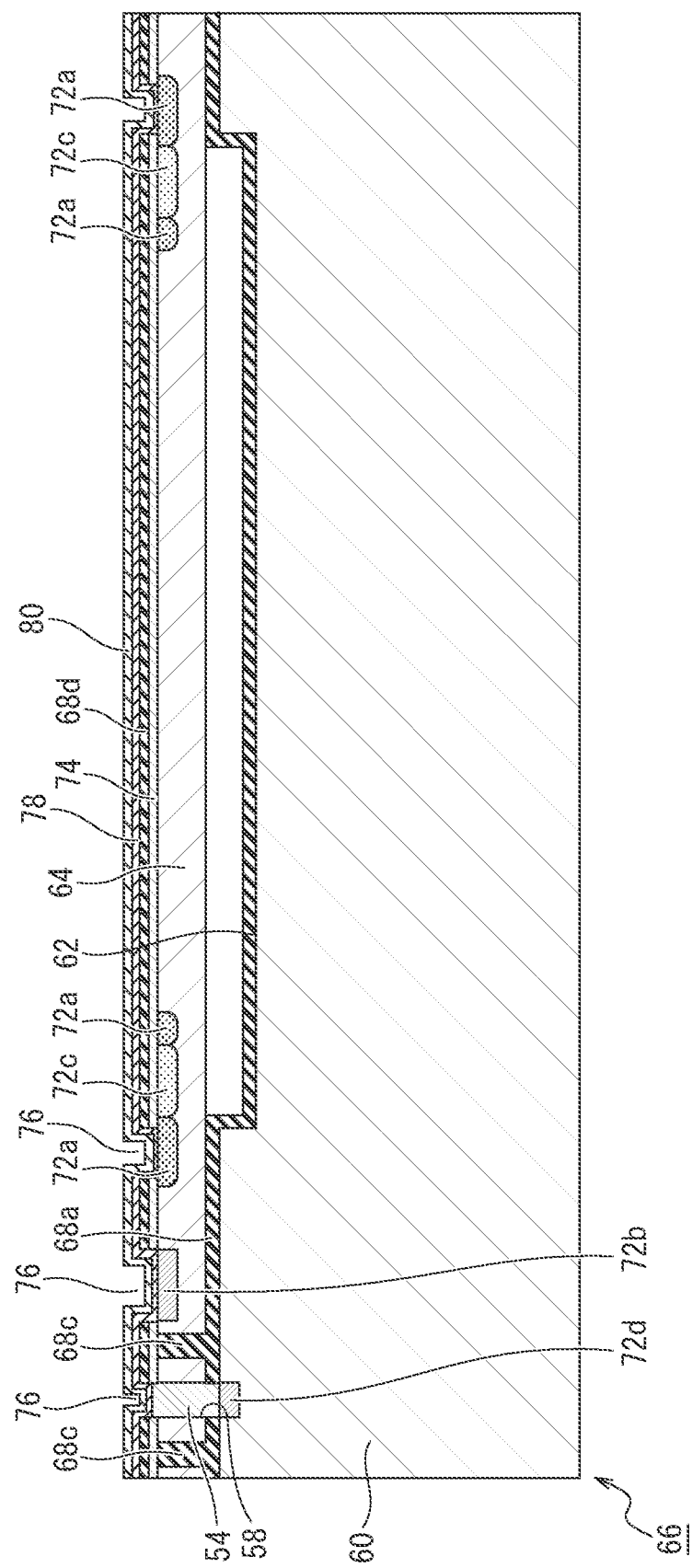
FIG. 24 is a diagram illustrating the wiring layer formation step.
Figure 25:
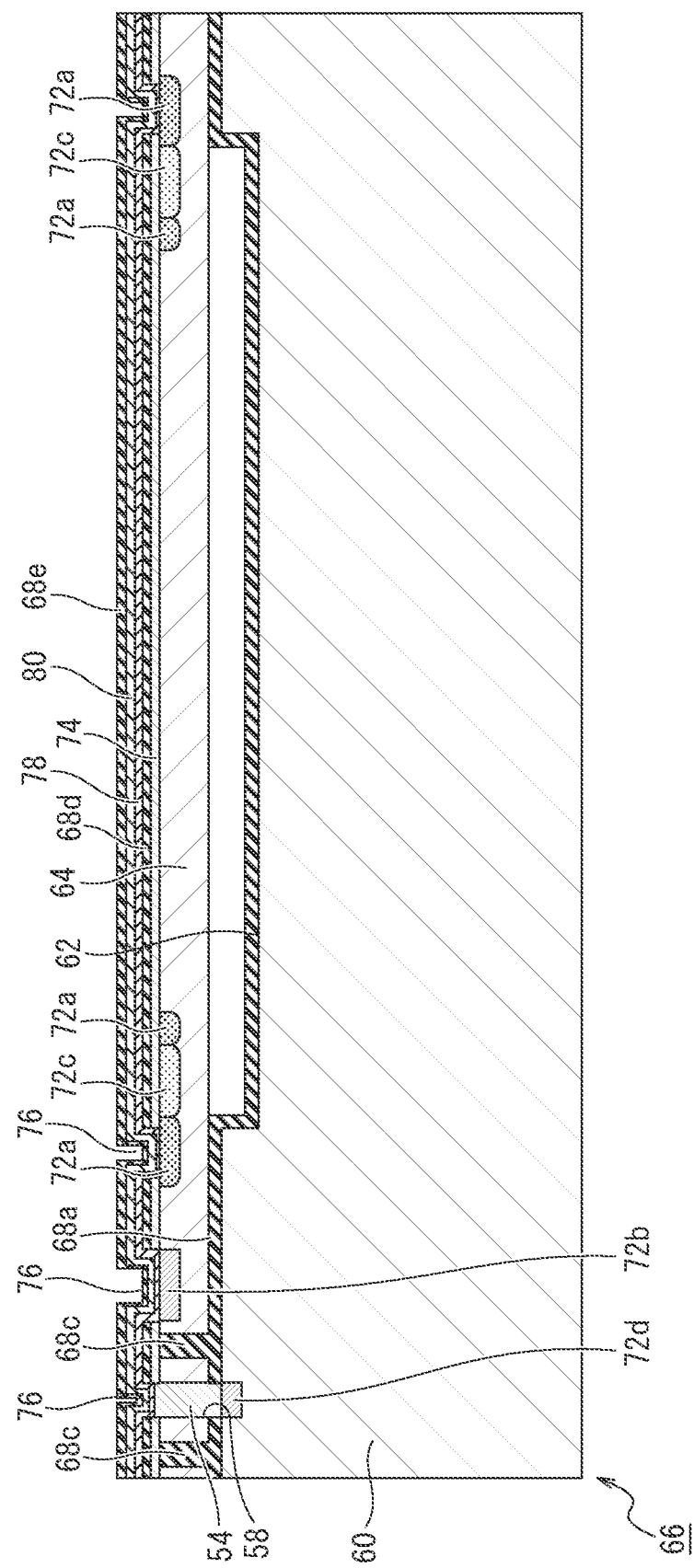
FIG. 25 is a diagram illustrating the wiring layer formation step.

Furthermore, as illustrated in FIG. 24, a metal film 80 of Al or the like is laminated on top of the laminated film 78 by sputtering. Then, as illustrated in FIG. 25, a fifth silicon oxide film 68e is laminated on top of the metal film 80.

Figure 26:
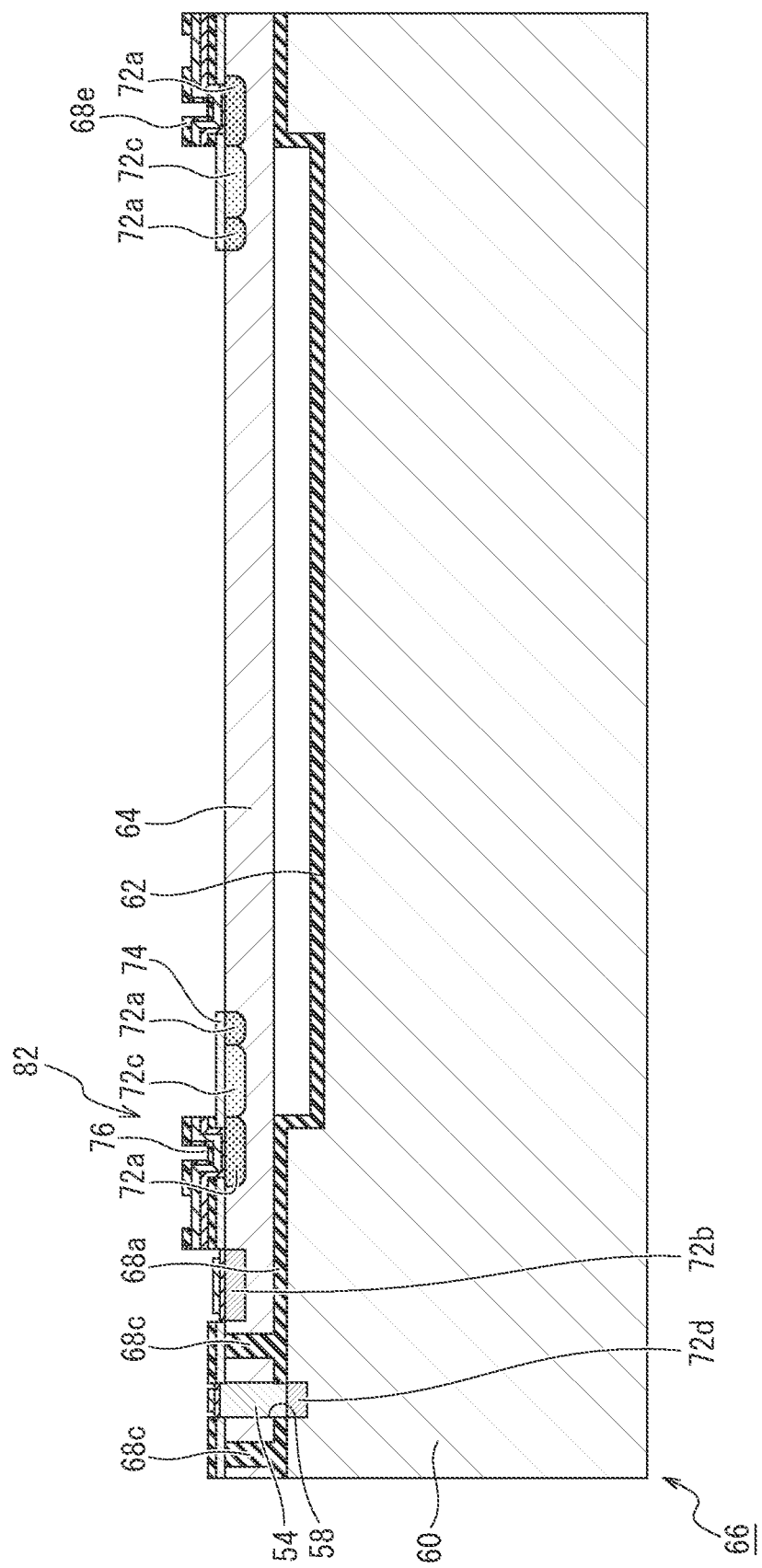
FIG. 26 is a diagram illustrating the wiring layer formation step.

Next, using the photolithography and etching technologies, the laminated film 78, the metal film 80, and the fifth silicon oxide film 68e are patterned to form a wiring layer 82 as illustrated in FIG. 26. Then, a pattern of photoresist (not illustrated) is formed to cover other than a membrane setting area, which is a preset area (an area that later becomes a membrane) including the center of the detection substrate. Furthermore, the third silicon oxide film 68c and the second silicon oxide film 68b having been formed in the membrane setting area are removed using etching technology. Then, a pattern of photoresist (not illustrated) is formed to cover other than the membrane setting area, and the silicon nitride film 74 in the membrane setting area is removed as illustrated in FIG. 26.

As described above, in the wiring layer formation step, the wiring layer 82, which includes the first terminal 50a electrically connected to the membrane 22 and the second terminal 50b electrically connected to the support substrate 10, is formed. In addition to this, the wiring layer 82, which includes the third terminal 50c electrically connected to the coupling portion 26b and the fourth terminal 50d electrically connected to the coupling portion 26a, is formed.

(Removal Step)

In the removal step, a part of the membrane setting area is cut out by etching to thereby pattern the four coupling portions 26a to 26d, which form two pairs. That is, in the removal step, the membrane 22, the fixing member 24, the coupling portions 26, and the flexible resistors 28 are formed by removing an area around the membrane setting area excluding the first low-resistance areas 72a.

(Receptor Formation Step)

In the receptor formation step, a PEI solution or the like is applied to a preset area including the center of the membrane 22, and dried. This forms the receptor 30 that undergoes a deformation depending on a substance adsorbed thereon.

(Operation and Action)

Figure 27:
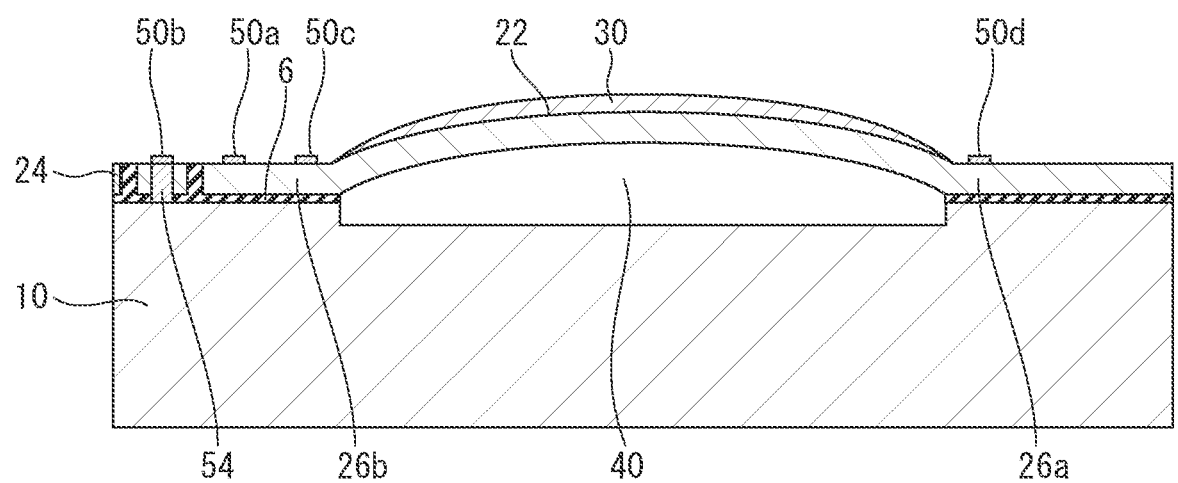
FIG. 27 is a diagram illustrating operation and action of the gas sensor of the first embodiment.

Operation and action of the first embodiment are explained using FIG. 27, while referring to FIGS. 1 to 26. When the gas sensor 1 is used as an olfactory sensor, for example, the receptor 30 is placed in an atmosphere of gas containing an odor component, and the odor component contained in the gas is adsorbed onto the receptor 30 as a measurement target. When the molecules of the gas (measurement target) are adsorbed on the receptor 30, and a strain occurs in the receptor 30, a surface stress is applied to the membrane 22 and the membrane 22 bends, as illustrated in FIG. 27. The fixing member 24 is formed in a parallel cross shape to surround the membrane 22, and the coupling portions 26 couple the membrane 22 and the fixing member 24 together at both ends. Therefore, one end of the coupling portion 26 which is coupled to the membrane 22 makes a free end, and the other end which is connected to the fixing member 24 makes a fixed end.

Accordingly, when the membrane 22 bends, the resistance value of each flexible resistor 28 varies due to deflections of the coupling portions 26 according to a strain occurred in the receptor 30. Then, by determining whether or not a pattern of a current according to the resistance value that has varied matches a response pattern stored in the pattern storage unit 201, the component of the measurement target is determined to detect the measurement target. Here, if the gas sensor 1 is faulty or if the operation of the membrane 22 is faulty, the pattern of the current according to the varied resistance value of the flexible resistor 28 does not match the response pattern, making it difficult to determine the component of the measurement target.

In regard to this, the gas sensor 1 of the first embodiment includes the first terminal 50a that can apply the first potential to the membrane 22 and the second terminal 50b that can apply the second potential to the support substrate 10. Accordingly, the membrane 22 is caused to deform by a Coulomb force generated by applying electric potentials to the first and second terminals 50a and 50b, without causing the receptor 30 to adsorb a gas or any other fluid. Hence, by measuring a resistance value variation (variation in piezoresistance) that occurs when the membrane 22 is deformed, it is possible to detect a fault without requiring adhesion of a fluid containing a measurement target to the receptor or application of a mechanical stress. The first embodiment described above is one example of the present invention, and the present invention is not limited to the first embodiment described above, and various changes can be made in accordance with design, etc., even by other forms than this embodiment, as long as they do not deviate from the technical ideas of the present invention.

(Advantageous Effects of First Embodiment)

The gas sensor 1 of the first embodiment can achieve the advantageous effects described below.

(1) The gas sensor includes the conductive membrane 22 that bends with an applied surface stress, the conductive fixing member 24 that surrounds the membrane 22, and the conductive coupling portions 26 that couple the membrane 22 to the fixing member 24. The gas sensor further includes the flexible resistors 28 whose resistance value vary in accordance with a deflection occurring in the coupling portions 26, and the conductive support substrate 10 connected to the fixing member 24 and located with a gap (gap 40) between the membrane 22 and the coupling portions 26, and overlapping with the membrane 22 and the coupling portions 26. In addition, the receptor 30, which is formed on the area including the center of the surface of the membrane 22 and deforms in accordance with adsorbed substance, is included. Further, the first terminal 50a that can apply the first potential to the membrane 22, the second terminal 50b that can apply the second potential to the support substrate 10, and the insulating portions 6 that electrically insulate the fixing member 24 from the support substrate 10 are included.

Therefore, the membrane 22 can be caused to deform by a Coulomb force generated by applying electric potentials to the first and second terminals 50a and 50b without causing the receptor 30 to adsorb a gas or any other fluid. This makes it possible to detect a fault by measuring a resistance value variation occurred when the membrane 22 is deformed, without requiring adhesion of a fluid containing a measurement target to the receptor or application of a mechanical stress. Hence, it is possible to provide the gas sensor 1 that can detect a fault without requiring adhesion of a fluid containing a measurement target to the receptor 30 or application of a mechanical stress.

(2) The membrane 22 deforms in accordance with a voltage applied between the first and second terminals 50a and 50b. Therefore, it is possible to provide the gas sensor 1 that can detect a fault by applying a voltage between the first terminal 50a and the second terminal 50b without requiring adhesion of a fluid containing a measurement target to the receptor 30 or application of a mechanical stress.

(3) The gas sensor further includes the resistance detection unit 104 that detects the inspection-time resistance value, which is the resistance value of the flexible resistor 28 with a voltage being applied between the first and second terminals 50a and 50b. Therefore, it is possible to detect the inspection-time resistance value used to detect a fault in the gas sensor 1, without requiring adhesion of a fluid containing a measurement target to the receptor 30 or application of a mechanical stress.

(4) The gas sensor further includes the voltage application unit (first power supply 102, multiplexer 101) that can apply a voltage between the first terminal 50a and the second terminal 50b. Therefore, it is possible to detect the inspection-time resistance value used to detect a fault in the gas sensor 1, without requiring adhesion of a fluid containing a measurement target to the receptor 30 or application of a mechanical stress.

(5) The gas sensor further includes the correction value storage unit 105 that stores the sensitivity correction value and the inspection-time resistance value, and the sensitivity correction unit 106 that corrects the inspection-time resistance value stored in the correction value storage unit 105 in accordance with the sensitivity correction value stored in the correction value storage unit 105. Therefore, it is possible to improve, by adjusting the sensitivity correction unit 106 after a fault of the gas sensor 1 is detected, the accuracy of detection of a measurement target performed after the sensitivity correction unit 106 is adjusted.

(6) At least one of the membrane 22, the fixing member 24, the coupling portions 26, and the support substrate 10 is made of a laminated substrate or a semiconductor substrate formed by layering conductors on an insulating substrate. Therefore, it is possible to electrically insulate the support substrate 10 from the detection substrate 20 by at least one of the membrane 22, the fixing member 24, the coupling portions 26, and the support substrate 10 in addition to the insulating portion 6.

(7) The gas sensor further includes the receptor 30 formed on the area including the center of the surface on one side of the membrane 22 opposite to the other side facing the support substrate 10, and deforming in accordance with an adsorbed substance. As a result, it is possible to form the gas sensor 1 that is capable of detecting a measurement target adsorbed on the receptor 30.

(8) The insulating portion 6 is formed using a silicon oxide film provided between the fixing member 24 and the support substrate 10. Therefore, it is possible to form the insulating portion 6 using a material easy to obtain and process. In addition, the component detection apparatus of the first embodiment (gas sensor 1, resistance detection unit 104, component detector 200) can achieve the advantageous effects described below.

(9) The component detection apparatus includes the gas sensor 1, the resistance detection unit 104 that detects the inspection-time resistance value, and the pattern storage unit 201 that stores a response pattern with which the receptor 30 responds for a component contained in a fluid when the fluid adheres to the receptor. In addition, the component detection apparatus includes the component detector 200 that detects a component contained in a fluid adhered to the receptor 30 in accordance with the inspection-time resistance value and the response pattern. Therefore, it is possible to detect a component contained in a fluid adhered to the receptor 30 in accordance with the detected resistance value and the response pattern stored in advance. In addition, the inspection system of the first embodiment (the gas sensor 1, the voltage application unit, and the resistance detection unit) can achieve the advantageous effects described below.

(10) The inspection system includes the gas sensor 1, the voltage application unit that can apply a voltage between the first and second terminals 50a and 50b, and the resistance detection unit 104 that detects the inspection-time resistance value, which is the resistance value of the flexible resistor 28 when the voltage is applied between the first and second terminals 50a and 50b. Therefore, it is possible to detect the inspection-time resistance values used to detect a fault in the gas sensor 1, without requiring adhesion of a fluid containing a measurement target to the receptor 30 or application of a mechanical stress.

(11) The inspection system includes the correction value storage unit 105 that stores the sensitivity correction value and the inspection-time resistance value, and the sensitivity correction unit 106 that corrects the inspection-time resistance value stored in the correction value storage unit 105 in accordance with the sensitivity correction value stored in the correction value storage unit 105. Therefore, it is possible to improve, by adjusting the sensitivity correction unit 106 after a fault of the gas sensor 1 is detected, the accuracy of detection of the fault of the gas sensor 1 performed after the sensitivity correction unit 106 is adjusted. In addition, the inspection method for the gas sensor 1 of the first embodiment can achieve the advantageous effects described below.

(12) The inspection method includes the second voltage application step of applying the second voltage between the first terminal 50*a* and the second terminal 50*b*, and the inspection-time resistance detection step of detecting the inspection-time resistance value, which is the resistance value of the flexible resistor 28 with the second voltage being applied between the first terminal 50*a* and the second terminal 50*b*. In addition, the inspection method includes the determination step of determining the operation of the membrane 22 based on the inspection-time resistance value detected in the inspection-time resistance detection step and the reference resistance value, which is the resistance value with the first voltage different from the second voltage being applied between the first terminal 50*a* and the second terminal 50*b*. Therefore, it is possible to detect faulty operation of the membrane 22 without requiring adhesion of a fluid containing a measurement target to the receptor 30 or application of a mechanical stress.

(13) The inspection method further includes are the first voltage application step of applying the first voltage between the first terminal 50*a* and the second terminal 50*b* and the measurement step of measuring the reference resistance value with the first voltage being applied between the first terminal 50*a* and the second terminal 50*b* in the first voltage application step, as a pre-step of the second voltage application step. Therefore, it is possible to detect the reference resistance value used to detect a fault in the gas sensor 1, without requiring adhesion of a fluid containing a measurement target to the receptor 30 or application of a mechanical stress.

(14) The inspection method includes the correction value calculation step of calculating, when the operation of the membrane 22 is determined to be better than the reference value in the determination step, the sensitivity correction value, which is a correction value of sensitivity according to the inspection-time resistance value detected in the inspection-time resistance detection step. In addition, the inspection method includes the correction value storage step of storing the sensitivity correction value calculated in the correction value calculation step, and the inspection-time resistance value correction step of correcting the inspection-time resistance value using the sensitivity correction value stored in the correction value storage step. Therefore, it is possible to improve, by adjusting the sensitivity correction unit 106 after a fault of the gas sensor 1 is detected, the accuracy of detection of the fault of the gas sensor 1 performed after the sensitivity correction unit 106 is adjusted. In addition, the gas sensor manufacturing method of the first embodiment can achieve the advantageous effects described below.

(15) The gas sensor manufacturing method includes the laminate formation step, the through-electrode formation step, the first ion implantation step, the second ion implantation step, the third ion implantation step, the low-resistance area formation step, the removal step, and the wiring layer formation step. The laminate formation step is a step for forming the recess 62 on one side of the support substrate 10, and forming the insulating portion 6 on the other side. Furthermore, the laminate formation step is a step for forming the laminate 66 with the gap 40 between the support substrate 10 and the detection substrate 20 by laminating the detection substrate 20 so as to cover the part of the support substrate 10, on which the insulating portion 6 has been formed. The through-electrode formation step is a step for forming a through-hole 58 that penetrates into the support substrate 10 from the surface on one side of the detection substrate 20, which is opposite to the other side facing the support substrate 10, by removing a part of the detection substrate 20 and the insulating portion 6. Furthermore, the through-electrode formation step is a step for forming the through-electrode 54 that reaches from the surface to the support substrate 10 by burying the through-hole 58 with an electrode material containing impurities. The first ion implantation step is a step for implanting the first ions into a selected partial area of the surface of the detection substrate 20, which is outside a preset area that includes the center of the detection substrate 20. The second ion implantation step is a step for implanting the second ions into a selected area of the detection substrate 20, which is outside the area where the first ions have been implanted. The third ion implantation step is a step for implanting the third ions into a preset area of the surface of the detection substrate 20. The low-resistance area formation step is a step for forming the first low-resistance areas 72*a* in the area where the first ions have been implanted, the second low-resistance area 72*b* in the area where the second ions have been implanted, and the third low-resistance areas 72*c* in the area where the third ions have been implanted, by heat-treating the laminate 66. Furthermore, the low-resistance area formation step is a step for forming the fourth low-resistance area 72*d* in a preset area of one side of the support substrate 10, which faces the detection substrate 20, by solid-phase diffusing impurities from the through-electrode 54 into the support substrate 10. The removal step is a step for forming the membrane 22, the fixing member 24, and at least one pair of the coupling portions 26, by removing an area around a preset area including the center of the detection substrate 20 and excluding the first low-resistance areas 72*a*. The wiring layer formation step is a step for forming the wiring layer 82 that includes the first terminal 50*a* electrically connected to the membrane 22 and the second terminal 50*b* electrically connected to the support substrate 10.

Therefore, it is possible to detect a fault, without causing the receptor 30 to adsorb a gas or any other fluid, by applying electric potentials to the first and second terminals 50*a* and 50*b*, without requiring adhesion of a fluid containing a measurement target to the receptor 30 or application of a mechanical stress. Therefore, it is possible to provide a manufacturing method for the gas sensor 1 that can detect a fault without requiring adhesion of a fluid containing a measurement target to the receptor or application of a mechanical stress.

(Variation of First Embodiment)

(1) In the first embodiment, the insulating portion 6 that electrically insulates the fixing member 26 from the support substrate 10 is formed using a silicon oxide film provided between the fixing member 26 and the support substrate 10, however, it is not limited to this. That is, the detection substrate 20 and the support substrate 10 may be configured to have different polarities from each other, and the insulating portion that electrically insulates the fixing member 26 from the support substrate 10 may be formed using a depletion layer formed between the detection substrate 20 and the support substrate 10. In this case, N type silicon is used as a material to form the support substrate 10, P type silicon is used as a material to form the detection substrate 20, and the depletion layer formed by the support substrate 10 and the detection substrate 20 is used to form the insulating portion. Since P type silicon is used as a material to form the detection substrate 20, the second low-resistance area 72*b* becomes a P++ type semiconductor layer. This configuration increases the number of choices of materials to form the support substrate 10 and the detection substrate 20, thus expanding the application of the gas sensor 1.

(2) In the first embodiment, the gas sensor 1 is configured as a piezoresistive surface sensor in which the flexible resistor 28 is formed of a piezoresistive resistance, but it is not limited to this. For example, as illustrated in FIG. 28, the gas sensor 1 may be configured as a capacitive sensor, in which the gap 40 serves as a space for forming a capacitance between the support substrate 10 and a set of the membrane 22, coupling portion 26. In this case, for example, as illustrated in FIG. 28, a current detection unit 300 is connected to the first and second terminals 50*a* and 50*b* to detect a current flowing through the first and second terminals 50*a* and 50*b*. The current detection unit 300 includes a detection resistor 301, an inspection power supply 302, and a current detection circuit 303. In this configuration, by detecting a current when a DC voltage and a small-amplitude AC voltage are applied between the first and second terminals 50*a* and 50*b*, it is possible to detect a capacitance variation to detect a fault.

For example, as illustrated in FIG. 29, an internal electrode 400 may be formed in the gap 40, and the current detection unit 300 that detects a current flowing through the first terminal 50*a* and the internal electrode 400 may be connected to the first terminal 50*a* and the internal electrode 400. In this case, the detection resistor 301 is connected to the first terminal 50*a* and the second terminal 50*b*, and the inspection power supply 302 and the current detection circuit 303 are connected to the first terminal 50*a* and the internal electrode 400. In this configuration, a fault can be detected by detecting a capacitance variation between the first terminal 50*a* and the second terminal 50*b* when a DC voltage is applied between the first terminal 50*a* and the internal electrode 400.

(3) In the first embodiment, the second terminal 50*b* is electrically connected to the support substrate 10 via the through-electrode 54, however, it is not limited to this configuration. That is, for example, as illustrated in FIG. 30, the second terminal 50*b* may be formed on one side of the support substrate 10, which is opposite to the other side facing the detection substrate 20, so that it is configured to be electrically connected to the support substrate 10. Although omitted from illustration, the second terminal 50*b* may be formed on the lateral side of the support substrate 10, so that it is configured to be electrically connected to the support substrate 10.

(4) In the first embodiment, the gap 40 is formed between the membrane 22 and the support substrate 10 by forming the recess 62 on one side of the first silicon substrate 60, which becomes a material of the support substrate 10, however, it is not limited to this. That is, the gap 40 may be formed between the membrane 22 and the support substrate 10 by forming a recess on one side of the second silicon substrate 64 which becomes a material of the detection substrate 20, the one side facing the support substrate 10.

(5) In the first embodiment, the area of the connecting portion 4 is smaller than the area of the membrane 22 when viewed from the direction of the thickness of the membrane 22, however, it is not limited to this. The area of the connecting portion 4 is equal to or larger than the area of the membrane 2.

(6) In the first embodiment, the connecting portion 4 is circular shaped, however, it is not limited to this, and the shape of the connecting portion 4 may be, for example, rectangular. Furthermore, two or more connecting portions 4 may be formed.

(7) In the first embodiment, the material to form the detection substrate 20 and the material to form the support substrate 10 are the same, however, they are not limited to this, and the material to form the detection substrate 20 and the material to form the support substrate 10 may be different from each other. In this case, it is possible to reduce the difference between the amount of deformation of the detection substrate 20 and the amount of deformation of the support substrate 10, which depend on deformation of the package substrate 2, by setting the difference between the coefficient of linear expansion of the detection substrate 20 and the coefficient of linear expansion of the support substrate 10 to $1.2\times10^{-5}/^\circ$ C. or less. This makes it possible to suppress the deflection of the membrane 22.

(8) In the first embodiment, the coefficient of linear expansion of the support substrate 10 is $5.0\times10^{-6}/^\circ$ C. or less, however, it is not limited to this, and the coefficient of linear expansion of the support substrate 10 may be $1.0\times10^{-5}/C$ or less. Even in this case, it is possible to improve the rigidity of the support substrate 10 and reduce the amount of deformation of the detection substrate 20, which depends on the deformation of the package substrate 2 caused by a temperature variation, etc.

(9) In the first embodiment, the fixing member 24 is configured as a quadrilateral (square) frame that surrounds the membrane 22 with a gap in between, however, it is not limited to this. That is, the fixing member 24 may be configured to be a quadrilateral shape other than a square, for example, a diamond shape. Furthermore, the fixing member 24 may be configured to be a discontinuous shape with a gap, for example, a shape of a quadrilateral, one side of which has been removed. That is, the fixing member 24 should be configured to be capable of supporting and fixing the membrane 22 from the outside.

(10) In the first embodiment, the inspection method for the gas sensor 1 includes the second voltage application step, the inspection-time resistance detection step, the determination step, the first voltage application step and the measurement step, however, it is not limited to this. That is, if the reference resistance value is known, the inspection method for the gas sensor 1 may not include the first voltage application step or the measurement step. In this case, in the determination step, the first voltage is set to 0 [V], and the second voltage is set to a value corresponding to the configuration of the gas sensor 1.

Second Embodiment

A second embodiment of the invention is described below with reference to the drawings.
(Configuration)
Since the configuration of the second embodiment is the similar as the first embodiment described above, the description is omitted.

(Gas Sensor Manufacturing Method)

A manufacturing method for the gas sensor 1 is explained using FIGS. 31 to 40, while referring to FIGS. 1 to 30. The cross-sectional views in FIGS. 31 to 40 correspond to the X-X line cross-sectional view of FIG. 2. The manufacturing method for the gas sensor 1 includes a laminate formation step, a through-electrode formation step, a first ion implantation step, a second ion implantation step, a third ion implantation step, a low-resistance area formation step, a hole formation step, a gap formation step, a hole sealing step, a removal step, and a wiring layer formation step.

(Laminate Formation Step)

In the laminate formation step, first, as illustrated in FIG. 31, an insulating sacrificial layer 92 formed using a silicon oxide film is laminated to a first silicon substrate 60, which becomes a material of a support substrate 10. Furthermore, a second silicon substrate 64, which becomes a material of a detection substrate 20, is layered on the sacrificial layer 92. As the sacrificial layer 92, other than a silicon oxide film, a silicon nitride film or a metal film of aluminum, titanium, copper, or tungsten may be used. As described above, in the laminate formation step, the insulating sacrificial layer 92 is laminated to the support substrate 10, and the detection substrate 20 is further laminated to the insulating sacrificial layer 92 to form a laminate 66.

(Through-Electrode Formation Step)

Figure 32A:
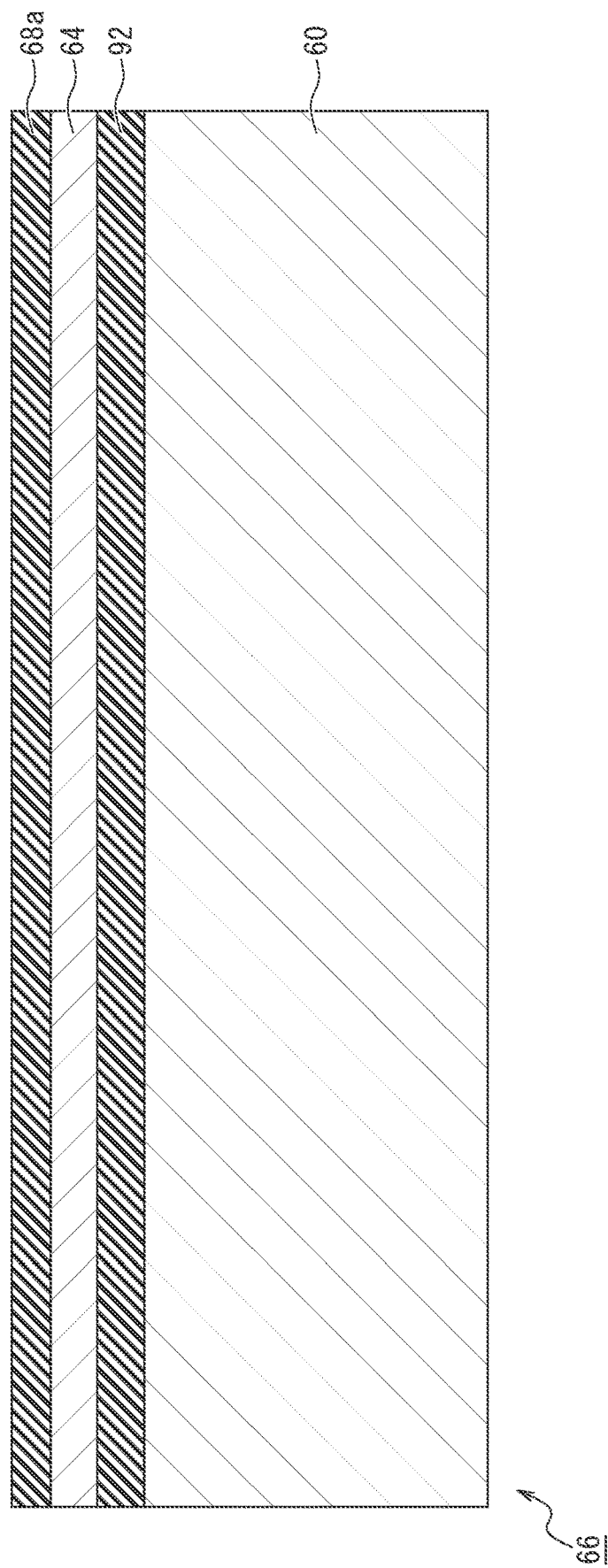
FIG. 32A is a diagram illustrating a through-electrode formation step.

In the through-electrode formation step, first, as illustrated in FIG. 32A, a first silicon oxide film 68a is deposited on the surface on one side of the second silicon substrate 64, which is opposite to the other side facing the first silicon substrate 60. Next, as illustrated in FIG. 32B, two first trenches 56a are formed in the first silicon oxide film 68a using the lithography and etching technologies. The width of the first trench 56a (the length in the left-right direction in FIG. 32B) is set to, for example, 0.5 [mm]. In addition, as illustrated in FIG. 32C, using the first silicon oxide film 68a as a mask, two second trenches 56b are formed on the second silicon substrate 64 overlapping with the two first trenches 56a, respectively, using etching technology.

Figure 33A:
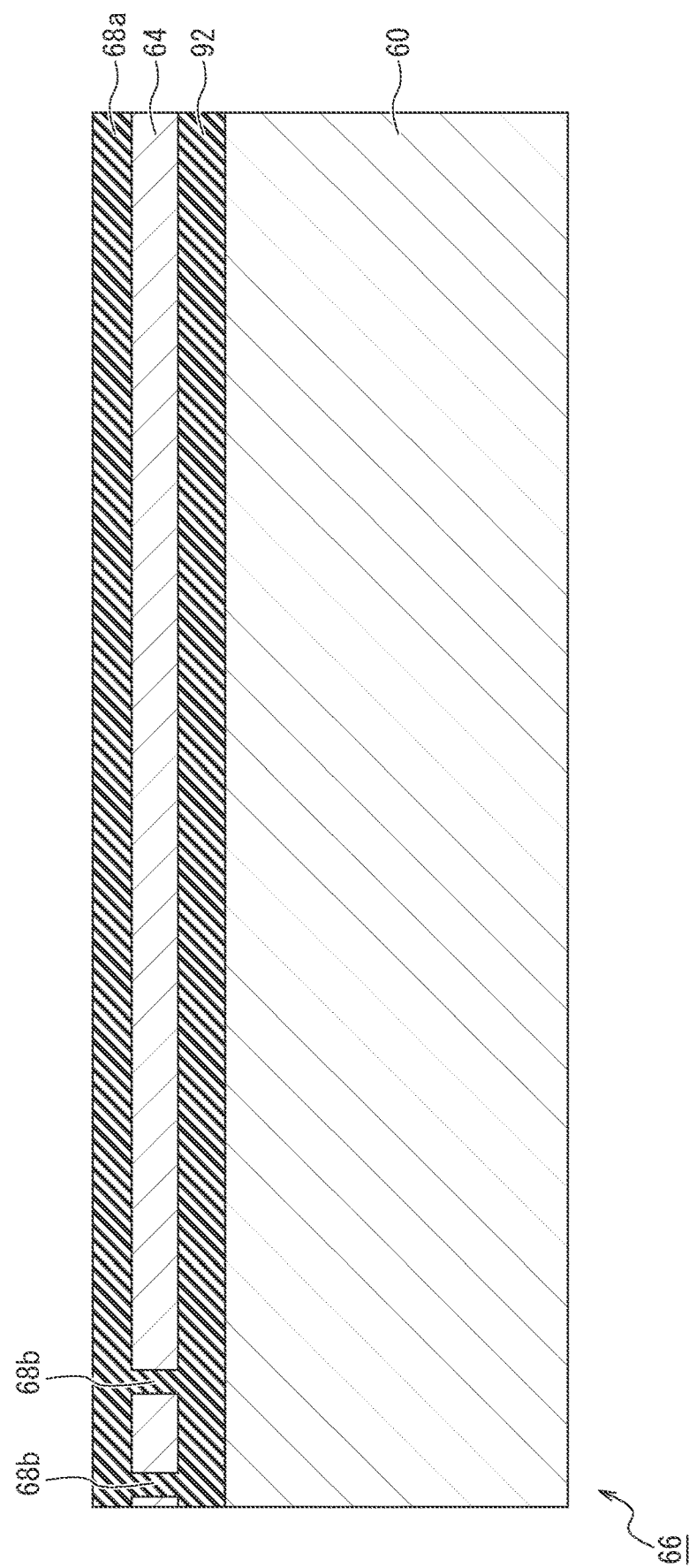
FIG. 33A is a diagram illustrating the through-electrode formation step.
Figure 33B:
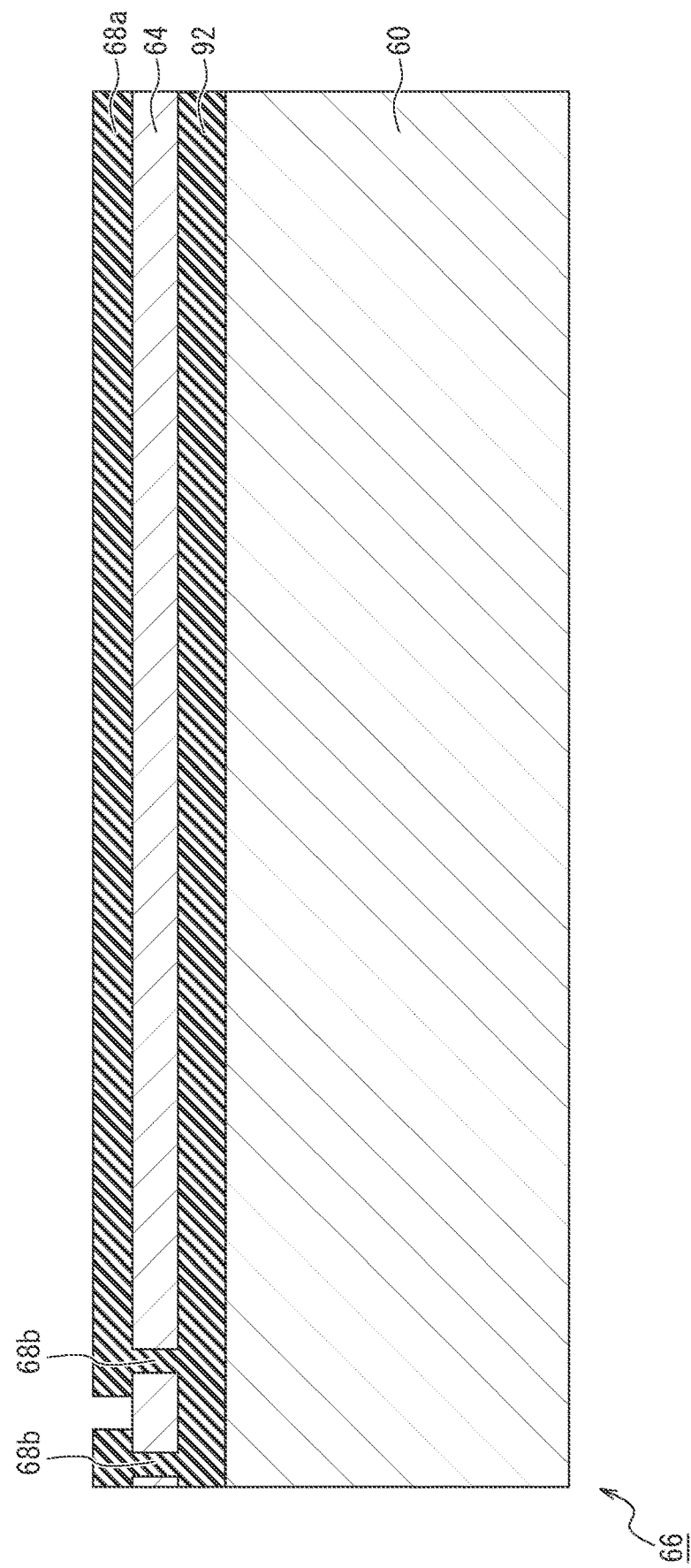
FIG. 33B is a diagram illustrating the through-electrode formation step.
Figure 33C:
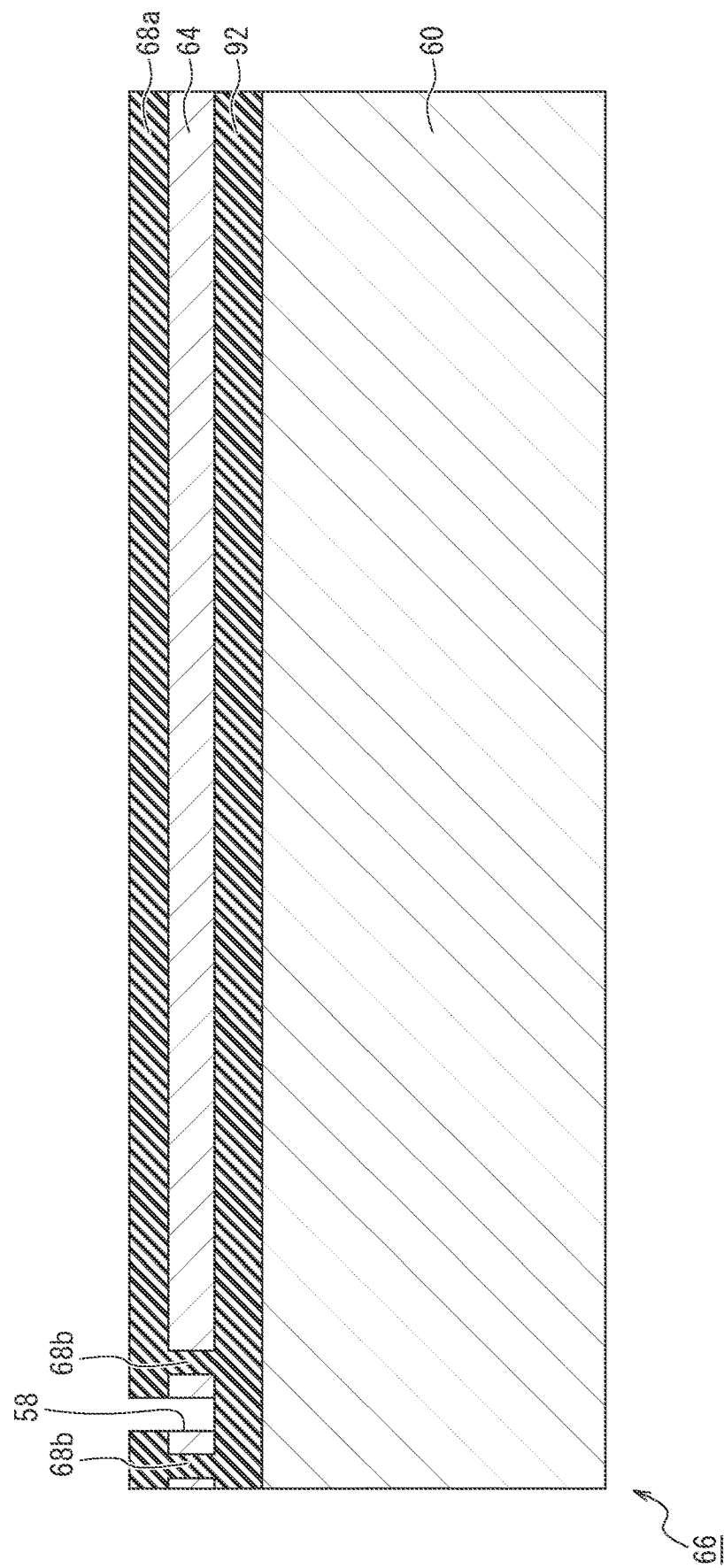
FIG. 33C is a diagram illustrating the through-electrode formation step.

Next, as illustrated in FIG. 33A, the laminate 66 is thermally oxidized (e.g., 300 [nm]) to seal the two first trenches 56a and the two second trenches 56b with a second silicon oxide film 68b. This prevents a short circuit between the second silicon substrate 64 and the first silicon substrate 60 after a through-electrode 54 is formed. Next, as illustrated in FIG. 33B and FIG. 33C, the lithography and etching technologies are used to remove a part of the first silicon oxide film 68a and the second silicon substrate 64, which exists between the two first trenches 56a and the two second trenches 56b. As a result, a through-hole 58 for forming the through-electrode 54 is formed.

Figure 34A:
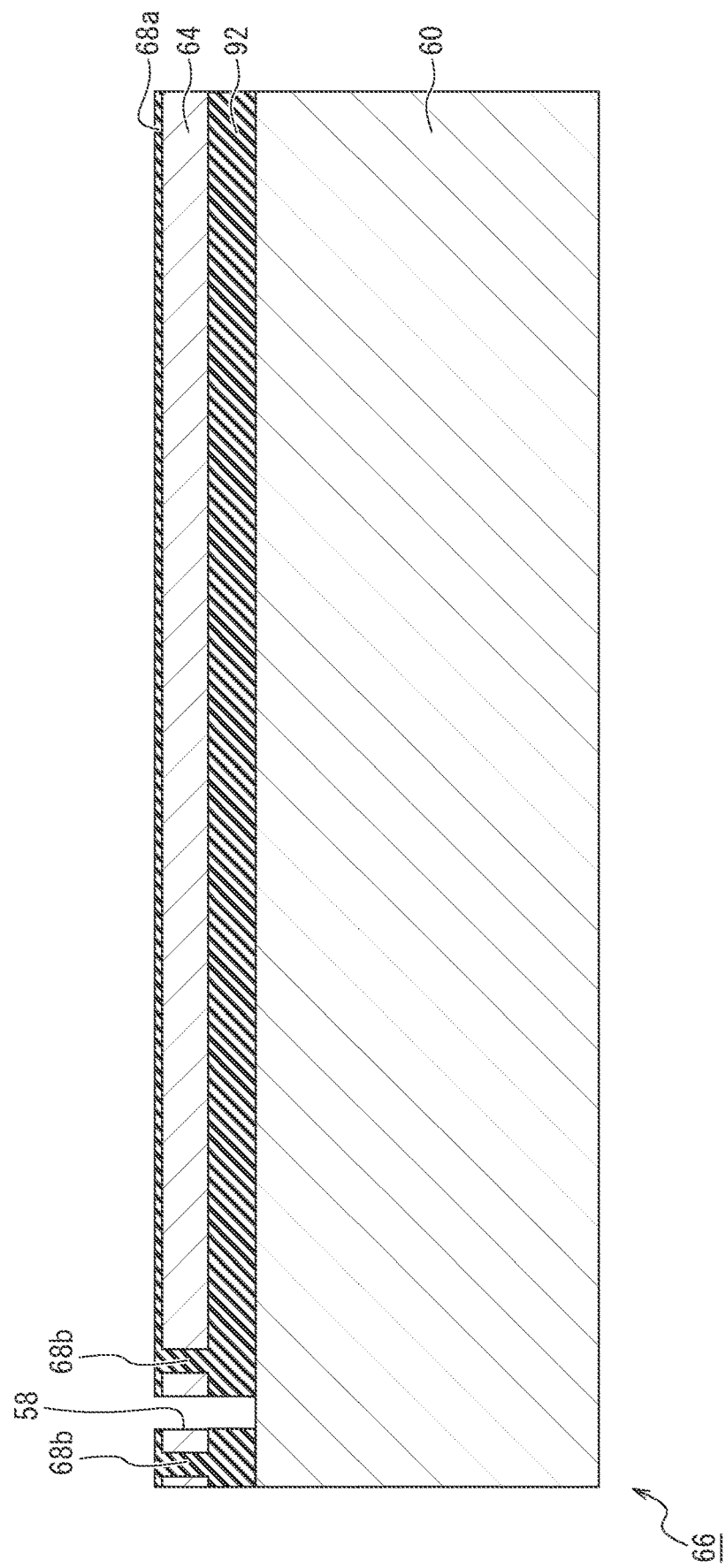
FIG. 34A is a diagram illustrating the through-electrode formation step.
Figure 34B:
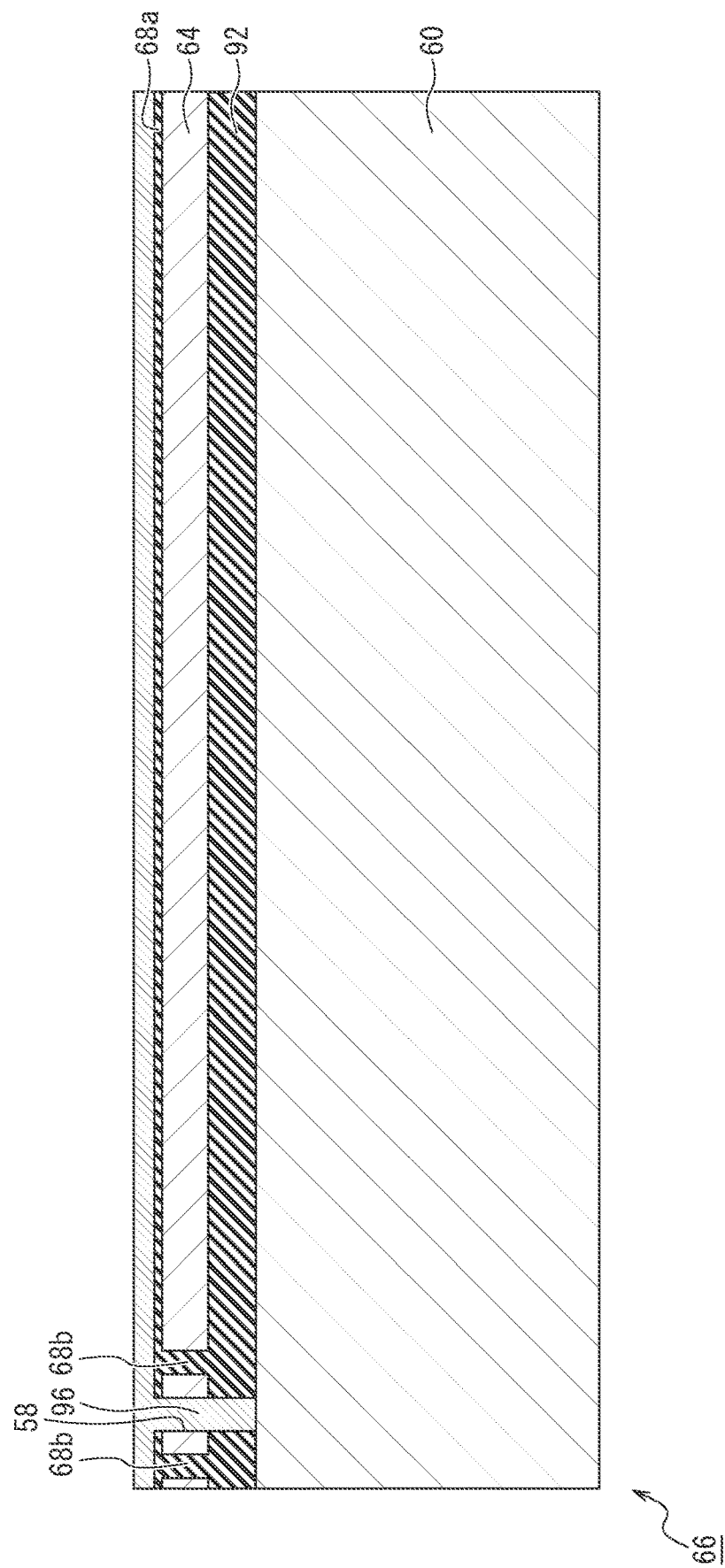
FIG. 34B is a diagram illustrating the through-electrode formation step.
Figure 34C:
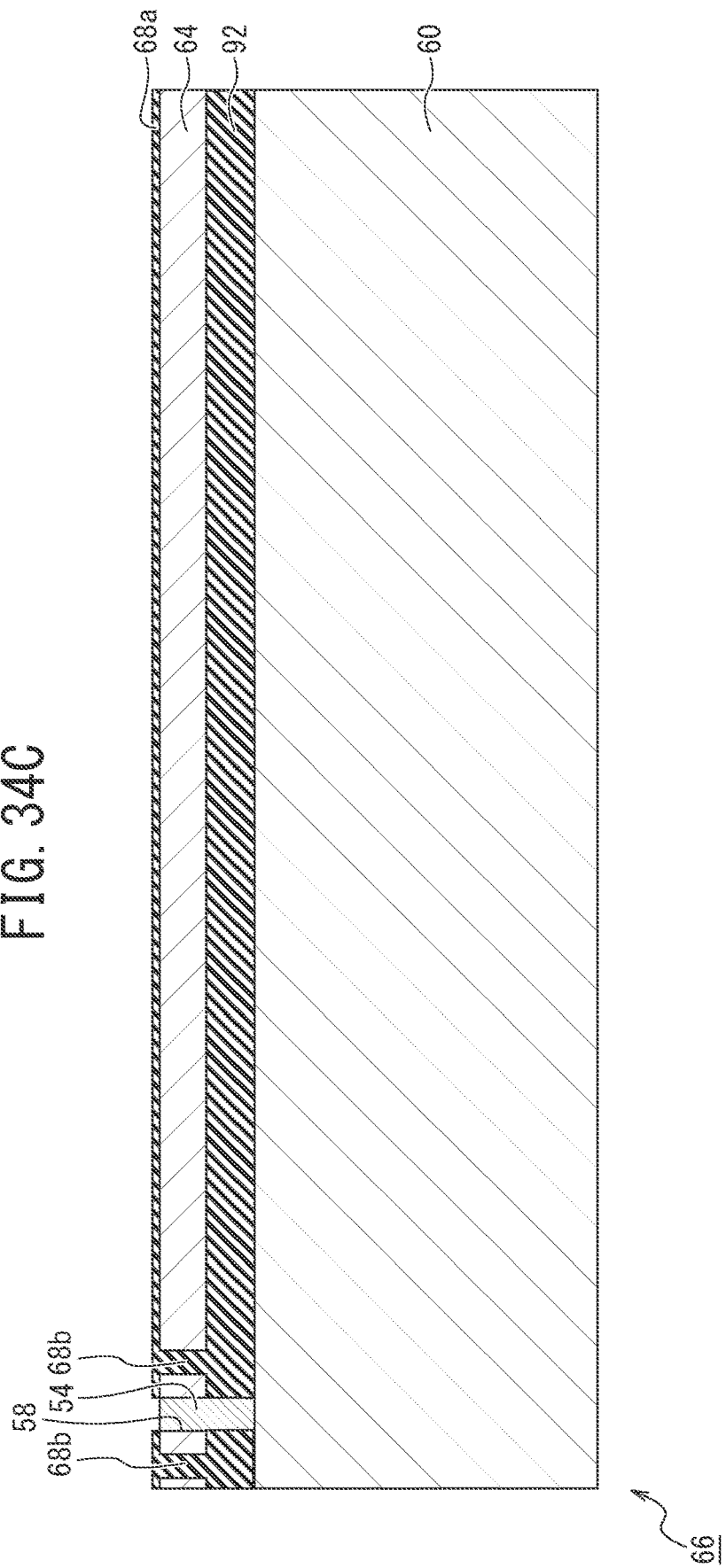
FIG. 34C is a diagram illustrating the through-electrode formation step.

In addition, as illustrated in FIG. 34A, a part of the sacrificial layer 92 formed on the first silicon substrate 60, which is continuous with the through-hole 58, and a part of the first silicon oxide film 68a formed on the second silicon substrate 64 are etched away. At this time, the thickness of the first silicon oxide film 68a is about 50 [nm]. Next, as illustrated in FIG. 34B, a film of N type polysilicon 96 is formed as an electrode material containing impurities. At this time, the inside of the through-hole 58 is filled with the N type polysilicon 96. In addition, as illustrated in FIG. 34C, unnecessary N type polysilicon 96 is removed by etching (or chemical mechanical polishing). As a result, the through-electrode 54 formed of N type polysilicon is provided inside the through-hole 58.

As described above, in the through-electrode formation step, apart of the detection substrate 20 and the insulating portion 6 is removed to form the through-hole 58 that penetrates into the support substrate 10 from the surface on one side of the detection substrate 20, which is opposite to the other side facing the support substrate 10. In addition, in the through-electrode formation step, the through-hole 58 is buried with an electrode material containing impurities to form the through-electrode 54 that reaches from the surface of the detection substrate 20 to the support substrate 10.

(First Ion Implantation Step)

In the first ion implantation step, first, the first silicon oxide film 68a is removed, and then a third silicon oxide film 68c is formed on the surface of the second silicon substrate 64. Then, as illustrated in FIG. 35, using a photoresist pattern (not illustrated), first ions are implanted into selected partial areas (first ion implantation areas 70a) of the surface of the detection substrate 20, which is outside a preset area that includes the center of the detection substrate 20. As the first ions, ions that cause the first ion implantation areas 70a to become P++ type semiconductor layers by heat treatment is used. Therefore, in the first ion implantation step, the first ions are implanted into the selected partial areas (the first ion implantation areas 70a) of the surface of the detection substrate 20, which are outside the preset area that includes the center of the detection substrate 20.

(Second Ion Implantation Step)

In the second ion implantation step, as illustrated in FIG. 35, second ions are implanted into a selected area (a second ion implantation area 70b) of the detection substrate 20, which is outside the area where the first ions have been implanted (the first ion implantation areas 70a). As the second ions, ions that cause the second ion implantation area 70b to become an N++ type semiconductor layer by heat treatment is used.

(Third Ion Implantation Step)

In the third ion implantation step, as illustrated in FIG. 35, third ions are implanted into preset areas (third ion implantation areas 70c) of the surface of the detection substrate 20, which are inside the first ion implantation areas 70a. As the third ions, ions that cause the third ion implantation areas 70c to become P+ type semiconductor layers by heat treatment is used.

(Low-Resistance Area Formation Step)

Figure 36:
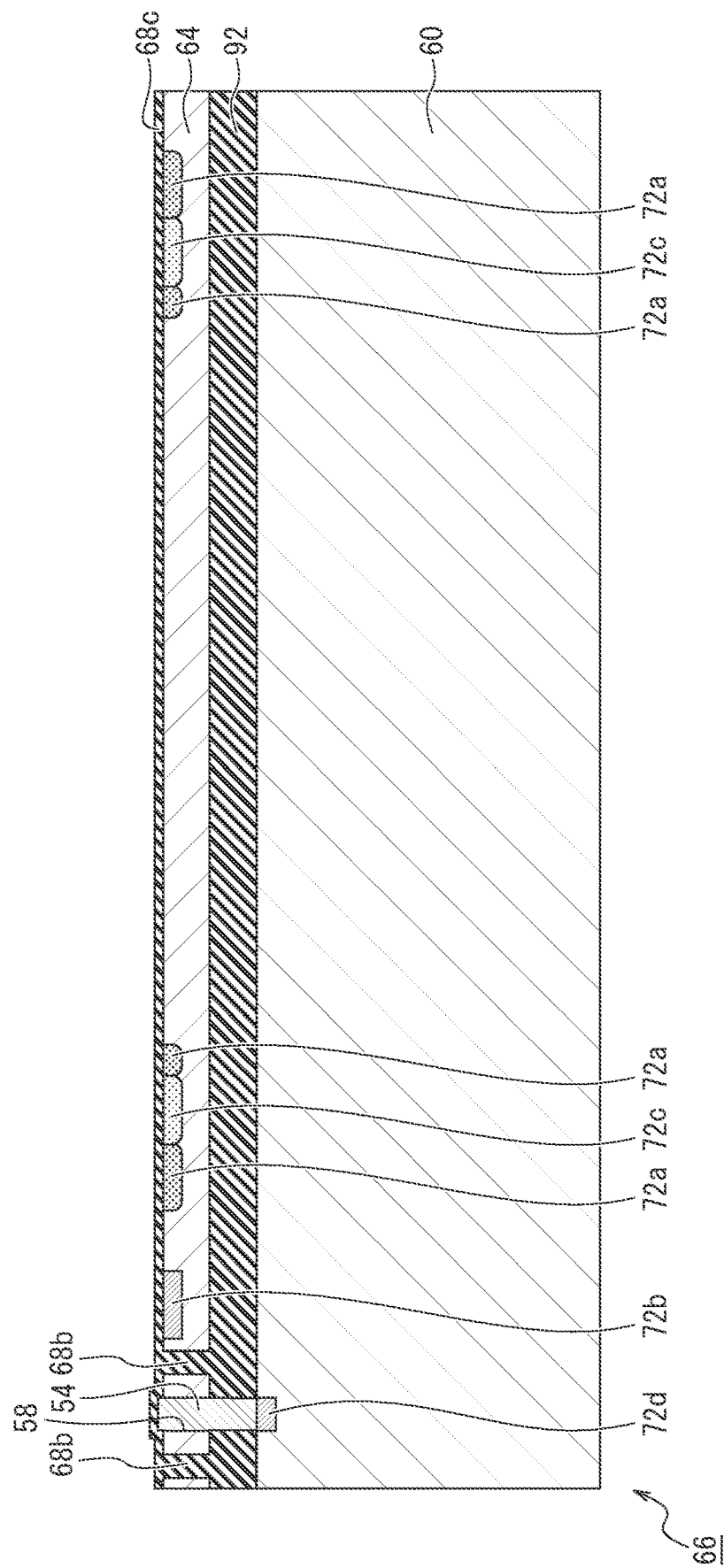
FIG. 36 is a diagram illustrating a low-resistance area formation step.

In the low-resistance area formation step, the laminate 66 is subjected to heat treatment (annealing process). This performs activation of the ions implanted in the first, second and third ion implantation steps, and also solid phase diffusion of impurities (carriers) from the through-electrode 54 formed of N type polysilicon into the support substrate 10. Then, the second silicon oxide film 68b is removed. Subjecting the laminate 66 to heat treatment forms first low-resistance areas 72a (P++ type semiconductor layers), a second low-resistance area 72b (an N++ type semiconductor layer), and third low-resistance areas 72c (P+ type semiconductor layers) on the surface of the detection substrate 20, as illustrated in FIG. 36. In addition, a fourth low-resistance area 72d (an N++ type semiconductor layer) is formed in a part of the support substrate 10.

The first low-resistance areas 72a are a preset areas of the surface of the second silicon substrate 64. Specifically, the first low-resistance areas 72a are areas area where the coupling portions 26 are formed later. The second low-resistance area 72b is a preset area of the surface of the second silicon substrate 64. Specifically, the second low-resistance area 72b is an area where the first terminal 50a is formed later. The third low-resistance areas 72c are areas set inside the second low-resistance area 72b. Specifically, the third low-resistance areas 72c are areas where the flexible resistors 28 are formed later. The fourth low-resistance area 72d is a preset area of the surface on a side of the first silicon substrate 60, which faces the second silicon substrate 64. Specifically, the fourth low-resistance area 72d is an area where the second terminal 50b is formed later.

As described above, in the low-resistance area formation step, the first low-resistance areas 72a, the second low-resistance area 72b, and the third low-resistance areas 72c are formed on the detection substrate 20 by heat-treating the ion-implanted laminate 66. Furthermore, by heat-treating the laminate 66 formed with the through-electrode 54, impurities are solid-phase diffused from the through-electrode 54 into the support substrate 10 to thereby form the fourth low-resistance area 72d in the preset area of the surface on the side of the support substrate 10, which faces the detection substrate 20.

(Hole Formation Step)

Figure 37:
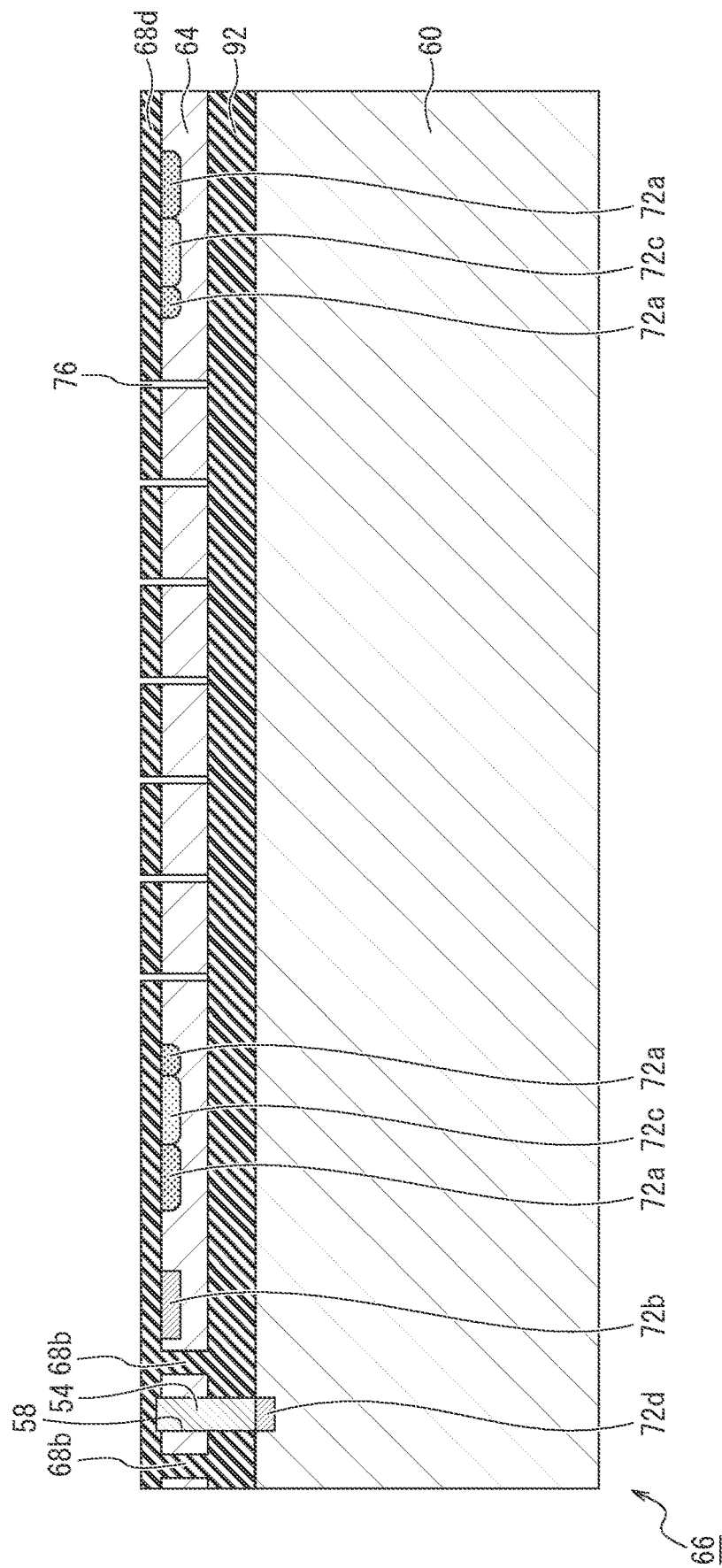
FIG. 37 is a diagram illustrating a hole formation step.

In the hole formation step, first, a fourth silicon oxide film 68d is formed on the surface of the second silicon substrate 64 after the third silicon oxide film 68c is removed, as illustrated in FIG. 37. Then, a hole pattern (not illustrated) is formed on the upper side of the second silicon substrate 64 using general photolithography technology. Next, dry etching is applied using the hole pattern as a mask to form holes 76 in the fourth silicon oxide film 68d and the second silicon substrate 64, as illustrated in FIG. 37. The diameter of the holes 76 is set to 0.28 [μm], for example, and to a depth that reaches the sacrificial layer 92. As described above, in the hole formation step, the holes 76 that penetrate into the sacrificial layer 92 are formed in a preset area of the detection substrate 20, which includes the center of the detection substrate 20.

(Gap Formation Step)

Figure 38:
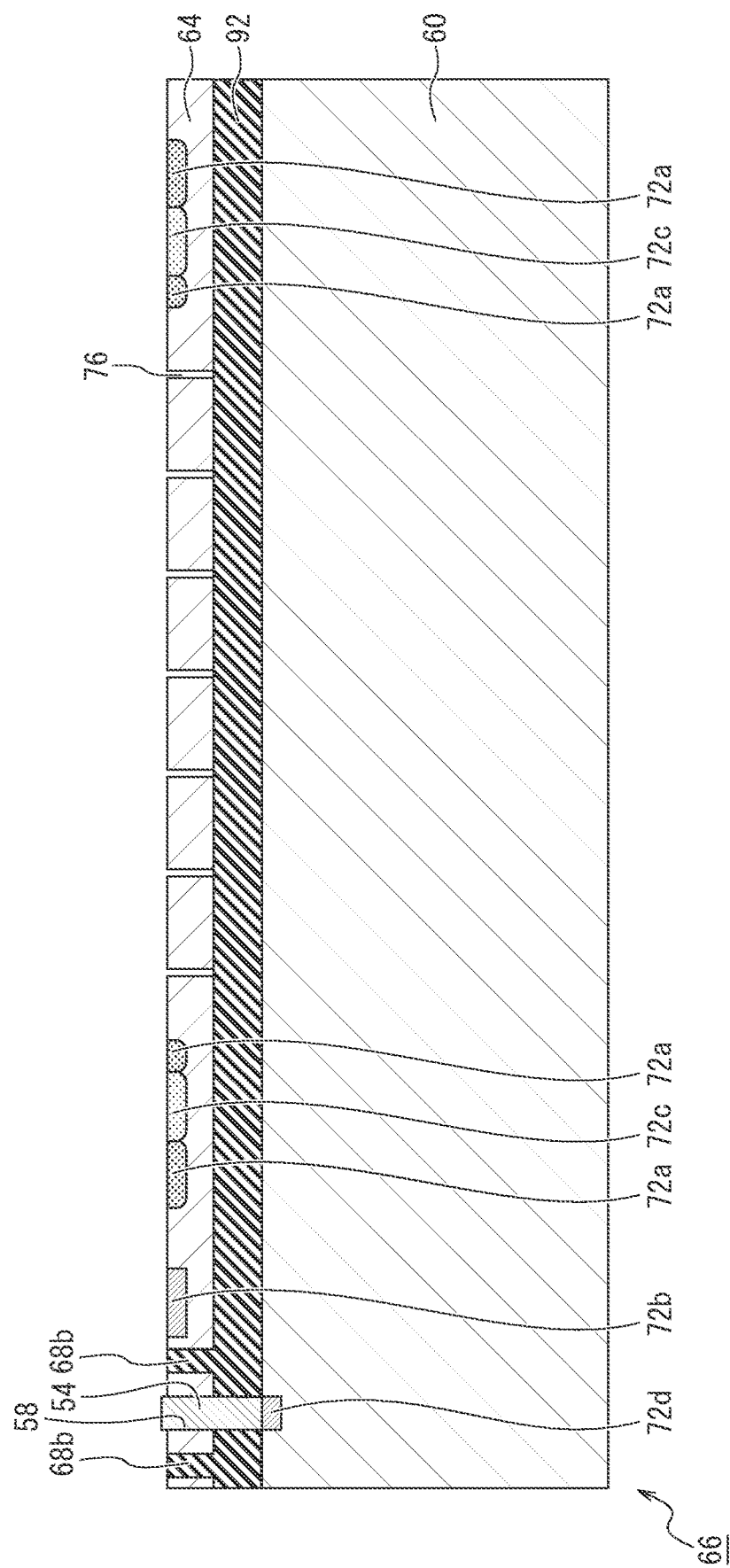
FIG. 38 is a diagram illustrating a gap formation step.
Figure 39:
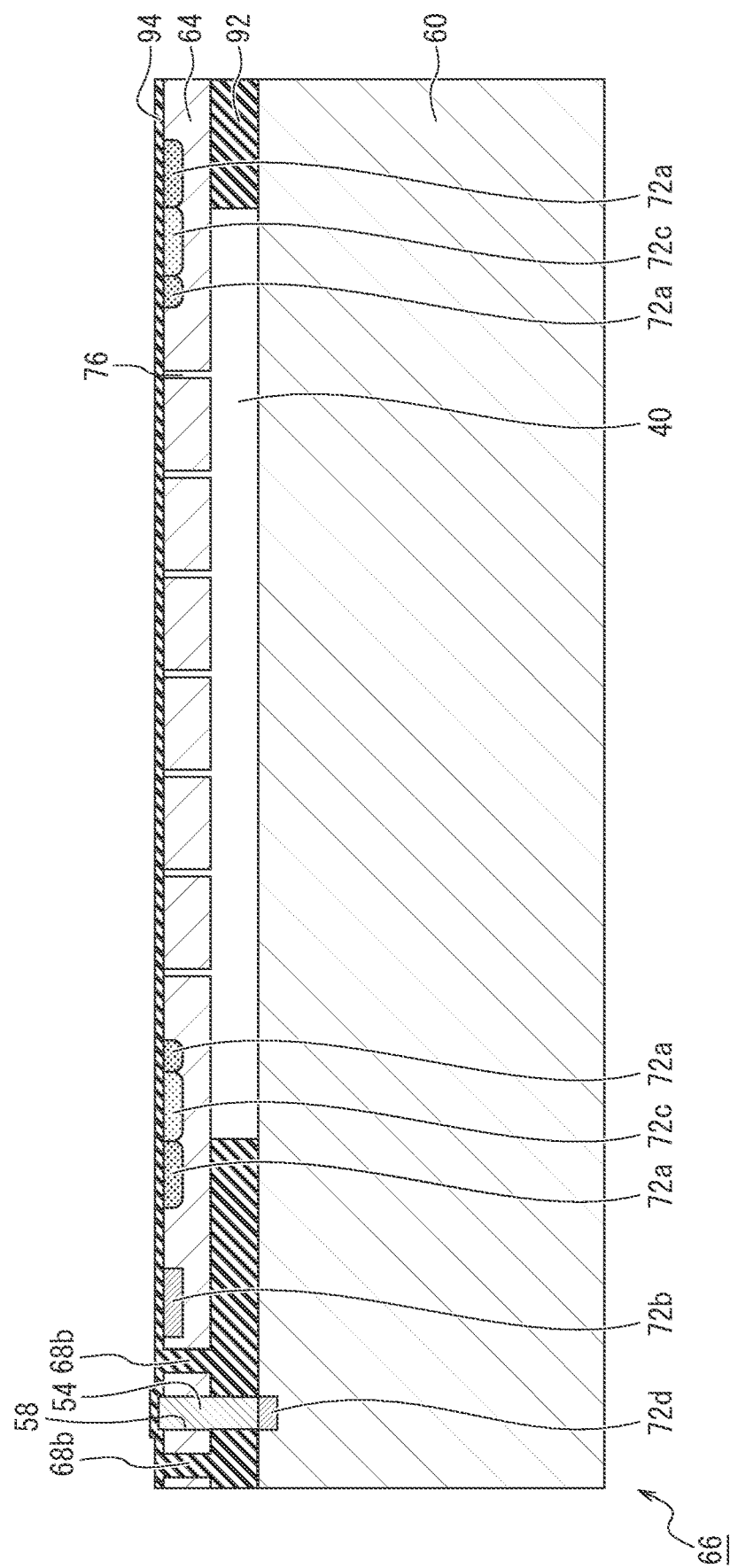
FIG. 39 is a diagram illustrating a hole sealing step.

In the gap formation step, first, the fourth silicon oxide film 68d formed on the upper side of the second silicon substrate 64 is removed, as illustrated in FIG. 38. After the fourth silicon oxide film 68d is removed, only the sacrificial layer 92 is selectively etched by causing HF vapor to permeate into the first silicon substrate 60 side through the holes 76, to thereby form a gap 40 between the first silicon substrate 60 and the second silicon substrate 64, as illustrated in FIG. 39. The reason why HF wet etching is not used here is to avoid the occurrence of defect (also called stiction) where the gap 40 is collapsed by the surface tension of pure water or the like during drying after the gap 40 is formed.

In the gap formation step, the insulating portion 6 is formed between the first silicon substrate 60 and the second silicon substrate 64 at a position where the sacrificial layer 92 remains, by forming the gap 40 between the first silicon substrate 60 and the second silicon substrate 64. The insulating portion 6 electrically insulates the first silicon substrate 60 from the second silicon substrate 64. As described above, in the gap formation step, the sacrificial layer 92 located between a preset area including the center of the detection substrate 20 and the support substrate 10 is removed by performing etching through the holes 76, to thereby form the gap 40 between the support substrate 10 and the detection substrate 20. In addition, the gap formation step forms the insulating portion 6 that is provided at the position where the sacrificial layer 92 remains between the detection substrate 20 and the support substrate 10, and electrically insulates the detection substrate 20 from the support substrate 10.

(Hole Sealing Step)

In the hole sealing step, the holes 76 are sealed by an oxide film 94 as illustrated in FIG. 39. As a method of sealing the holes 76, for example, it is effective to combine thermal oxidation treatment with CVD or the like, however, when the diameter of the holes 76 is small, it is possible to use only CVD. As described above, in the hole sealing step, the holes 76 are sealed by forming the oxide film 94 on one side of the detection substrate 20, which is opposite to the other side facing the support substrate 10.

(Wiring Layer Formation Step)

Figure 40:
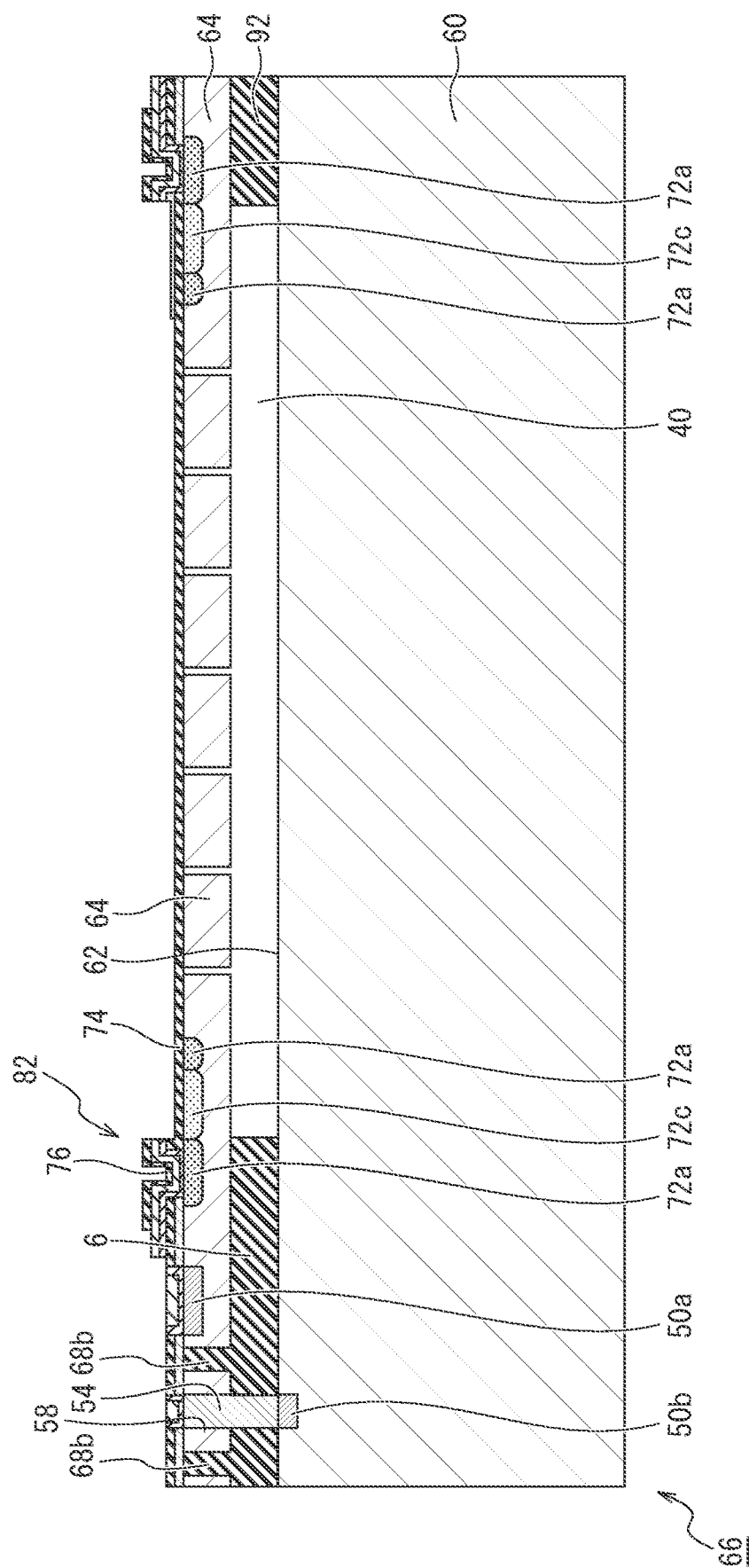
FIG. 40 is a diagram illustrating a wiring layer formation step.

The wiring layer formation step follows the same procedure as in the first embodiment described above, so its description is omitted. As described above, the wiring layer formation step forms the wiring layer 82 that includes the first terminal 50a electrically connected to the membrane 22 and the second terminal 50b electrically connected to the support substrate 10, as illustrated in FIG. 40.

(Removal Step)

The removal step follows the same procedure as in the first embodiment described above, so its description is omitted.

(Receptor Formation Step)

The receptor formation step follows the same procedure as in the first embodiment described above, so its description is omitted.

(Operation and Action)

The operation and action of the second embodiment are the similar to those of the first embodiment described above, so their descriptions are omitted. The second embodiment described above is one example of the present invention, and the present invention is not limited to the second embodiment described above, and various changes can be made in accordance with design, etc., even in other forms than this embodiment, as long as they do not deviate from the technical ideas of the present invention.

(Advantageous Effects of Second Embodiment)

The gas sensor manufacturing method of the second embodiment can achieve the advantageous effects described below.

(1) The gas sensor manufacturing method includes the laminate formation step, the through-electrode formation step, the first ion implantation step, the second ion implantation step, the third ion implantation step, the low-resistance area formation step, the hole formation step, the gap formation step, the hole sealing step, the removal step, and the wiring layer formation step. The laminate formation step is a step for laminating the insulating sacrificial layer 92 to the support substrate 10 and further laminating the detection substrate 20 to the sacrificial layer 92 to thereby form the laminate 66. The through-electrode formation step is a step for removing a part of the detection substrate 20 to form the through-hole 58 that penetrates into the support substrate 10 from the surface on one side of the detection substrate 20, which is opposite to the other side facing the support substrate 10. Furthermore, the through-electrode formation step is a step for forming the through-electrode 54 that reaches from the surface to the support substrate 10 by burying the through-hole 58 with an electrode material containing impurities. The first ion implantation step is a step for implanting the first ions into a selected partial area of the surface of the detection substrate 20, which is outside a preset area that includes the center of the detection substrate 20. The second ion implantation step is a step for implanting the second ions into a selected area of the detection substrate 20, which is outside the area where the first ions have been implanted. The third ion implantation step is a step for implanting the third ions into a preset area of the surface of the detection substrate 20. The low-resistance area formation step is a step for forming the first low-resistance areas 72a in the area where the first ions have been implanted, the second low-resistance area 72b in the area where the second ions have been implanted, and the third low-resistance areas 72c in the area where the third ions have been implanted, by heat-treating the laminate 66. Furthermore, the low-resistance area formation step is a step of forming the fourth low-resistance area 72d in a preset area of the surface on one side of the support substrate 10, which faces the detection substrate 20, by solid-phase diffusing impurities from the through-electrode 54 into the support substrate 10. The hole formation step is a step for forming the holes 76 that penetrate into the sacrificial layer 92 in a preset area of the detection substrate 20 including the center of the detection substrate 20. The gap formation step is a step for providing the gap 40 between the support substrate 10 and the detection substrate 20, by removing the sacrificial layer 92 located between the support substrate 10 and a preset area including the center of the detection substrate 20 by performing etching through the holes. Furthermore, the gap formation step is a step for forming the insulating portion 6 that is provided at the position where the sacrificial layer 92 remains between the detection substrate 20 and the support substrate 10, and electrically insulates the detection substrate 20 from the support substrate 10. The hole sealing step is a step for sealing the holes 76 by forming an oxide film on one side of the detection substrate 20, which is opposite to the other side facing the support substrate 10. The removal step is a step for forming the membrane 22, the fixing member 24, and at least one pair of the coupling portions 26, by removing an area around a preset area including the center of the detection substrate 20 and excluding the first low-resistance areas 72a. The wiring layer formation step is a step for forming the wiring layer 82 that includes the first terminal 50a electrically connected to the membrane 22 and the second terminal 50b electrically connected to the support substrate 10.

Therefore, it is possible to detect a fault, without causing the receptor 30 to adsorb a gas or any other fluid, by applying electric potentials to the first and second terminals 50a and 50b, without requiring adhesion of a fluid containing a measurement target to the receptor 30 or application of a mechanical stress. Therefore, it is possible to provide a manufacturing method for the gas sensor 1 that can detect a fault without requiring adhesion of a fluid containing a measurement target to the receptor or application of a mechanical stress.

Third Embodiment

Figure 41:
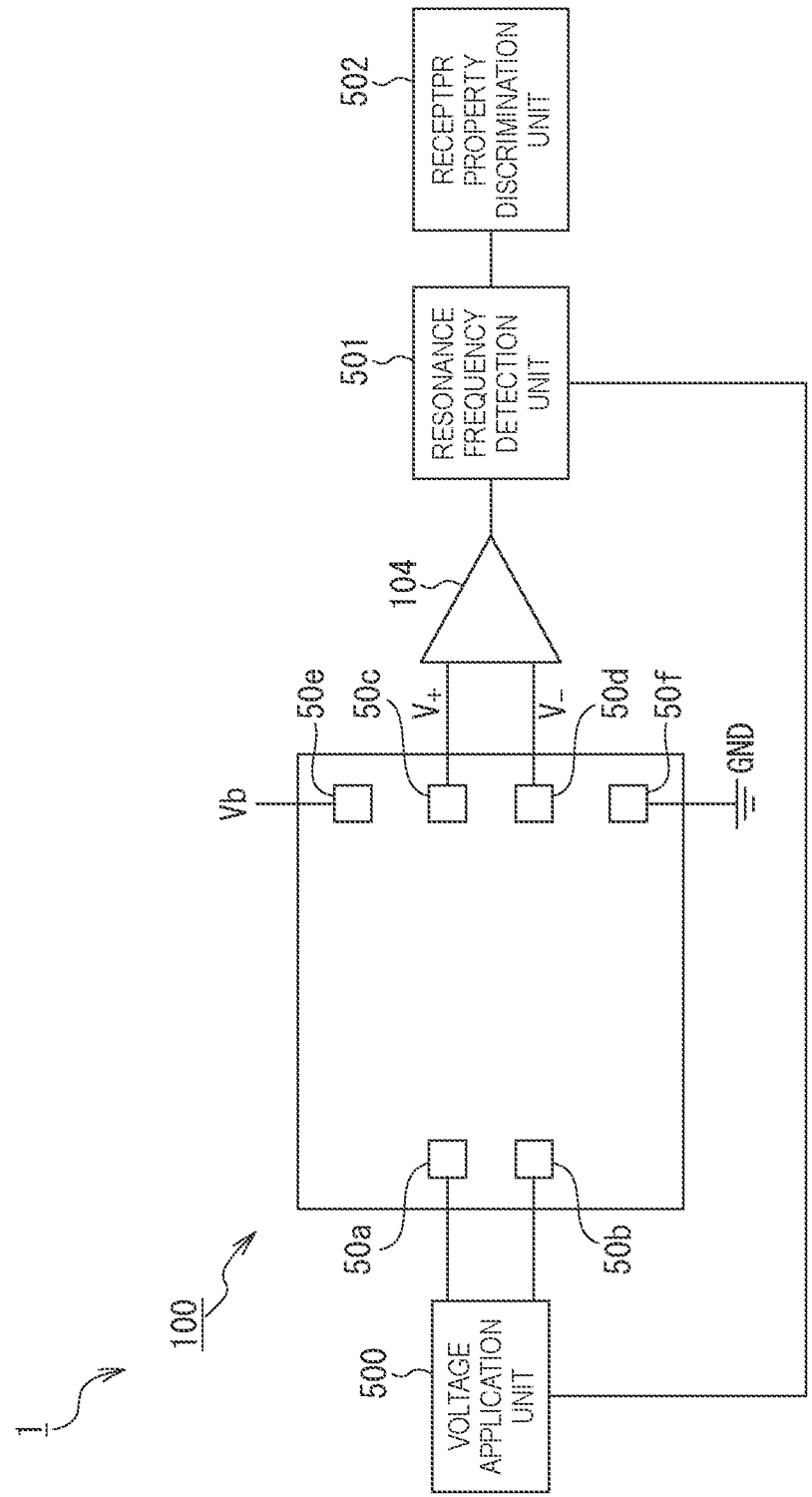
FIG. 41 is a diagram illustrating a configuration of a fault detector according to a third embodiment of the invention.
Figure 42A:
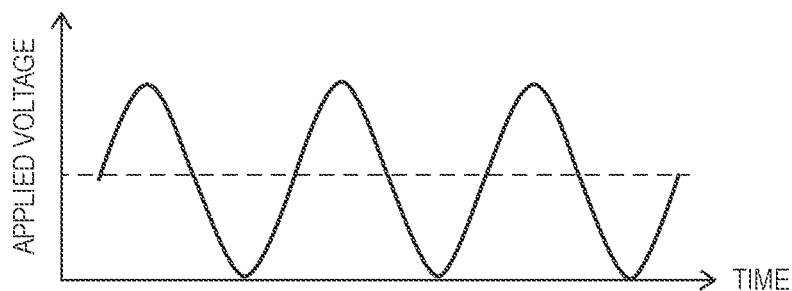
FIGS. 42A to 42C are diagrams illustrating an example of a periodic electrical signal that generates a periodic electrostatic attraction.
Figure 42B:
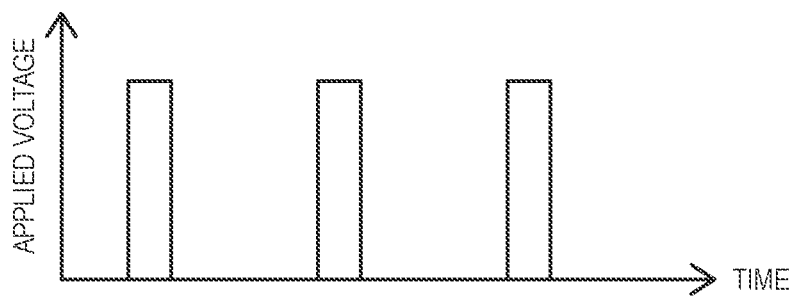
Figure 42C:
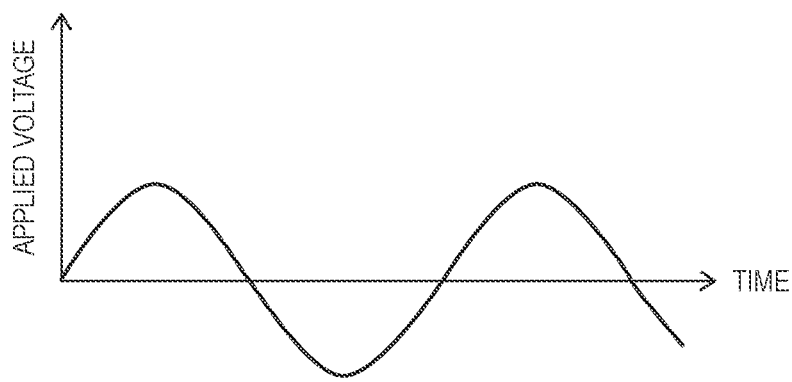

A third embodiment of the invention is described below with reference to the drawings.
(Configuration)
A configuration of the third embodiment is explained using FIGS. 41 to 43, while referring to FIGS. 1 to 40. The gas sensor 1 of the third embodiment has the similar configuration as the first embodiment, except for a configuration of the fault detector 100. In the following description, the similar configurations as in the first and second embodiments described above may be omitted from illustrations and descriptions. The fault detector 100 includes a voltage application unit 500, a resistance detection unit 104, a resonance frequency detection unit 501, and a receptor property discrimination unit 502, as illustrated in FIG. 41.

The voltage application unit 500 is formed from the first power supply 102 and the multiplexer 101, and can apply a voltage between the first terminal 50a and the second terminal 50b. The voltage application unit 500 applies a voltage between the first and second terminals 50a and 50b, thereby inputting a periodic electrical signal to the first and second terminals 50a and 50b and generating a periodic electrostatic attraction to resonate the membrane 22, the coupling portion 26 and the receptor 30. For example, the signals illustrated in FIG. 42A to 42C may be used as the periodic electrical signal that generates periodic electrostatic attraction.

The resistance detection unit 104 is connected to the third and fourth terminals 50c and 50d, and detects the resistance value of the flexible resistor 28. The resistance detection unit 104 also outputs the detected resistance value to the resonance frequency detection unit 501.

The resonance frequency detection unit 501 detects the resonance frequency of the membrane 22, the coupling portion 26 and the receptor 30 from the resistance value of the flexible resistor 28 detected by the resistance detection unit 104. Incidentally, the resonance frequency changes before and after the receptor 30 is formed. The resonance frequency detection unit 501 outputs the detected resonance frequency to the receptor property discrimination unit 502. Furthermore, the resonance frequency detection unit 501 outputs the detected resonance frequency as a reference signal to the voltage application unit 500.

The receptor property discrimination unit 502 discriminates the physical property of the receptor 30 based on the reference value of the resonance frequency stored in advance and the resonance frequency detected by the resonance frequency detection unit 501. Subsequently, the receptor property discrimination unit 502 determines whether the physical property of the receptor 30 is acceptable or not to the standard. In addition to this, when the physical property of the receptor 30 is acceptable to the standard, the receptor property discrimination unit 502 assigns a rank to the physical property of the receptor 30 (e.g., three ranks of "excellent", "good," and "passed"). The physical property of the receptor 30 to be discriminated by the receptor property discrimination unit 502 includes the mass of the receptor 30 and the hardness of the receptor 30.

When the receptor property discrimination unit 502 discriminates the physical property of the receptor 30, the receptor property discrimination unit 502 inspects the state of formation (mass and thickness) of the receptor 30, by discriminating whether or not the variation between the resonance frequency detected by the resonance frequency detection unit 501 before the receptor 30 is formed and the resonance frequency detected by the resonance frequency detection unit 501 after the receptor 30 is formed, is a variation conforming to the reference value of the resonance frequency. Specifically, in the conditional equation of the spring-mass system, a mass variation is related to the mass of the formed receptor 30, and a spring constant variation is related to the thickness (hardness) of the formed receptor 30.

When the dependence on the thickness of the receptor 30 is examined theoretically while defining the thickness of the receptor 30 as "tr," the Young's modulus of the receptor 30 as "Er," the thickness of the membrane 22 as "ta," the Young's modulus of the membrane 22 as "Ea," the diffusion expansion coefficient of the membrane 22 as "β," a concentration variation as "Δc," and the diameter of the receptor 30 as "φ", the following theoretical equation (1) is established.

$$D = \frac{3\beta\Delta c\phi^2}{4\left\{3 + \frac{(1+mn)(1+n^3m)}{(1+n)^2}\right\}(1+1/n)t_a} \quad (1)$$

Note that the following theoretical equation (2) holds in the theoretical equation (1).

$$n = \frac{t_a}{t_r}, m = \frac{E_a}{E_r} \quad (2)$$

Figure 43:
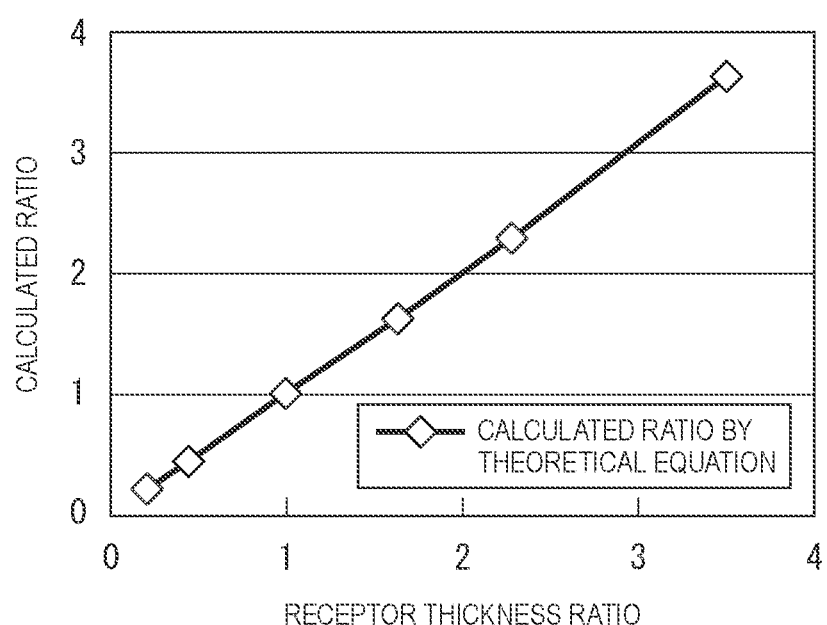
FIG. 43 is a diagram illustrating a relationship between a receptor thickness ratio and a ratio calculated by a theoretical equation.

Furthermore, when the dependence on the thickness of the receptor 30 is examined by finite element analysis, the relationship illustrated in FIG. 43 is established between the thickness ratio of the receptor 30 and the ratio calculated from theoretical equations (1) and (2). The relationship illustrated in FIG. 43 is an example for the case where, the thickness of the receptor 30 is 1 [μm], and the thickness of the membrane 22 is 3 [μm] in reference value (average value). Therefore, both in theory and in finite element analysis, the correlation of the mass and thickness of the receptor 30 with the gas sensitivity of the receptor 30 has been confirmed.

(Gas Sensor Inspection Method)

A method of inspecting the gas sensor 1 in the third embodiment is explained referring to FIGS. 1 to 43. Inspection of the gas sensor 1 in the third embodiment is performed, for example, during factory inspection of the gas sensor 1 (at the time of manufacture, shipment, etc.).

The inspection method of the gas sensor 1 in the third embodiment is for inspecting the physical property of the receptor 30 for the gas sensor 1, and includes a second voltage application step, an inspection-time resistance detection step, a resonance frequency calculation step, and a receptor property discrimination step. The second voltage application step is a step for applying a preset second voltage between the first terminal 50a and the second terminal 50b. The inspection-time resistance detection step is a step for detecting an inspection-time resistance value. The inspection-time resistance value is the resistance value of the flexible resistor 28 with the second voltage being applied between the first and second terminals 50a and 50b.

The resonance frequency calculation step is a step for calculating the resonance frequency of the receptor 30 from the inspection-time resistance value detected in the inspection-time resistance detection step. The receptor property discrimination step is a step for discriminating the physical property of the receptor 30 by comparing the reference value of the resonance frequency with the resonance frequency calculated in the resonance frequency calculation step.

(Advantageous Effects of Third Embodiment)

The gas sensor 1 of the third embodiment can achieve the advantageous effects described below.

(1) The gas sensor includes the resonance frequency detection unit 501 that detects the resonance frequency of the membrane 22, the coupling portion 26 and the receptor 30 from the resistance value of the flexible resistor 28, and the receptor property discrimination unit 502 that discriminates the physical property of the receptor 30 based on the reference value of the resonance frequency and the detected resonance frequency. Accordingly, by discriminating the physical property of the receptor 30, it is possible to electrically determine poor gas sensitivity due to the receptor 30, without having to perform a gas response test. This is because the physical property of the receptor 30 is correlated with the gas sensitivity by the receptor 30, and thus variations in the physical property of the receptor 30 correspond to variations in the gas sensitivity by the receptor 30. Therefore, in the third embodiment, it is possible to discriminate the shape of the receptor 30 (including the thickness, a contact area with the membrane 22, and the volume), as the physical property of the receptor 30. Furthermore, the third embodiment makes it possible to discriminate the membrane quality (gap) and the sensitive membrane type, as the physical property of the receptor 30.

(2) By inputting periodic electrical signals to the first and second terminals 50a and 50b, the voltage application unit 500 generates periodic electrostatic attraction to resonate the membrane 22, the coupling portion 26 and the receptor 30. Therefore, the accuracy of discrimination the physical property of the receptor 30 can be improved compared to a configuration in which the voltage application unit 500 inputs non-periodic electrical signals to the first and second terminals 50a and 50b.

In addition, the inspection method for the gas sensor 1 of the third embodiment can achieve the advantageous effects described below.

(3) The inspection method includes the second voltage application step of applying the second voltage between the first terminal 50a and the second terminal 50b, and the inspection-time resistance detection step of detecting the inspection-time resistance value, which is the resistance value of the flexible resistor 28 with the second voltage being applied between the first terminal 50a and the second terminal 50b. In addition, the inspection method includes the resonance frequency calculation step for calculating the resonance frequency of the receptor 30 based on the inspection-time resistance value detected in inspection-time resistance detection step, and the receptor property discrimination step for discriminating the physical property of the receptor 30 by comparing the reference value of the resonance frequency with the resonance frequency calculated in the resonance frequency calculation step. Accordingly, it is possible to electrically determine poor gas sensitivity due to the receptor 30 by discriminating the physical property of the receptor 30, without having to perform a gas response test.

(Variation of Third Embodiment)

(1) In the third embodiment, the voltage application unit 500 is configured such that periodic electrical signals are inputted to the first and second terminals 50a and 50b, but it is not limited to this configuration. That is, the voltage application unit 500 may be configured to input non-periodic electrical signals to the first and second terminals 50a and 50b.

Fourth Embodiment

A fourth embodiment of the invention is described below with reference to the drawings.

(Configuration)

Figure 44:
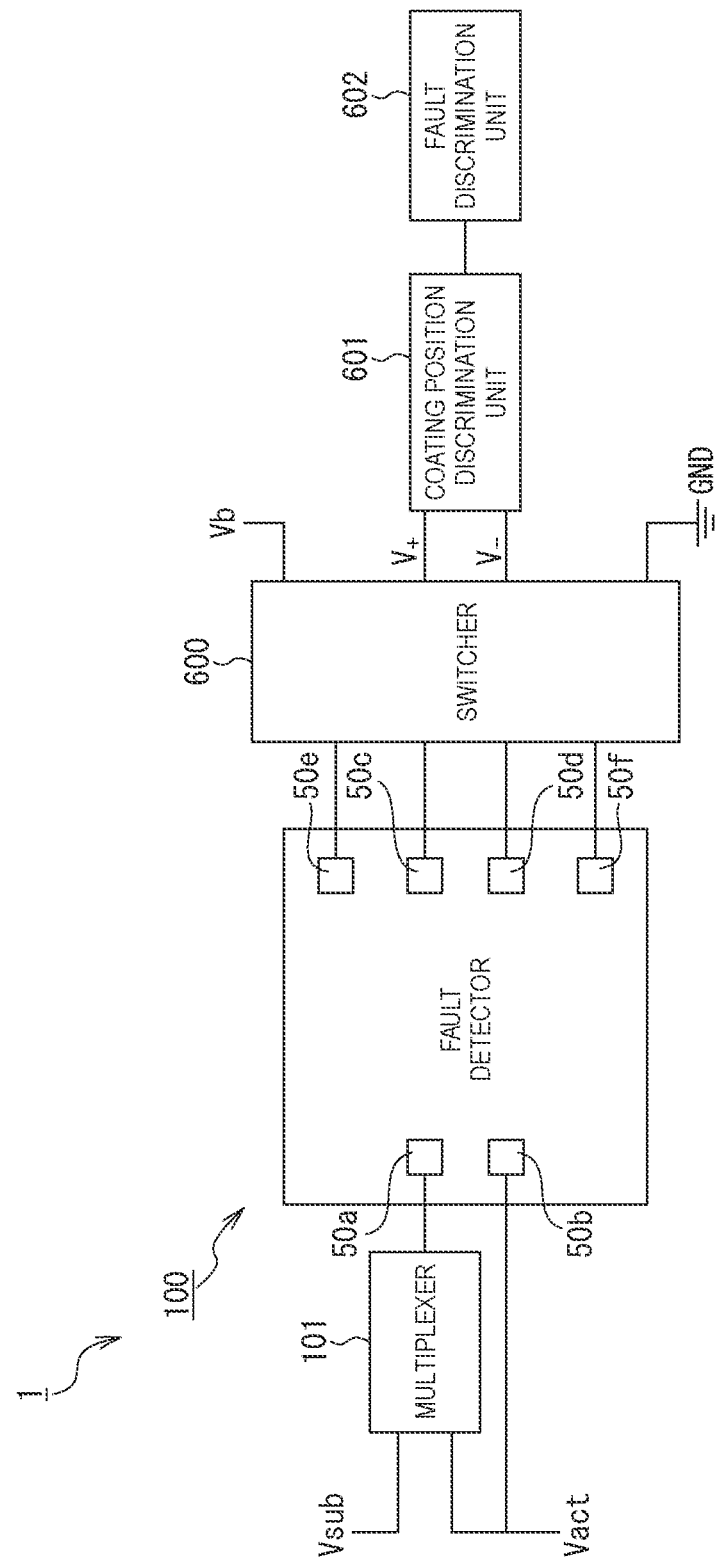
FIG. 44 is a diagram illustrating a configuration of a fault detector according to a fourth embodiment of the invention.

A configuration of the fourth embodiment is explained using FIG. 44, while referring to FIGS. 1 to 43. The gas sensor 1 of the fourth embodiment has the similar configuration as the first embodiment, except for the fault detector 100. In the following description, the similar configurations as in the first and second embodiments described above may be omitted from illustrations and descriptions.

The fault detector 100 includes a multiplexer 101, a switcher 600, a coating position discrimination unit 601, and a fault discrimination unit 602, as illustrated in FIG. 44.

The multiplexer 101 connects the first terminal 50a to a first voltage supply source Vsub or a second voltage supply source Vact, depending on a switching signal received. The first voltage supply source Vsub is formed, for example, from the GND terminal. The second voltage supply source Vact is formed, for example, from the first power supply 102. Furthermore, the second voltage supply source Vact is always connected to the second terminal 50b, as illustrated in FIG. 44. Accordingly, when the first terminal 50a is connected to the first voltage supply source Vsub by the multiplexer 101, a potential difference is generated between the support substrate 10 and the membrane 22. On the other hand, if the first terminal 50a is connected to the second voltage supply Vact by the multiplexer 101, a short circuit is made between the support substrate 10 and the membrane 22.

The switcher 600 is able to switch the connection between the terminals (fifth and sixth terminals 50e and 50f) that apply a bridge voltage to a bridge circuit and a bridge voltage application unit, and the connection between the output terminals (third and fourth terminals 50c and 50d) of the bridge circuit and the coating position discrimination unit 601, depending on the switching signal received. Here, the bridge circuit is constituted from four flexible resistors 28a to 28d. This is because the four flexible resistors 28a to 28d are formed such that coadjacent flexible resistors 28 (the coupling portion 26a and the coupling portions 26c, 26d, as well as the coupling portion 26b and the coupling portions 26c, 26d) are connected to one another. The bridge voltage application unit is constituted from the second power supply 103. The bridge voltage is a voltage applied to the four flexible resistors 28a to 28d by the second power supply 103.

The coating position discrimination unit 601 discriminates the coating position of the receptor 30 from the output value of the bridge circuit in the state where the first voltage is applied between the first and second terminals 50a and 50b, and the output value of the bridge circuit in the state where the second voltage different from the first voltage is applied between the first and second terminals 50a and 50b. The process in which the coating position discrimination unit 601 discriminates the coating position of the receptor 30 is described later. The state in which the first voltage is applied between the first terminal 50a and the second terminal 50b is, for example, a state in which the first terminal 50a and the second terminal 50b are connected to the second voltage supply source Vact to short-circuit between the support substrate 10 and the membrane 22. The state in which the second voltage is applied between the first terminal 50a and the second terminal 50b is, for example, a state in which the first terminal 50a is connected to the first voltage supply source Vsub and the second terminal 50b is connected to the second voltage supply source Vact to generate a potential difference between the support substrate 10 and the membrane 22.

The fault discrimination unit 602 determines whether the coating position of the receptor 30 discriminated by the coating position discrimination unit 601 is faulty or not. When the fault discrimination unit 602 discriminates whether the coating position of the receptor 30 is faulty or not, for example, it determines that the coating position of the receptor 30 is faulty if the deviation between the coating position of the receptor 30 discriminated by the coating position discrimination unit 601 and the reference coating position (such as the center of the membrane 22) exceeds a threshold value. In addition, when the coating position of the receptor 30 is not faulty, the fault discrimination unit 602 assigns a rank to the coating position of the receptor 30 (for example, three ranks of "excellent," "good," and "passed").
(Process in which Coating Position Discrimination Unit 601 Discriminates Coating Position of Receptor 30)

The process in which the coating position discrimination unit 601 discriminates the coating position of the receptor 30 is explained depending on the coating position of the receptor 30 relative to the reference coating position, using FIGS. 45 to 53, while referring to FIG. 44. In FIGS. 45 to 52, the configuration of the gas sensor is illustrated schematically for the sake of explanation, and in particular, unlike the explanation above, the membrane 22 and the receptor 30 are illustrated as quadrilaterals.
(When Coating Position of Receptor 30 Overlaps with Reference Coating Position)

An explanation is given for the case where the coating position of the receptor 30 overlaps with the reference coating position, i.e., the coating position of the receptor 30 is at the center of the membrane 22. First, the switcher 600 is used to connect the third terminal 50c to the bridge voltage application unit, ground the fourth terminal 50d, and connect the coating position discrimination unit 601 to the fifth and sixth terminals 50e and 50f.

Figure 45:
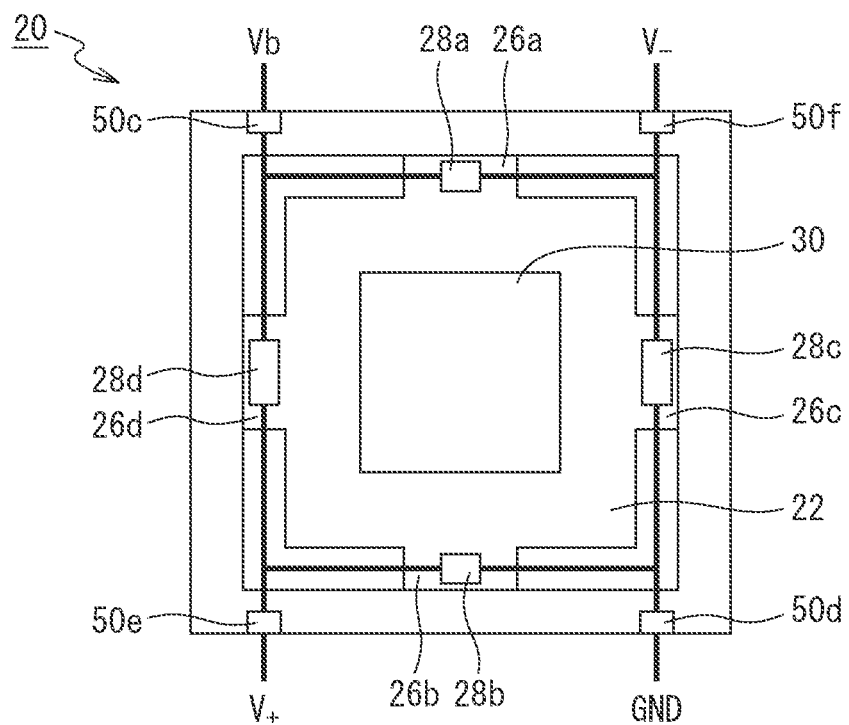
FIG. 45 is a diagram illustrating a state where the support substrate and the membrane are short-circuited when a coating position of the receptor is at the center of the membrane.
Figure 46:
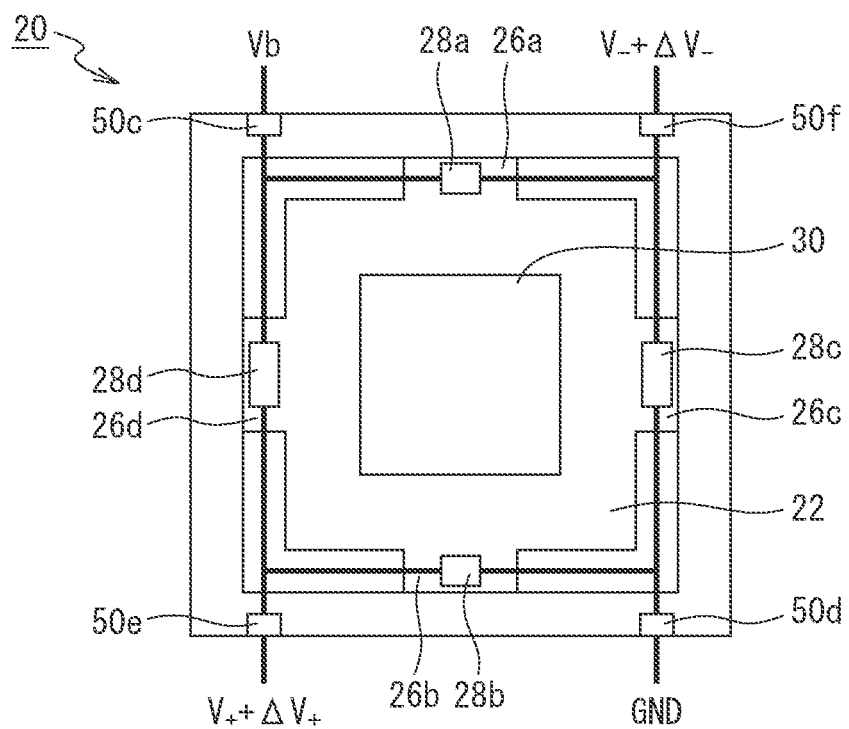
FIG. 46 is a diagram illustrating a state where a potential difference is caused between the support substrate and the membrane when the coating position of the receptor is at the center of the membrane.

As illustrated in FIG. 45, the value of the voltage outputted from the fifth terminal 50e is indicated by "V+", and the value of the voltage outputted from the sixth terminal 50f is indicated by "V−" when a short circuit is made between the support substrate 10 and the membrane 22. If the receptor 30 is formed at the center of the membrane 22, the membrane 22 bends with its center being the site of greatest change when a potential difference is generated between the support substrate 10 and the membrane 22. As illustrated in FIG. 46, the value of the voltage outputted from the fifth terminal 50e is calculated as the formula "V++ΔV+". On the other hand, the value of the voltage outputted from the sixth terminal 50f is calculated as the formula "V−+ΔV". The "ΔV+" is the differential in the voltage outputted from the fifth terminal 50e, between the case where a short circuit is made and the case where a potential difference is made between the support substrate 10 and the membrane 22. The "ΔV−" is the differential in the voltage outputted from the sixth terminal 50f, between the case where a short circuit is made and the case where a potential difference is made between the support substrate 10 and the membrane 22. If the receptor 30 is formed in the center of the membrane 22, the relationship "|ΔV+|=|ΔV−|" is established. Accordingly, if the receptor 30 is formed in the center of the membrane 22, because of the symmetry of the voltage variation, there is a match, in the potential variation (the absolute value of the potential variation), between the voltage outputted from the fifth terminal 50e and the voltage outputted from the sixth terminal 50f, when a potential difference is generated between the support substrate 10 and the membrane 22.
(When Coating Position of Receptor 30 is Off to the Right)

An explanation is given for the case where the coating position of the receptor 30 is off to the right relative to the reference coating position (closer to the flexible resistor 28c than to the center of the membrane 22), that is, where the receptor 30 is formed closer to the flexible resistor 28c than to the center of the membrane 22. First, the switcher 600 is used to connect the third terminal 50c to the bridge voltage application unit, ground the fourth terminal 50d, and connect the coating position discrimination unit 601 to the fifth and sixth terminals 50e and 50f.

Figure 47:
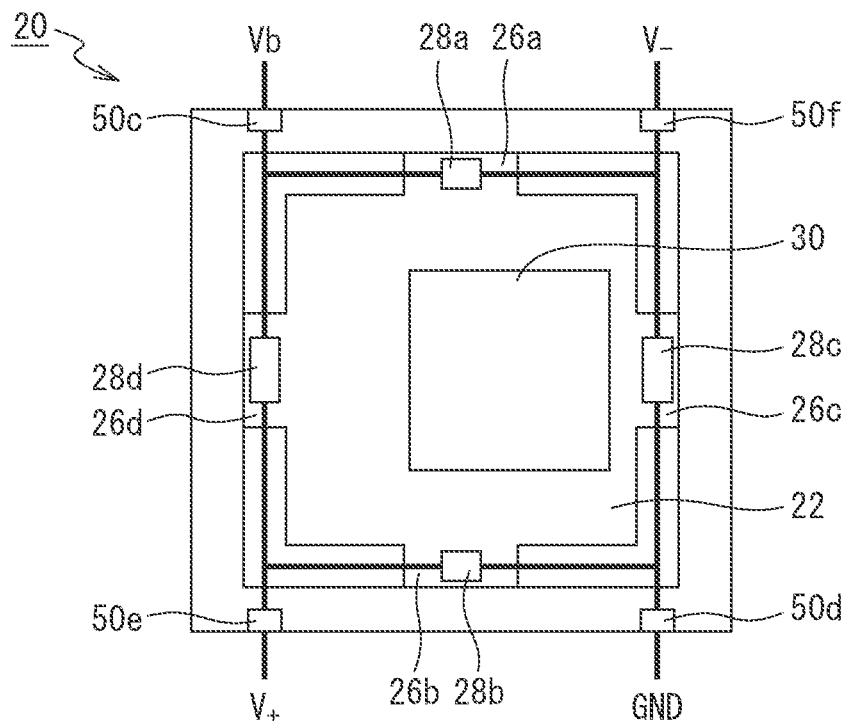
FIG. 47 is a diagram illustrating a state where the support substrate and the membrane are short-circuited when the coating position of the receptor is off to the right.
Figure 48:
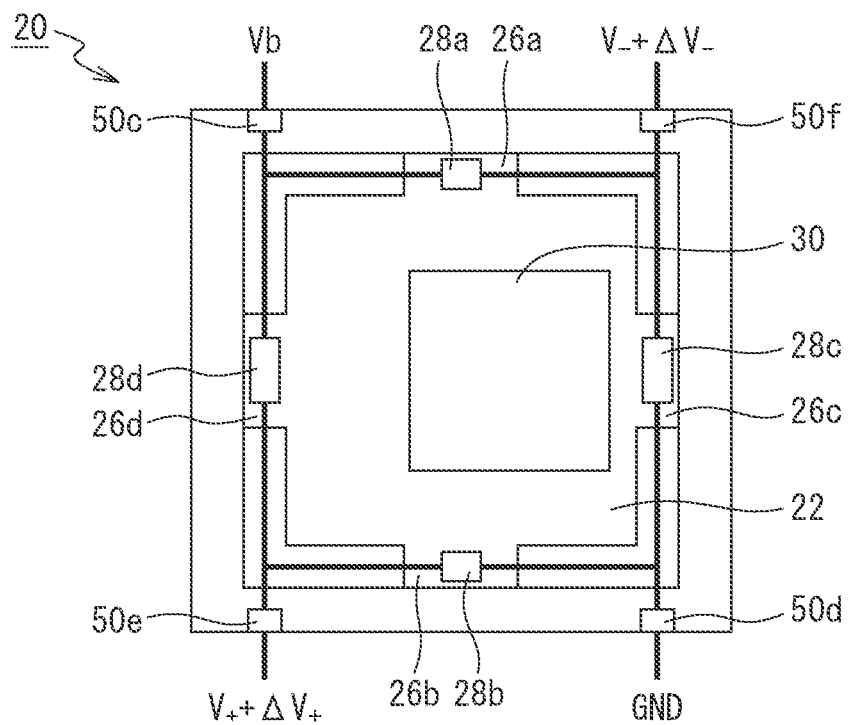
FIG. 48 is a diagram illustrating the state where a potential difference is caused between the support substrate and the membrane when the coating position of the receptor is off to the right.

As illustrated in FIG. 47, the value of the voltage outputted from the fifth terminal 50e is indicated by "V₊", and the value of the voltage outputted from the sixth terminal 50f is indicated by "V_" when a short circuit is made between the support substrate 10 and the membrane 22. If the coating position of the receptor 30 is off to the right, the membrane 22 bends with its position closer to the flexible resistor 28d than to its center being as the site of greatest change, when a potential difference is generated between the support substrate 10 and the membrane 22. Therefore, as illustrate in FIG. 48, if the coating position of the receptor 30 is off to the right, the relationship "$|\Delta V_+|>|\Delta V_-|$" is established as to the differentials of the voltages outputted from the fifth and sixth terminals 50e and 50f in the cases where a short circuit is made and where a potential difference is made between the support substrate 10 and the membrane 22.

Accordingly, if the coating position of the receptor 30 is off to the right, since the voltage variations become asymmetric, there is a mismatch between the voltage outputted from the fifth terminal 50e and the voltage outputted from the sixth terminal 50f, in the absolute value of the amount of change of the potential when a potential difference is generated between the support substrate 10 and the membrane 22. Explanation is omitted for the case where the coating position of the receptor 30 is off to the left relative to the reference coating position (closer to the flexible resistor 28d than to the center of the membrane 22), that is, where the receptor 30 is formed closer to the flexible resistor 28d than to the center of the membrane 22.

(When Coating Position of Receptor 30 is Off to the Bottom)

An explanation is given for the case where the coating position of the receptor 30 is off to the bottom relative to the reference coating position (closer to the flexible resistor 28b than to the center of the membrane 22), that is, where the receptor 30 is formed closer to the flexible resistor 28b than to the center of the membrane 22. First, the switcher 600 is used to connect the third terminal 50c to the bridge voltage application unit, ground the fourth terminal 50d, and connect the coating position discrimination unit 601 to the fifth and sixth terminals 50e and 50f.

Figure 49:
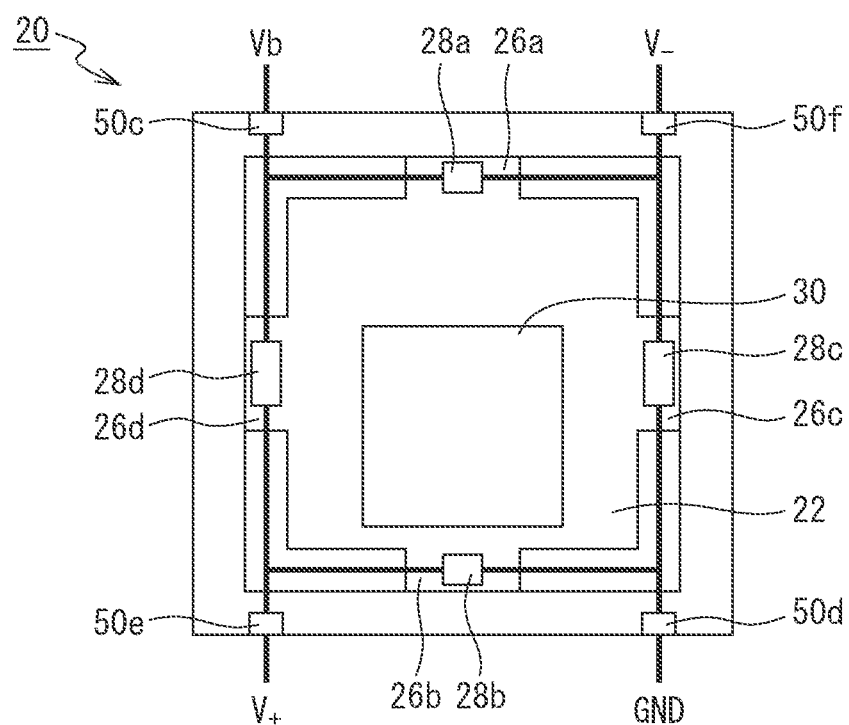
FIG. 49 is a diagram illustrating a state where the support substrate and the membrane are short-circuited when the coating position of the receptor is off to the bottom.

As illustrated in FIG. 49, the value of the voltage outputted from the fifth terminal 50e is indicated by "$V_+$", and the value of the voltage outputted from the sixth terminal 50f is indicated by "$V_-$" when a short circuit is made between the support substrate 10 and the membrane 22. If the coating position of the receptor 30 is off to the bottom, the membrane 22 bends with its position closer to the flexible resistor 28a than to its center being as the site of greatest change when a potential difference is generated between the support substrate 10 and the membrane 22. Therefore, as illustrate in FIG. 50, if the coating position of the receptor 30 is off to the bottom, the relationship "$|\Delta V_+|>|\Delta \Delta V_-|$" is established as to the differentials of the voltages outputted from the fifth and the sixth terminals 50e and 50f in the cases where a short circuit is made and where a potential difference is made between the support substrate 10 and the membrane 22.

Accordingly, if the coating position of the receptor 30 is off to the bottom, since the voltage variations become asymmetric, there is a mismatch between the voltage outputted from the fifth terminal 50e and the voltage outputted from the sixth terminal 50f, in the absolute value of the potential variation when a potential difference is generated between the support substrate 10 and the membrane 22. Explanation is omitted for the case where the coating position of the receptor 30 is off to the top relative to the reference coating position (closer to the flexible resistor 28a than to the center of the membrane 22), that is, where the receptor 30 is formed closer to the flexible resistor 28a than to the center of the membrane 22.

(Process for Discriminating Direction in which Coating Position of Receptor 30 is Deviated)

As described above, the voltage variations become asymmetric in both the case where the coating position of the receptor 30 is off to the right and the case where the coating position of the receptor 30 is off to the bottom. For this reason, it is impossible to discriminate in which direction the coating position of the receptor 30 is deviated, from the reference coating position, only by referring to the absolute values of the potential variations of the voltages outputted from the fifth terminal 50e and the sixth terminal 50f. Accordingly, the fourth embodiment performs a process for discriminating in which direction the coating position of the receptor 30 is deviated from the reference coating position, by switching, using the switcher 600, the connection between the terminal that applies the bridge voltage to the bridge circuit and the bridge voltage application unit, and the connection between the output terminal of the bridge circuit and the coating position discrimination unit 601.

Figure 51:
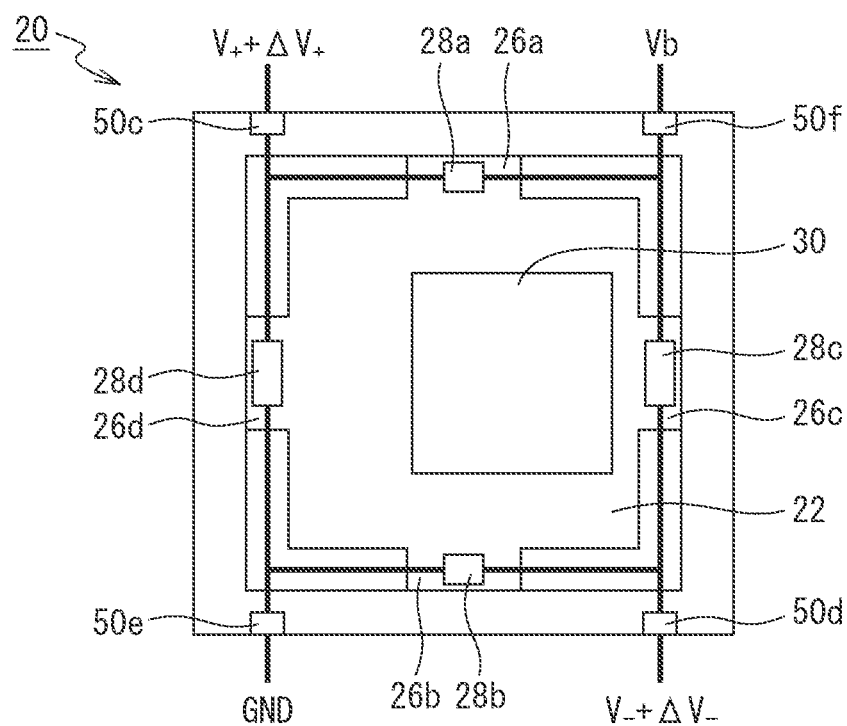
FIG. 51 is a diagram illustrating a state where a potential difference is generated between the support substrate and the membrane by switching a connection state when the coating position of the receptor is off to the right.

In the process for discriminating in which direction the coating position of the receptor 30 is deviated from the reference coating position, a potential difference is generated between the support substrate 10 and the membrane 22 before and after the connection state is switched by the switcher 600, respectively. When the coating position of the receptor 30 is off to the right, as illustrated in FIG. 51, from the state illustrated in FIG. 48, the switcher 600 connects the coating position discrimination unit 601 to the third and fourth terminals 50c and 50d, grounds the fifth terminal 50e, and connects the sixth terminal 50f to the bridge voltage application unit. In the state illustrated in FIG. 51, the voltage outputted from the third terminal 50c is "$V_+$" and the voltage outputted from the fourth terminal 50d is "$V_-$" when the support substrate 10 and the membrane 22 are short-circuited. Next, when a potential difference is generated between the support substrate 10 and the membrane 22, the voltage outputted from the third terminal 50c becomes "$V_++\Delta V_+$", and the voltage outputted from the fourth terminal 50d becomes "$V_-+\Delta V_-$". At this time, the relationship "$|\Delta V_+|>|\Delta V_-|$" is established as to the differentials of the voltages outputted from the fifth and sixth terminals 50e and 50f in the cases where a short circuit is generated and where a potential difference is generated, between the support substrate 10 and the membrane 22.

Figure 50:
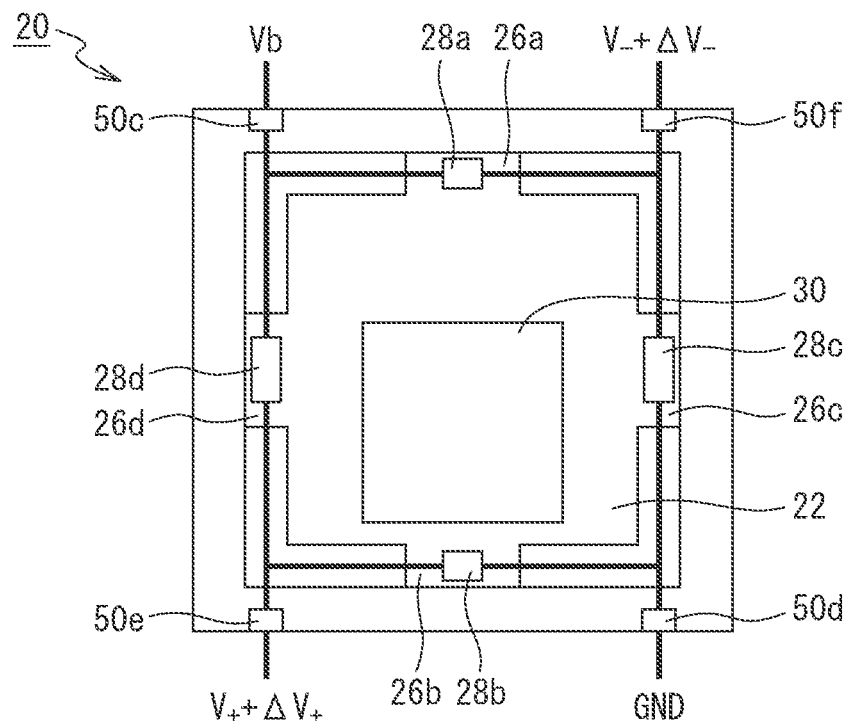
FIG. 50 is a diagram illustrating the state where a potential difference is generated between the support substrate and the membrane when the coating position of the receptor is off to the bottom.
Figure 52:
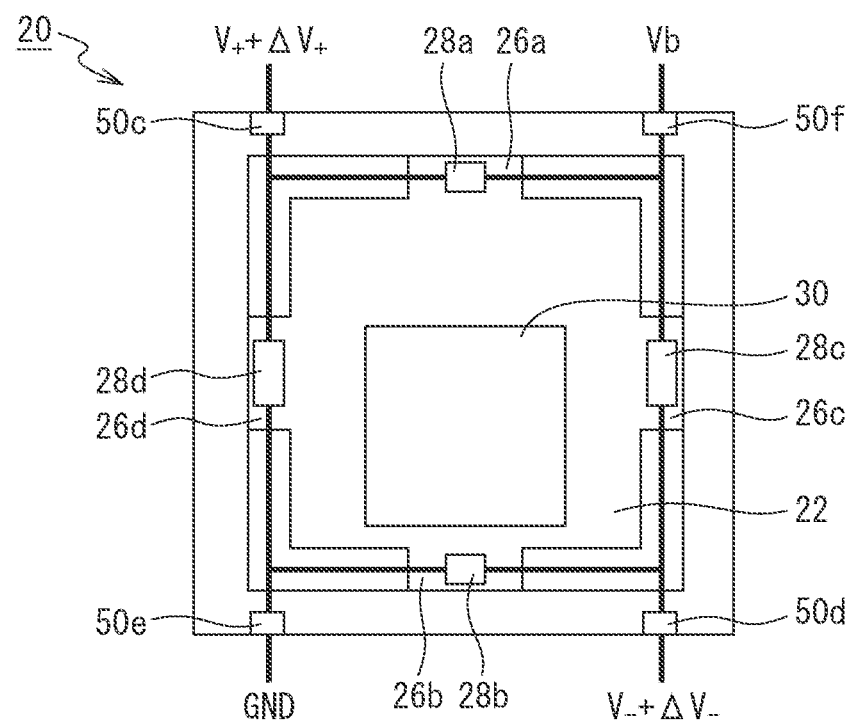
FIG. 52 is a diagram illustrating a state where a potential difference is generated between the support substrate and the membrane by switching the connection state when the coating position of the receptor is off to the bottom.

When the coating position of the receptor 30 is off to the bottom, as illustrated in FIG. 52, from the state illustrated in FIG. 50, the switcher 600 connects the coating position discrimination unit 601 to the third and fourth terminals 50c and 50d, grounds the fifth terminal 50e, and connects the sixth terminal 50f to the bridge voltage application unit. In the state illustrated in FIG. 52, the voltage outputted from the third terminal 50c is "$V_+$" and the voltage outputted from the fourth terminal 50d is "$V_-$" when the support substrate 10 and the membrane 22 are short-circuited. Next, when a potential difference is generated between the support substrate 10 and the membrane 22, the voltage outputted from the third terminal 50c becomes "$V_++\Delta V_+$", and the voltage outputted from the fourth terminal 50d becomes "$V_-+\Delta V_-$". At this time, the relationship "$|\Delta V_+|<|\Delta V_-|$" is established as to the differentials of the voltages outputted from the fifth and sixth terminals 50e and 50f in the cases where a short circuit is generated and where a potential difference is generated, between the support substrate 10 and the membrane 22.

Accordingly, the relationship illustrated in FIG. 53 is established among the coating position of the receptor 30, the resistance value variations of the four flexible resistors 28a to 28d, and the variations of the voltages outputted from the third and fourth terminals 50c and 50d, and also the fifth and sixth terminals 50e and 50f. In FIG. 53, the coating position of the receptor 30 is indicated by "COATING POSITION," the resistance value variation of the flexible resistor 28a as "FLEXIBLE RESISTOR 28a", and the resistance value variation of the flexible resistor 28b as "FLEXIBLE RESISTOR 28b". Also, in FIG. 53, the resistance value variation of the flexible resistor 28c as "FLEXIBLE RESISTOR 28c", and the resistance value variation of the flexible resistor 28d as "FLEXIBLE RESISTOR 28d". Furthermore, in FIG. 53, the variations of the voltages outputted from the third and fourth terminals 50c and 50d, and also the fifth and sixth terminals 50e and 50f are indicted by "VOLTAGE VARIATION". The resistance value variation of the four flexible resistors 28a to 28d are resistance value variations that occur in the flexible resistors 28a to 28d when a potential difference is generated between the support substrate 10 and the membrane 22 from the short-circuited state between the support substrate 10 and the membrane 22. Furthermore, in FIG. 53, "ΔR⁻" indicates a small resistance value variation compared to a resistance value variation in the case where the receptor 30 is formed in the center of the membrane 22, which is indicated by "ΔR". Also, "ΔR⁺" indicates a large resistance value variation compared to the resistance value variation in the case where the receptor 30 is formed in the center of the membrane 22, which is indicated by "ΔR". Likewise, "+ΔR" indicates an increase of the resistance value when a potential difference is generated between the support substrate 10 and the membrane 22 from the short-circuited state. The "−ΔR" indicates a reduction of the resistance value when a potential difference is generated between the support substrate 10 and the membrane 22 from the short-circuited state.

As illustrated in FIG. 53, when the receptor 30 is formed in the center of the membrane 22 (in the middle), the resistance value variations of the flexible resistors 28a and 28b are the reduction ("−ΔR" illustrated in FIG. 53), and the resistance value variations of the flexible resistors 28c and 28d are the increase ("+ΔR" illustrated in FIG. 53). Furthermore, the variations of the voltages outputted from the third and fourth terminals 50c and 50d are equal to the variations of the voltages outputted from the fifth and sixth terminals 50e and 50f. When the coating position of the receptor 30 is off to the right relative to the reference coating position, the resistance value variations of the flexible resistors 28a and 28b are the reduction, and the resistance value variation of the flexible resistor 28c is a small increase ("+ΔR⁻" illustrated in FIG. 53). The resistance value variation of the flexible resistor 28d is a large increase ("+ΔR⁺" illustrated in FIG. 53), and the variations of the voltages outputted from the third and fourth terminals 50c and 50d are different from the variations of the voltages outputted from the fifth and sixth terminals 50e and 50f.

When the coating position of the receptor 30 is off to the left relative to the reference coating position, the resistance value variations of the flexible resistors 28a and 28b are the reduction, and the resistance value variation of the flexible resistor 28c is the large increase. The resistance value variation of the flexible resistor 28d is the small increase, and the variations of the voltages outputted from the third and fourth terminals 50c and 50d are different from the variations of the voltages outputted from the fifth and sixth terminals 50e and 50f. When the coating position of the receptor 30 is off to the bottom relative to the reference coating position, the resistance value variation of the flexible resistor 28a is the small reduction ("−ΔR⁻" illustrated in FIG. 53), and the resistance value variation of the flexible resistor 28b is the large reduction ("−ΔR⁺" illustrated in FIG. 53). The resistance value variations of the flexible resistor 28c and the flexible resistor 28d are the increase, and the variations of the voltages outputted from the third and fourth terminals 50c and 50d are different from the variations of the voltages outputted from the fifth and sixth terminals 50e and 50f.

When the coating position of the receptor 30 is off to the top relative to the reference coating position, the resistance value variation of the flexible resistor 28a is the large reduction, and the resistance value variation of the flexible resistor 28b is the small reduction. The resistance value variations of the flexible resistors 28c and 28d are the increase, and the variations of the voltages outputted from the third and fourth terminals 50c and 50d are different from the variations of the voltages outputted from the fifth and sixth terminals 50e and 50f. As described above, it is possible to distinguish the resistance value variations of the four flexible resistors 28a to 28d by generating a potential difference between the support substrate 10 and the membrane 22 before and after the connection state is switched by the switcher 600, respectively. Accordingly, it possible to distinguish between the large and small variations in resistance value of the four flexible resistors 28a to 28d, unlike the conventional configuration where the connection state is not changed, and therefore, it is possible to discriminate the direction in which the coating position of the receptor 30 is deviated.

(Gas Sensor Inspection Method)

Figure 2:
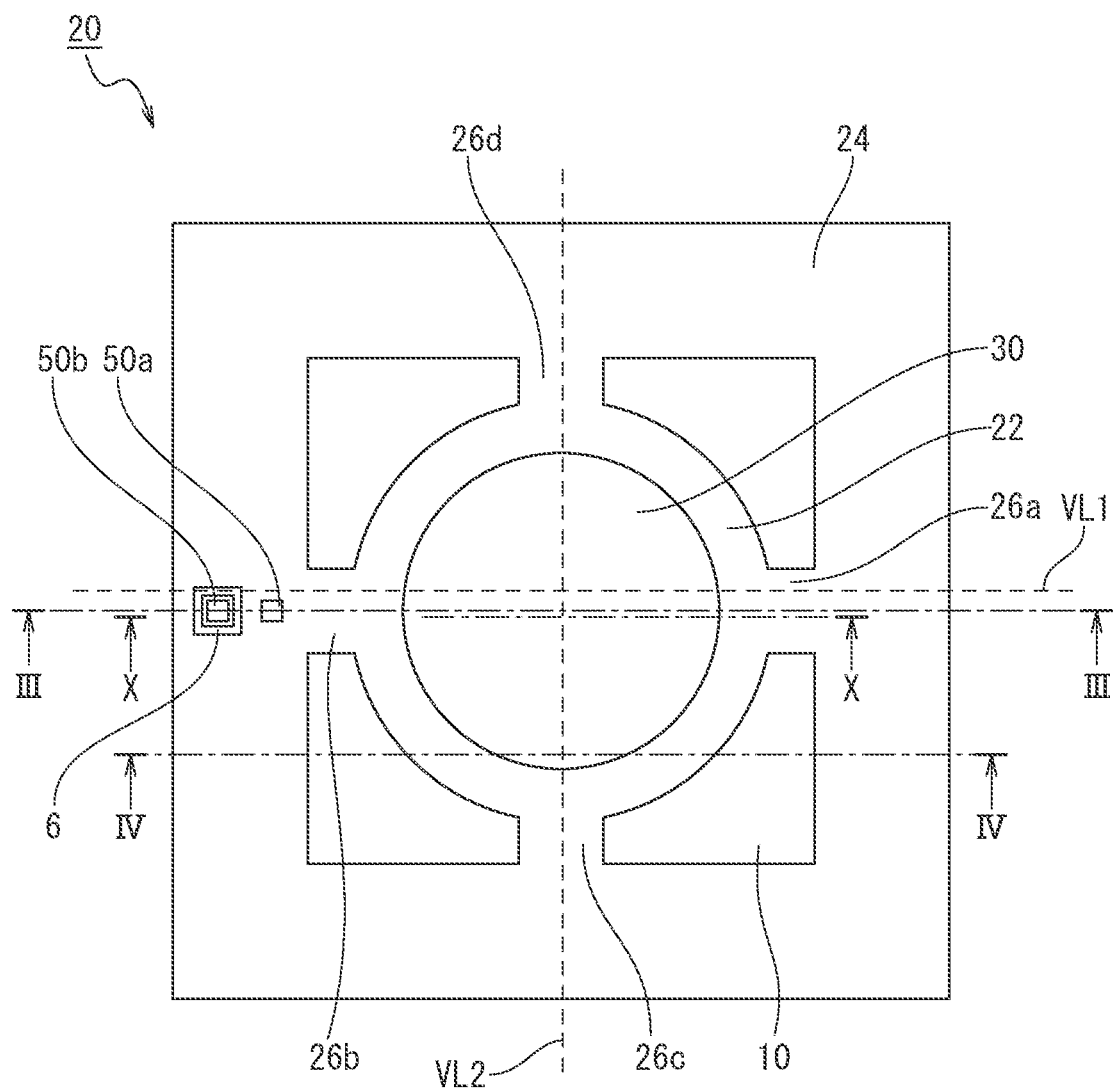
FIG. 2 is a II-line arrow view of FIG. 1.
Figure 3:
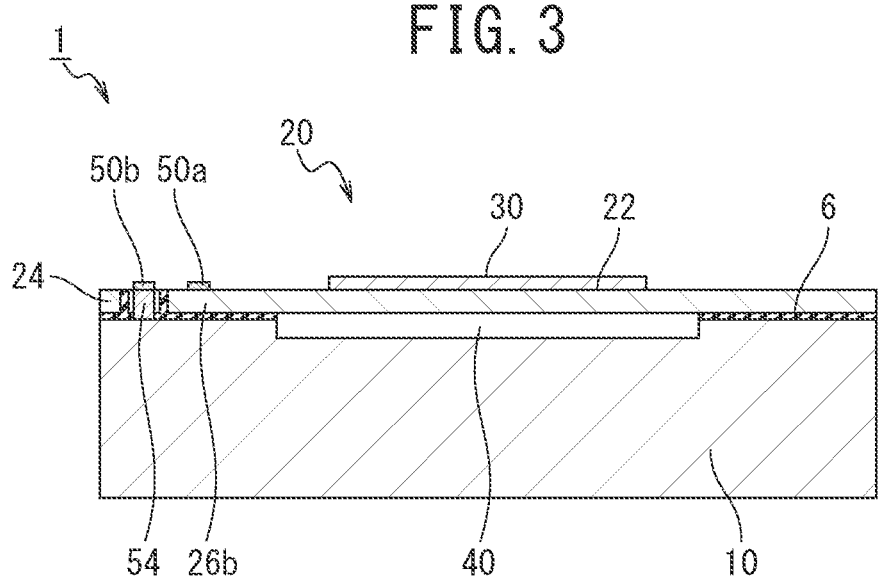
FIG. 3 is a cross-sectional view along line III-III of FIG. 2.
Figure 4:
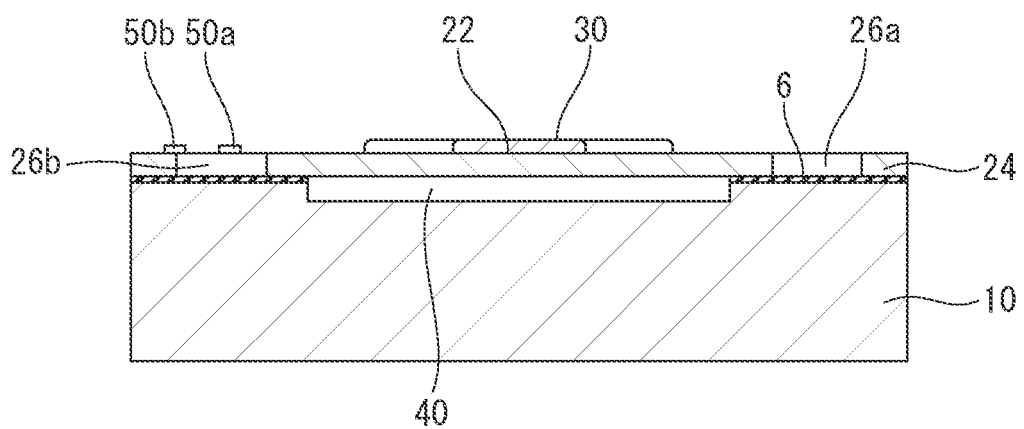
FIG. 4 is a cross-sectional view along line IV-IV of FIG. 2.

Referring to FIGS. 1 to 53, the inspection method for the gas sensor 1 according to the fourth embodiment is explained. Inspection of the gas sensor 1 according to the fourth embodiment is performed, for example, during factory inspection of the gas sensor 1 (at the time of manufacture, shipment, etc.). The inspection method for the gas sensor 1 according to the fourth embodiment is a method to inspect the coating position of the receptor 30 for the gas sensor 1, and includes a bridge voltage application step, a connection switching step, and a coating position discrimination step.

The bridge voltage application step is a step for applying a bridge voltage to the bridge circuit constituted from the flexible resistors 28. The connection switching step is a step that is performed prior to the coating position discrimination step. The connection switching step is a step for switching the connection between the terminal that applies the bridge voltage to the bridge circuit and the bridge voltage application unit, and the connection between the output terminal of the bridge circuit and the coating position discrimination unit 601.

The coating position discrimination step is a step for discriminating the coating position of the receptor 30. Specifically, in the coating position discrimination step, the coating position of the receptor 30 is discriminated from the output value of the bridge circuit with the first voltage being applied between the first terminal 50a and the second terminal 50b, and the output value of the bridge circuit with the second voltage being applied between the first terminal 50a and the second terminal 50b.

(Advantageous Effects of Fourth Embodiment)

The gas sensor 1 of the fourth embodiment can achieve the advantageous effects described below.

(1) The gas sensor includes the bridge circuit constituted from the flexible resistors 28, and the bridge voltage application unit that applies the bridge voltage to the bridge circuit. Also the gas sensor includes the coating position discrimination unit 601 that discriminates the coating position of the receptor 30 from the output value of the bridge circuit with the first voltage being applied between the first and second terminals 50a and 50b, and the output value of the bridge circuit with the second voltage different from the first voltage being applied between the first and second terminals 50a and 50b. In addition, the gas sensor includes the switcher 600 that can switch the connection between the terminal that applies the bridge voltage to the bridge circuit and the bridge voltage application unit, and the connection between the output terminal of the bridge circuit and the coating position discrimination unit 601. Therefore, it is possible to electrically determine poor gas sensitivity due to the receptor 30 by discriminating the coating position of the receptor 30, without having to perform a gas response test. This is due to the fact that the coating position of the receptor 30 correlates with the gas sensitivity by the receptor 30, and therefore the variation in the coating position of the receptor 30 corresponds to the variation of the gas sensitivity by the receptor 30. For example, when the gas sensitivity in the case where the coating position of the receptor 30 is at the center of the membrane 22 is defined as a normal gas sensitivity, if the coating position of the receptor 30 is off-center, since the flexible resistor 28 closer to the receptor 30 bends extremely, the gas sensitivity increases. Therefore, if the coating position of the receptor 30 is off-center, the gas sensitivity by the receptor 30 becomes greater than the normal gas sensitivity, depending on the amount of the deflection. According to the fourth embodiment, it is possible to discriminate the coating position (including extreme positional deflection) of the receptor 30 as the physical property of the receptor 30.

The inspection method for the gas sensor 1 of the fourth embodiment can achieve the advantageous effects described below.

(2) The inspection method includes the bridge voltage application step of applying the bridge voltage to the bridge circuit, and the coating position discrimination step of discriminating the coating position of the receptor 30 from the output value of the bridge circuit with the first voltage being applied between the first and second terminals 50a and 50b and the output value of the bridge circuit with the second voltage different from the first voltage being applied between the first and second terminals 50a and 50b. Therefore, it is possible to electrically determine poor gas sensitivity due to the receptor 30 by discriminating the coating position of the receptor 30, without having to perform a gas response test.

(3) The inspection method further includes the connection switching step of switching the connection between the terminal that applies the bridge voltage to the bridge circuit and the bridge voltage application unit, and the connection between the output terminal of the bridge circuit and the coating position discrimination unit 601, that is performed prior to the coating position discrimination step. Accordingly, it is possible to distinguish between the large and small changes in resistance value of the four flexible resistors 28a to 28d, unlike the conventional configuration where the connection state is not changed, and therefore it possible to discriminate the direction in which the coating position of the receptor 30 is deviated.

REFERENCE SIGNS LIST

1 . . . gas sensor, 2 . . . package substrate, 4 . . . connecting portion, 6 . . . insulating portion, 10 . . . support substrate, 20 . . . detection substrate, 22 . . . membrane, 24 . . . fixing member, 24a . . . through-portion, 24b . . . inside of fixing member 24, 24c . . . outside of fixing member 24, 26 . . . coupling portion, 28 . . . flexible resistor, 30 . . . receptor, 40 . . . gap, 50a . . . first terminal, 50b . . . second terminal, 50c . . . third terminal, 50d . . . fourth terminal, 50e . . . fifth terminal, 50f . . . sixth terminal, 54 . . . through-electrode, 56a . . . first trench, 56b . . . second trench, 58 . . . through-hole, 60 . . . first silicon substrate, 62 . . . recess, 64 . . . second silicon substrate, 66 . . . laminate, 68 . . . silicon oxide film, 70 . . . ion implantation area (first ion implantation areas 70a, second ion implantation area 70b, third ion implantation areas 70c), 72 . . . low-resistance area (first low-resistance areas 72a, second low-resistance area 72b, third low-resistance areas 72c, fourth low-resistance area 72d), 74 . . . silicon nitride film, 76 . . . hole, 78 . . . laminated film, 80 . . . metal film, 82 . . . wiring layer, 84 . . . membrane setting area, 88 . . . photoresist, 90 . . . connecting layer, 92 . . . sacrificial layer, 94 . . . oxide film, 96 . . . N-type polysilicon, 100 . . . fault detector, 101 . . . multiplexer, 102 . . . first power supply, 103 . . . second power supply, 104 . . . resistance detection unit, 105 . . . correction value storage unit, 106 . . . sensitivity correction unit, 107 . . . analog-to-digital conversion unit, 108 . . . interface unit, 200 . . . component detector, 201 . . . pattern storage unit, 202 . . . component determination unit, 300 . . . current detection unit, 301 . . . detection resistor, 302 . . . inspection power supply, 303 . . . current detection circuit, 400 . . . internal electrode, 500 . . . voltage application unit, 501 . . . resonance frequency detection unit, 502 . . . receptor property discrimination unit, 600 . . . switcher, 601 . . . coating position discrimination unit, 602 . . . fault discrimination unit, VL1 . . . virtual straight line passing through the center of membrane, VL2 . . . straight line orthogonal to straight line VL1

The invention claimed is:

1. A gas sensor, comprising:
an electrically conductive membrane configured to bend with an applied surface stress;
a fixing member located outside the membrane;
at least one pair of coupling portions located at least at two positions sandwiching the membrane when viewed from a thickness direction, and coupling together the membrane and the fixing member;
a flexible resistor whose resistance value varies in accordance with a deflection occurred in the at least one pair of coupling portions;
an electrically conductive support substrate connected to the fixing member and located with a gap between the membrane and the at least one pair of coupling portions;
a receptor formed on an area including a center of a surface on one side of the membrane, the one side being opposite the other side facing the support substrate, and deforming in accordance with an adsorbed substance;
a first terminal capable of applying a first potential to the membrane;
a second terminal capable of applying a second potential to the support substrate; and
an insulating portion configured to electrically insulate the fixing member from the support substrate.

2. The gas sensor according to claim 1, wherein the membrane is configured to deform in accordance with a voltage applied between the first terminal and the second terminal.

3. The gas sensor according to claim 1, further comprising a resistance detection unit configured to detect, as an inspection-time resistance value, a resistance value of the flexible resistor with a voltage being applied between the first terminal and the second terminal.

4. The gas sensor according to claim 1, further comprising a voltage application unit capable of applying a voltage between the first terminal and the second terminal.

5. The gas sensor according to claim 1, further comprising:
   a correction value storage unit configured to store, as a sensitivity correction value, a correction value of sensitivity according to a reference resistance value which is a reference value of a resistance value of the flexible resistor with a first voltage being applied between the first terminal and the second terminal, and an inspection-time resistance value which is a resistance value of the flexible resistor with a second voltage different from the first voltage being applied between the first terminal and the second terminal; and
   a sensitivity correction unit configured to correct a detected resistance value in accordance with the sensitivity correction value stored in the correction value storage unit.

6. The gas sensor according to claim 1, further comprising a detection substrate in which the membrane, the fixing member, and the at least one pair of coupling portions are integrally formed, wherein
   the detection substrate and the support substrate have different polarities from each other, and
   the insulating portion is formed using a depletion layer formed between the detection substrate and the support substrate.

7. The gas sensor according to claim 1, further comprising:
   a resonance frequency detection unit configured to detect, from a resistance value of the flexible resistor, a resonance frequency of the membrane, the at least one pair of coupling portions and the receptor; and
   a receptor property discrimination unit configured to discriminate a physical property of the receptor based on a reference value of the resonance frequency and the detected resonance frequency.

8. The gas sensor according to claim 1, further comprising:
   a bridge circuit constituted from the flexible resistor;
   a bridge voltage application unit configured to apply a bridge voltage to the bridge circuit;
   a coating position discrimination unit configured to discriminate a coating position of the receptor from an output value of the bridge circuit with a first voltage being applied between the first terminal and the second terminal, and an output value of the bridge circuit with a second voltage different from the first voltage being applied between the first terminal and the second terminal; and
   a switcher capable of switching a connection between a terminal for applying the bridge voltage of the bridge circuit and the bridge voltage application unit, and a connection between an output terminal of the bridge circuit and the coating position discrimination unit.

9. A component detector, comprising:
   the gas sensor according to claim 1;
   a resistance detection unit configured to detect, as an inspection-time resistance value, a resistance value of the flexible resistor with a voltage being applied between the first terminal and the second terminal;
   a pattern storage unit storing a response pattern with which the receptor responds to a component contained in a fluid when the fluid adheres; and
   a component detection unit configured to detect a component contained in the fluid adhered to the receptor in accordance with the inspection-time resistance value detected by the resistance detection unit and the response pattern stored in the pattern storage unit.

10. An inspection system, comprising:
    the gas sensor according to claim 1;
    a voltage application unit capable of applying a voltage between the first terminal and the second terminal; and
    a resistance detection unit configured to detect, as an inspection-time resistance value, a resistance value of the flexible resistor with a voltage being applied between the first terminal and the second terminal.

11. The inspection system according to claim 10, further comprising:
    a correction value storage unit configured to store, as a sensitivity correction value, a correction value of sensitivity according to a reference resistance value which is a reference value of a resistance value of the flexible resistor with a first voltage being applied between the first terminal and the second terminal, and an inspection-time resistance value which is a resistance value of the flexible resistor with a second voltage different from the first voltage being applied between the first terminal and the second terminal; and
    a sensitivity correction unit configured to correct a detected resistance value in accordance with the sensitivity correction value stored in the correction value storage unit.

12. A gas sensor inspection method for inspecting operation of the membrane for the gas sensor according to claim 1, comprising:
    a second voltage application step of applying a second voltage between the first terminal and the second terminal;
    an inspection-time resistance detection step of detecting, as an inspection-time resistance value, a resistance value of the flexible resistor with the second voltage being applied between the first terminal and the second terminal; and
    a determination step of determining operation of the membrane based on the inspection-time resistance value detected in the inspection-time resistance detection step and a reference resistance value which is a resistance value with a first voltage different from the second voltage being applied between the first terminal and the second terminal.

13. The gas sensor inspection method according to claim 12, further comprising a first voltage application step of applying the first voltage between the first terminal and the second terminal and a measurement step of measuring the reference resistance value with the first voltage being applied between the first terminal and the second terminal in the first voltage application step, as a pre-step of the second voltage application step.

14. The gas sensor inspection method according to claim 12, further comprising:
    a correction value calculation step of calculating, when the operation of the membrane is determined to be better than a reference value in the determination step, a sensitivity correction value which is a correction value of sensitivity according to the inspection-time resistance value detected in the inspection-time resistance detection step;
    a correction value storage step of storing the sensitivity correction value calculated in the correction value calculation step; and an inspection-time resistance value correction step of correcting the inspection-time resistance value using the sensitivity correction value stored in the correction value storage step.

15. A gas sensor inspection method for inspecting a physical property of the receptor for the gas sensor according to claim 1, comprising:
- a second voltage application step of applying a second voltage between the first terminal and the second terminal;
- an inspection-time resistance detection step of detecting an inspection-time resistance value which is a resistance value of the flexible resistor with the second voltage being applied between the first terminal and the second terminal;
- a resonance frequency calculation step of calculating a resonance frequency of the receptor from the inspection-time resistance value detected in the inspection-time resistance detection step; and
- a receptor property discrimination step of discriminating a physical property of the receptor by comparing a reference value of the resonance frequency with the resonance frequency calculated in the resonance frequency calculation step.

16. A gas sensor inspection method for inspecting a coating position of the receptor for the gas sensor according to claim 1, comprising:
- a bridge voltage application step of applying a bridge voltage to a bridge circuit constituted from the flexible resistor; and
- a coating position discrimination step of discriminating a coating position of the receptor from an output value of the bridge circuit with a first voltage being applied between the first terminal and the second terminal and an output value of the bridge circuit with a second voltage different from the first voltage being applied between the first terminal and the second terminal.

17. The gas sensor inspection method according to claim 16, further comprising a connection switching step of switching a connection between a terminal for applying the bridge voltage of the bridge circuit and a bridge voltage application unit for applying a bridge voltage to the bridge circuit, and a connection between the output terminal of the bridge circuit and the coating position discrimination unit for discriminating a coating position of the receptor,
Wherein the connection switching step is performed prior to the coating position discrimination step.

18. A gas sensor manufacturing method, comprising:
- a laminate formation step of forming a concave portion on one side of a support substrate, forming an insulating portion on the one side, and then laminating a detection substrate to cover a part of the support substrate where the insulating portion has been formed, so that a laminate with a gap between the support substrate and the detection substrate is formed;
- a through-electrode formation step of removing a part of the detection substrate to form a through-hole penetrating from a surface on one side of the detection substrate to the support substrate, the one side being opposite to the other side facing the support substrate, and then forming a through-electrode reaching from the surface to the support substrate by burying the through-hole with an electrode material containing impurities;
- a first ion implantation step of implanting first ions into a selected partial area of the surface located outside a preset area including a center of the detection substrate;
- a second ion implantation step of implanting second ions into a selected area located outside the area of the detection substrate where the first ions have been implanted;
- a third ion implantation step of implanting third ions into a selected area of the surface of the detection substrate;
- a low-resistance area formation step of, by heat-treating the laminate, forming a first low-resistance area in the area where the first ions have been implanted, forming a second low-resistance area in the area where the second ions have been implanted, forming a third low-resistance area in the area where the third ions have been implanted, and solid-phase diffusing impurities from the through-electrode into the support substrate, so that a fourth low-resistance area is formed in a preset area of one side of the support substrate, the one side facing the detection substrate;
- a removal step of, by removing an area around a preset area including the center of the detection substrate and excluding the first low-resistance area, forming a membrane configured to bend with an applied surface stress, a fixing member surrounding the membrane with a gap when viewed from a thickness direction of the membrane, and at least one pair of coupling portions located at least at two positions sandwiching the membrane when viewed from the thickness direction and coupling together the membrane and the fixing member; and
- a wiring layer formation step of forming a wiring layer including a first terminal electrically connected to the membrane and a second terminal electrically connected to the support substrate.

* * * * *